(12) United States Patent
Momose et al.

(10) Patent No.: US 6,211,215 B1
(45) Date of Patent: Apr. 3, 2001

(54) HETEROCYCLIC COMPOUNDS, THEIR PRODUCTION AND USE

(75) Inventors: Yu Momose, Takarazuka; Etsuya Matsutani, Suita, both of (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/180,955

(22) PCT Filed: Jul. 17, 1997

(86) PCT No.: PCT/JP97/02479

§ 371 Date: Nov. 18, 1998

§ 102(e) Date: Nov. 18, 1998

(87) PCT Pub. No.: WO98/03505

PCT Pub. Date: Jan. 29, 1998

(30) Foreign Application Priority Data

Jul. 19, 1996 (JP) .................................................. 8-191100
Jun. 12, 1997 (JP) .................................................. 9-155177

(51) Int. Cl.[7] ........................ C07D 413/12; A61K 31/425
(52) U.S. Cl. ........................ 514/374; 514/365; 514/367; 548/202; 548/217; 548/235
(58) Field of Search ........................ 248/202, 235, 248/217; 514/374, 365, 367

(56) References Cited

U.S. PATENT DOCUMENTS

| | | | |
|---|---|---|---|
| 5,466,610 | 11/1995 | Bright et al. | 436/518 |
| 5,480,896 | 1/1996 | Malamas et al. | 514/364 |
| 5,482,954 | 1/1996 | Kohn et al. | 514/359 |
| 5,869,485 | * 2/1999 | Missbach | 514/234.2 |

FOREIGN PATENT DOCUMENTS

| | | |
|---|---|---|
| 92/03425 | 3/1992 | (WO) . |
| 94 03427 | 2/1994 | (WO) . |
| 95/04049 | 2/1995 | (WO) . |
| WO9610028 | * 4/1996 | (WO) ................ 514/234.2 |

OTHER PUBLICATIONS

T.Yoneda et al., "The Antiproliferative Effects of Tyrosine Kinsae Inhibitors Tyrophostins on a Human Squamous Cell Carcinoma in Vitro and in Nude Mice", Cancer Research, vol. 51, No. 16, Aug. 15, 1991, pp. 4430–4435.

H. Umezawa et al., "Studies on a New Epidermal Growth Factor–Receptor Kinase Inhibitor, Erbstatin, Produced by MH435–hF3", The Journal of Antibiotics, vol. 39, No. 1, Jan. 1986, pp. 170–173.

A.P. Combs et al., "Protein Structure–Based Combinatorial Chemistry: Discovery of Non–Peptide Binding Elements to Src SH3 Domain", Journal of the American Chemical Society, vol. 118, No. 1, 1996, pp. 287–288.

J.V. Duncia et al., "Three Synthetic Routes to a Sterically Hindered Tetrazole. A New One–Step Mild Conversion of an Amide into a Tetrazole", Journal of Organic Chemistry, vol. 56, 1991, pp. 2395–2400.

J. Wrobel et al., "Novel Spirosuccinimides with Incorporated Isoindolone and Benzisothiazole 1,1–Dioxide Moieties as Aldose Reductase Inhibitors and Antihyperglycemic Agents", J. Med. Chem., vol. 35, No. 24, 1992, pp. 4613–4627.

S. Goldstein et al., "Hydroxyurea Derivatives as Hypoglycemic Agents", J. Med. Chem., vol. 36, No. 15, 1993, pp. 2238–2240.

* cited by examiner

Primary Examiner—Robert Gerstl
(74) Attorney, Agent, or Firm—Wenderoth, Lind & Ponack, L.L.P.

(57) ABSTRACT

Heterocyclic compounds represented by the general formula (I)

$$R-(CH_2)_n-X-\underset{Y}{\overset{A}{\bigcirc}}-(CH_2)_m-NB$$ (I)

wherein R stands for an optionally substituted aromatic heterocyclic group;

X stands for oxygen atom, an optionally oxidated sulfur atom, —C(=O)— or —CH(OH)—;

Y stands for CH or N;

m denotes an integer of 0 to 10:

n denotes an integer of 1 to 5:

cyclic group

—NB stands for an optionally substituted aromatic azole group; and ring A is optionally further substituted, or salts thereof. The compound (I) possesses action of inhibiting tyrosine kinase and useful as antitumor agents.

21 Claims, No Drawings

HETEROCYCLIC COMPOUNDS, THEIR PRODUCTION AND USE

TECHNICAL FIELD

The present invention relates to a heterocyclic compound useful as the growth factor receptor tyrosine kinase (especially HER2) inhibiting agent, a method of producing the compound, and a medicinal composition comprising the compound.

BACKGROUND ART

Genes of cell growth factor and growth factor receptors are called proto-oncogene and play important roles in behavior of human tumors including breast cancer (Arronson et al., Science Vol.254, pp.1141–1153, 1991). HER2 (Human EGF Receptor-2 genes having homology with the receptor of epidermal growth factor EGF are those of transmembrane receptor glycoprotein, and this receptor has tyrosine kinase activity (Akiyama et al., Science Vol.232, pp.1644–1656, 1986). HER2 is observed in human breast cancer and ovarian cancer (Slamon et al., Science, Vol.244, pp.707–712, 1989), which is further observed in prostate cancer (Lyne et al., Proceedings of American Association for Cancer Research Vol.37, p.243, 1996) or gastric cancer (Yonemura et al., Cancer Research Vol.51, p.1034, 1991). Further, the substrate of HER2-tyrosine kinase is observed in 90% of pancreatic cancers. Transgenic mice carrying HER2 gene develop mammary cancers as they grow (Guy et al., Proceedings of National Academy of Science U.S.A., Vol.89, pp.10578–10582, 1992).

It is disclosed that antibodies specific for HER2 suppress in vitro proliferation of tumor cells (Mckenzie et al. Oncogene Vol.4, pp.543–548, 1989) and humanized monoclonal antibody demonstrated prospective results in the clinical tests of patients suffering from breast cancer (Baselga et al., Journal of Clinical Oncology, Vol.14, pp.737–747, 1996).

These antibodies hinder the binding of growth factor with HER2 receptor and inhibit activation of tyrosine kinase. As the result, since it was shown that the advance of breast cancer was suppressed, it was shown that the drug directly inhibiting tyrosine kinase of HER2 was possibly effective as a medicine for the therapy of breast cancer (Hayes, Journal of Clinical Oncology, Vol.14, pp.697–699, 1996).

While several low molecular weight compounds inhibiting receptor-type tyrosine kinase containing HER2 have been reported, most of them are styrene-like compounds analogous to tyrosine itself having hydroxylated aromatic ring. For example, erbstatin inhibits proliferation of human epidermal carcinoma cell line A431 (Journal of Antibiotics, Vol.39, p.170, 1986), and it is reported that tyrphostin has antitumor activity in vivoon nude mice bearing the well-characterized human squamous cell carcinoma MH-85 (Cancer Research, Vol.51, p.4430, 1991). And, it it reported that sulfonylbenzoyl-nitrostyrene derivatives have antitumor activities in vivo in nude mice carrying A431 cell line. Further, it has been known that indole derivatives inhibit EGF receptor type tyrosine kinase and inhibit in vivo the growth of A431 cell line (International Application No. PCT/US93/7272, Japanese Patent Application under PCT laid-open under Kohyo No.Toku-Hyo-Hei 8-503450).

And, it has been known that triazole and diazole derivatives, although they are not tyrosine kinase inhibiting compounds, have the activity of inhibiting the signal transduction of cell proliferation due to growth factor (U.S. Pat. No. 5,482,954).

DISCLOSURE OF INVENTION

The object of this invention is to provide a compound having an action of inhibiting tyrosine kinase, being useful as an antitumor agent with less toxicity.

The present inventors conducted various studies on heterocyclic compounds having a tyrosine kinase inhibiting action, and, as a result, they synthesized, for the first time, a heterocyclic compound represented by the general formula (I) having a terminal aromatic azole group,

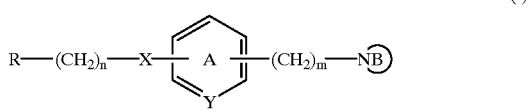

(I)

wherein R stands for an optionally substituted aromatic heterocyclic group;

X stands for oxygen atom, an optionally oxidized sulfur atom, —C(=O)— or —CH(OH)—;

Y stands for CH or N;

m denotes an integer of 0 to 10;

n denotes an integer of 1 to 5; and the cyclic group

stands for an optionally substituted aromatic azole group, and the ring A may optionally further be substituted (hereinafter simply called "compound (I)"), or a salt thereof, and found that this compound (I) or a salt thereof has, unexpectedly, an excellent suppressing action of tyrosine kinase based on the specific chemical structure. Based on this finding, the present invention has been accomplished.

More specifically, the present invention is to provide (1) the heterocyclic compound (I) or a salt thereof;

(2) a medicinal composition comprising the heterocyclic compound (I) or a pharmaceutically acceptable salt thereof;

(3) use of the heterocyclic compound (I) or a pharmaceutically acceptable salt thereof, for a preparation of a medicinal agent for prophylaxis or treatment for cancer;

(4) a method comprising administering an effective amount of the heterocyclic compound (I) or a pharmaceutically acceptable salt thereof in a pharmaceutically acceptable carrier to provide a prophylactic or therapeutic action for cancer; and (5) a method of producing the heterocyclic compound (I) or a salt thereof.

In the present specification, as the heterocyclic group in the optionally substituted aromatic heterocyclic group shown by R, mention is made of, for example, (1) a 5- or 6-membered aromatic monocyclic heterocyclic group containing as the ring-forming atoms, besides carbon atoms, 1 to 4 atoms selected from nitrogen atom, oxygen atom and sulfur atom, and (2) an aromatic condensed heterocyclic group formed by condensation of (i) a 5- or 6-membered aromatic monocyclic heterocyclic group containing, as the ring-forming atoms, besides carbon atoms, 1 to 4 atoms selected from nitrogen atom, oxygen atom and sulfur atom with (ii) a 5- or 6-membered aromatic or non-aromatic heterocyclic group containing, as the ring-forming atoms, besides carbon atoms, 1 to 2 nitrogen atoms, benzene ring or a 5-membered aromatic or non-aromatic heterocyclic group containing, as the ring-forming atoms, besides carbon atoms, one sulfur atom.

Specific examples of these aromatic heterocyclic groups include pyridyl (e.g. 2-pyridyl, 3-pyridyl, 4-pyridyl), pyrimidinyl (2-pyrimidinyl, 5-pyrimidinyl, 6-pyrimidinyl), pyridazinyl (e.g. 3-pyridazinyl, 4-pyridazinyl), pyrazinyl (e.g. 2-pyrazinyl), pyrrolyl (e.g. 1-pyrrolyl, 2-pyrrolyl), imidazolyl (e.g. 1-imidazolyl, 2-imidazolyl, 4-imidazolyl, 5-imidazolyl), pyrazolyl (e.g. 1-pyrazolyl, 3-pyrazolyl, 4-pyrazolyl), isoxazolyl, isothiazolyl, thiazolyl (e.g. 2-thiazolyl, 4-thiazolyl, 5-thiazolyl), oxazolyl (e.g. 2-oxazolyl, 4-oxazolyl, 5-oxazolyl), oxadiazolyl (e.g. 1,2,4-oxadiazolyl such as 1,2,4-oxadiazol-5-yl, 1,2,3-oxadiazolyl, 1,3,4-oxadiazolyl), thiadiazolyl (e.g. 1,2,3-thiadiazolyl, 1,2,4-thiadiazolyl, 1,3,4-thiadiazolyl), triazolyl (e.g. 1,2,4-triazolyl such as 1,2,4-triazol-1-yl, 1,2,4-triazol-5-yl, 1,2,4-triazolyl such as 1,2,3-triazol-1-yl, 1,2,3-triazol-2-yl, 1,2,3-triazol-4-yl), tetrazolyl (e.g. tetrazol-1-yl, tetrazol-5-yl), benzimidazolyl (e.g. benzimidazol-1-yl, benzimidazol-2-yl), indolyl (e.g. indol-1-yl, indol-3-yl), indazolyl (e.g. 1H-indazol-1-yl, 1H-indazol-3-yl), pyrrolopyrazinyl (e.g. 1H-pyrrolo[2,3-b]pyrazinyl), pyrrolopyridyl (e.g. 1H-pyrrolo[2,3-b]pyridyl), imidazopyridyl (e.g. 1H-imidazo[4,5-b]pyridyl, 1H-imidazo[4,5-c]pyridyl, imidazopyrazinyl (e.g. 1H-imidazo[4,5-bpyrazinyl), pyrrolopyridazinyl (e.g. pyrrolo[1,2-b]pyridazinyl), pyrazolpyridyl (e.g. pyrazolo[1,5-a]pyridyl), imidazopyridyl (e.g. imidazo[1,2-a]pyridyl, imidazo[1,5-a]pyridyl), imidazopyridazinyl (e.g. imidazo[1,2-b]pyridazinyl), imidazopyrimidinyl (e.g. imidazo[1,2-a]pyrimidinyl), furyl, thienyl, benzofuranyl, benzothienyl (e.g. benzo[b]thienyl), benzoxazolyl, benzthiazolyl, quinolyl, isoquinolyl and quinazolinyl. Preferable examples include a 5-membered cyclic aromatic azole group such as oxazolyl, thiazolyl, isoxazolyl, isothiazolyl, imidazolyl, triazolyl, oxadiazolyl and thiadiazolyl, an aromatic condensed azole group formed by condensation with a benzene ring such as benzoxazolyl and benzthiazolyl, and a 6-membered monocyclic aromatic heterocyclic group such as pyridyl and pyrimidyl. Further preferable examples of the aromatic heterocyclic group include a 5-membered monocyclic aromatic azole group such as oxazolyl group and thiazolyl group.

As the aromatic azole group in the optionally substituted aromatic azole group shown by the cyclic group:

, mention is made of, for example, (1) a 5-membered aromatic monocyclic heterocyclic group containing, as the ring-forming atoms, besides carbon atoms, 1 to 4 nitrogen atoms and optionally containing one oxygen atom or one sulfur atom, and (2) an aromatic condensed heterocyclic group formed by condensation of (i) a 5-membered aromatic monocyclic heterocyclic group containing, as the ring forming atoms, besides carbon atoms, 1 to 4 nitrogen atoms and optionally containing one nitrogen atom or one sulfur atom, with (ii) a 5- or 6-membered aromatic or non-aromatic heterocyclic group containing, as the ring-forming atoms, besides carbon atoms, one or two nitrogen atoms, benzene ring or a 5-membered aromatic or non-aromatic heterocyclic group containing, as the ring-forming atoms, besides carbon atoms, one sulfur atom.

Specific example of the aromatic azole group include aromatic heterocyclic groups such as pyrrolyl (e.g. 1-pyrrolyl), imidazolyl (e.g. 1-imidazolyl), pyrazolyl (e.g. 1-pyrazolyl), triazolyl (e.g. 1,2,4-triazol-1-yl, 1,2,3-triazol-1-yl), tetrazolyl (e.g. tetrazol-1-yl), benzimidazolyl (e.g. benzimidazol-1-yl), indolyl (e.g. indol-1-yl), indazolyl (e.g. 1H-indazol-1-yl), pyrrolopyrazinyl (e.g. 1H-pyrrolo[2,3-b]pyrazin-1-yl), pyrrolopyridyl (e.g. 1H-pyrrolo[2,3-b]pyridin-1-yl), imidazopyridyl (e.g. 1H-imidazo[4,5-b]pyridin-1-yl), and imidazopyrazinyl (e.g. 1H-imidazo[4,5-b]pyrazin-1-yl). These groups are bonded to —$(CH_2)_m$— through the nitrogen atom contained as one of the ring-forming atoms. Preferable examples of the aromatic azole group include imidazolyl group and triazolyl group.

The aromatic heterocyclic group shown by R and the aromatic azole group shown by the formula:

may optionally have 1 to 3 (preferably one or two) substituents at any substitutable position. Examples of the substituents include aliphatic hydrocarbon groups, alicyclic hydrocarbon groups, aromatic hydrocarbon groups, an aliphatic hydrocarbon group substituted with an aromatic hydrocarbon group, an aliphatic hydrocarbon group substituted with an alicyclic hydrocarbon group, aromatic heterocyclic groups, non-aromatic heterocyclic groups, an aliphatic hydrocarbon group substituted with an aromatic heterocyclic group, halogen atom, nitro group, cyano group, an optionally substituted amino group, an optionally substituted acyl group, an optionally substituted hydroxyl group, an optionally substituted thiol group, and an optionally esterified or amidated carboxyl group. The aliphatic hydrocarbon group, alicyclic hydrocarbon group, aromatic hydrocarbon group, aliphatic hydrocarbon group substituted with an aromatic hydrocarbon group, aliphatic hydrocarbon group substituted with an aliphatic hydrocarbon group, aromatic heterocyclic group, non-aromatic heterocyclic group and aliphatic hydrocarbon group substituted with an aromatic heterocyclic group may further be optionally substituted, respectively.

The ring A may optionally have, besides X and $(CH_2)_m$, 1 to 4 (preferably one or two) substituents at any substitutable position. As the substituents, mention is made of those exemplified as substituents which the substituents on the aromatic heterocyclic groups shown by R may optionally have, as exemplified by aliphatic hydrocarbon groups, alicyclic hydrocarbon groups, aromatic hydrocarbon groups, an aliphatic hydrocarbon group substituted with an aromatic hydrocarbon group, an aliphatic hydrocarbon group substituted with an alicyclic hydrocarbon group, aromatic heterocyclic groups, an aliphatic hydrocarbon group substituted with an aromatic heterocyclic group, halogen atom, nitro group, cyano group, an optionally substituted amino group, an optionally substituted acyl group, an optionally substituted hydroxyl group, an optionally substituted thiol group, and an optionally esterified or amidated carboxyl group. The aliphatic hydrocarbon group, alicyclic hydrocarbon group, aromatic hydrocarbon group, aliphatic hydrocarbon group substituted with an aromatic hydrocarbon group, aliphatic hydrocarbon group substituted with an alicyclic hydrocarbon group, aromatic heterocyclic group, non-aromatic heterocyclic group and aliphatic hydrocarbon group substituted with an aromatic heterocyclic group mentioned above as substituents may optionally be further substituted.

As the aliphatic hydrocarbon groups, mention is made of straight-chain or branched aliphatic hydrocarbon groups having 1 to 15 carbon atoms, for example, alkyl group, alkenyl group and alkynyl group.

Preferable examples of the alkyl group include $C_{1-10}$ alkyl groups such as methyl, ethyl, propyl, isopropyl, butyl, isobutyl, sec.-butyl, tert.-butyl, pentyl, isopentyl, neopentyl, tert.-pentyl, hexyl, isohexyl, heptyl, octyl, nonyl, decyl, 1,1-dimethylbutyl, 2,2-dimethylbutyl, 3,3-dimethylbutyl and 2-ethylbutyl, more preferably $C_{1-6}$ alkyl groups.

Preferable examples of the alkenyl group include $C_{2-10}$ alkenyl groups such as vinyl (ethenyl), allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl and 5-hexenyl, more preferably $C_{2-6}$ alkenyl groups.

Preferable examples of the alkynyl group include $C_{2-10}$ alkynyl groups such as ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl, more preferably $C_{2-6}$ alkynyl groups.

Examples of the alicyclic hydrocarbon group include $C_{3-12}$ saturated or unsaturated alicyclic hydrocarbon groups such as cycloalkyl group, cycloalkenyl group, cycloalkadienyl group or partially unsaturated condensed dicyclic hydrocarbon group.

Preferable examples of the cycloalkyl group include $C_{3-10}$ cycloalkyl groups such as cyclopropyl, cyclobutyl, cyclopentyl, cyclohexyl, cycloheptyl and cyclooctyl; and $C_{6-10}$ bicycloalkyl groups such as bicyclo[2.2.1]heptyl, bicyclo[2.2.2]octyl, bicyclo[3.2.1]octyl, bicyclo[3.2.2]nonyl, bicyclo[3.3.1]nonyl, bicyclo[4.2.1]nonyl and bicyclo[4.3.1]decyl.

Preferable examples of the cycloalkenyl group include $C_{5-10}$ cycloalkenyl groups such as 2-cyclopenten-1-yl, 3-cyclopenten-1-yl, 2-cyclohexen-1-yl and 3-cyclohexen-1-yl.

Preferable examples of the cycloalkadienyl group include $C_{5-10}$ cycloalkadienyl groups such as 2,4-cyclopentadien-1-yl, 2,4-cyclohexadien-1-yl and 2,5-cyclohexadien-1-yl.

Preferable examples of the partially unsaturated condensed dicyclic hydrocarbon group include $C_{9-12}$ groups formed by condensation of a benzene ring such as indanyl group or partially unsaturated naphthyl group (e.g. dihydronaphthyl group such as 3,4-dihydro-2-naphthyl; and tetrahydronaphthyl such as 1,2,3,4-tetrahydronaphthyl) with alicyclic hydrocarbon.

As the aromatic hydrocarbon group, mention is made of a monocyclic or a condensed polycyclic aromatic hydrocarbon group, preferably exemplified by $C_{6-14}$ aryl groups such as phenyl, naphthyl, anthryl, phenanthryl acenaphthylenyl and 9-fluorenone-2-yl. Among them, monocyclic or condensed dicyclic aromatic hydrocarbon groups such as phenyl, 1-naphthyl and 2-naphthyl are preferable.

As the aliphatic hydrocarbon group substituted with an aromatic hydrocarbon group, mention is made of, for example, aliphatic hydrocarbon groups substituted with 1 to 3 (preferably 1 or 2) $C_{7-20}$ aromatic hydrocarbon groups. Preferable examples of such aliphatic hydrocarbon group substituted with an aromatic hydrocarbon group as above include $C_{1-6}$ alkyl group substituted with 1 to 3 $C_{6-14}$ aryl groups (e.g. $C_{1-6}$ alkyl group substituted with 1 to 3 phenyl groups such as benzyl, 2-phenylethyl, 1,2-diphenylethyl and 2,2-diphenylethyl) and $C_{2-6}$ alkenyl groups substituted with 1 to 3 $C_{6-14}$ aryl groups (e.g. $C_{2-6}$ alkenyl groups substituted 1 to 3 phenyl groups, such as (E)-2-phenylethenyl, (Z)-2-phenylethenyl, 2,2-diphenylethenyl, 2-(2-napthyl)ethenyl and 4-phenyl-1,3-butadienyl, and $C_{2-6}$ alkenyl groups or 9-fluorenyl-$C_{1-6}$ alkyl group substituted with 1 to 3 napthyl groups).

As the aliphatic hydrocarbon group substituted with an alicyclic hydrocarbon group, mention is made of the above-mentioned aliphatic hydrocarbon groups substituted with the above-mentioned alicyclic hydrocarbon groups.

Preferable examples of such aliphatic hydrocarbon group substituted with an alicyclic hydrocarbon group include $C_{1-6}$ alkyl groups substituted with 1 to 3 $C_{3-10}$ cycloalkyl groups such as cyclopropylmethyl, cyclopropylethyl, cyclobutylmethyl, cyclopentylmethyl, 2-cyclopentenylmethyl, 3-cyclopentenylmethyl, cyclohexylmethyl, 2-cyclohexenylmethyl, 3-cyclohexenylmethyl, cyclohexylethyl, cyclohexylpropyl, cycloheptylmethyl; $C_{2-6}$ alkenyl groups substituted with 1 to 3 $C_{3-10}$ cycloalkyl groups; $C_{1-6}$ alkyl groups substituted with 1 to 3 $C_{5-10}$ cycloalkenyl groups; and $C_{2-6}$ alkenyl groups substituted with 1 to 3 $C_{5-10}$ cycloalkenyl groups.

As preferable examples of the aromatic heterocyclic group, mention is made of the 5- or 6-membered aromatic monocyclic heterocyclic group containing, as ring-forming atoms, besides carbon atoms, 1 to 4 atoms selected from nitrogen atom, oxygen atom and sulfur atom, such as furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl,, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl and triazinyl; and the aromatic condensed heterocyclic group formed by condensation of (i) a 5- or 6-membered aromatic heterocyclic group containing, as ring-forming atoms, besides carbon atoms, 1 to 4 atoms selected from nitrogen atom, oxygen atom and sulfur atom with (ii) a 5- or 6-membered aromatic or a non-aromatic heterocyclic group containing, as ring-forming atoms, besides carbon atoms, 1 or 2 nitrogen atoms, benzene ring or a 5-membered aromatic or a non-aromatic heterocyclic group containing, as ring-forming atoms, besides carbon atoms, one sulfur atom, such as benzofuranyl, isobenzofuranyl, benzo[b]thienyl, indolyl, isoindolyl, 1H-indazolyl, benzimidazolyl, benzoxazolyl, 1,2-benzisoxazolyl, benzothiazolyl, 1,2-benzisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxathiinyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, and 1,2,4-triazolo[4,3-b]pyridazinyl.

Preferable examples of the non-aromatic heterocyclic group include a 3- to 7-membered non-aromatic heterocyclic group containing, as ring forming atoms, besides carbon atoms, 1 or 2 atoms selected from nitrogen atom, oxygen atom and sulfur atom, such as oxiranyl, azetidinyl, oxetanyl, thietanyl, pyrrolidinyl, tetrahydrofuryl, thiolanyl, piperidyl, tetrahydropyranyl, morpholinyl, thiomorpholinyl and piperazinyl.

As aliphatic hydrocarbon group substituted with an aromatic heterocyclic group, mention is made of a $C_{1-6}$ aliphatic hydrocarbon group substituted with 1 to 3 (preferably 1 or 2) of the above-mentioned aromatic heterocyclic groups (for example, $C_{1-6}$ alkyl group and $C_{2-6}$ alkenyl group). Preferable examples of the aliphatic hydrocarbon group substituted with an aromatic heterocyclic group include $C_{1-6}$ alkyl group with 1 to 3 of, for example, furyl group, thienyl group, imidazolyl group or pyridyl group (e.g. (2-furyl)

methyl, thienylmethyl and 2-(1-imidazolyl)ethyl), and $C_{2-6}$ alkenyl group substituted with 1 to 3 of furyl group, thienyl group, imidazolyl group or pyridyl group.

As halogen atoms, mention is made of, for example, fluorine, chlorine, bromine and iodine, especially fluorine and chlorine being preferable.

As the optionally substituted amino group, mention is made of amino groups optionally mono- or di-substituted with, for example, a $C_{1-10}$ alkyl group, a $C_{3-10}$ cycloalkyl, a $C_{2-10}$ alkenyl group, a $C_{5-10}$ cycloalkenyl group, a $C_{1-10}$ acyl group or a $C_{6-12}$ aromatic hydrocarbon group (e.g. methylamino, dimethylamino, ethylamino, diethylamino, dibutylamino, diallylamino, cyclohexylamino, acetylamino, propionylamino, benzoylamino, phenylamino and N-methyl-N-phenylamino) and 4- to 6-membered cyclic amino groups (e.g. 1-azetidinyl, 1-pyrrolidinyl, piperidino, morpholino and 1-piperazinyl).

The said 4- to 6-membered cyclic amino groups may optionally be further substituted with (1) $C_{1-6}$ alkyl group, (2) $C_{6-14}$ aryl group optionally substituted with halogen, $C_{1-6}$ alkoxy group or trifluoromethyl (e.g. phenyl and naphthyl), (3) 5- or 6-membered heterocyclic group containing, as ring-forming atoms, besides carbon atoms, 1 to 2 nitrogen atoms (e.g. 2-pyridyl and pyrimidinyl) or (4) 6-membered cyclic amino group (e.g. piperidino and 1-piperazinyl).

As the acyl group of optionally substituted acyl group, mention is made of $C_{1-13}$ acyl groups, more specifically, besides formyl, those formed by linkage of, for example, a $C_{1-6}$ alkyl group, a $C_{3-10}$ cycloalkyl group, a $C_{2-6}$ alkenyl group, a $C_{5-10}$ cycloalkenyl group, a $C_{6-12}$ aromatic hydrocarbon group (e.g. phenyl and naphthyl) or a aromatic heterocyclic ring (e.g. pyridyl) with carbonyl group, as exemplified by $C_{2-7}$ alkanoyl groups (e.g. acetyl, propionyl, butyryl, isobutyryl, valeryl, isovaleryl, pivaloyl, hexanoyl, heptanoyl and octanoyl), $C_{3-10}$ cycloalkyl-carbonyl groups (e.g. cyclobutanecarbonyl, cyclopentanecarbonyl, cyclohexanecarbonyl and cycloheptanecarbonyl), $C_{3-7}$ alkenoyl groups (e.g. crotonoyl group), $C_{5-10}$ cycloalkenyl-carbonyl groups (e.g. 2-cyclohexenecarbonyl), benzoyl group and nicotinoyl group.

As substituents in the optionally substituted acyl group, mention is made of, for example, $C_{1-3}$ alkyl groups, $C_{1-3}$ alkoxy groups, halogen (e.g. chlorine, fluorine and bromine), nitro group, hydroxyl group and amino group. The number of substituents ranges, for example, from 1 to 3.

Examples of the optionally substituted hydroxyl group include hydroxyl group, alkoxy group, cycloalkyloxy group, alkenyloxy group, cycloalkenyloxy group, aralkyloxy group, aryloxy group and acyloxy group.

Preferable examples of the alkoxy group include $C_{1-10}$ alkoxy groups such as methoxy, ethoxy, propoxy, isopropoxy, butoxy, isobutoxy, sec.-butoxy, tert.-butoxy, pentyloxy, isopentyloxy, neopentyl, hexyloxy, heptyloxy and nonyloxy.

Preferable examples of the cycloalkyloxy group include $C_{3-10}$ cycloalkyloxy groups such as cyclobutoxy, cyclopentyloxy and cyclohexyloxy.

Preferable examples of the alkenyloxy group include $C_{2-10}$ alkenyloxy groups such as allyloxy, crotyloxy, 2-pentenyloxy and 3-hexenyloxy.

Preferable examples of the cycloalkenyloxy group include $C_{5-10}$ cycloalkenyloxy groups such as 2-cyclopentenyloxy and 2-cyclohexenyloxy.

Preferable examples of the aralkyloxy group include $C_{7-12}$ aralkyloxy groups such as $C_{6-14}$ aryl-$C_{1-6}$ alkoxy groups such as phenyl-$C_{1-6}$ alkoxy group (e.g. benzyloxy and phenethyloxy), naphthyl-$C_{1-6}$ alkoxy group.

Preferable examples of the aryloxy group include a $C_{6-14}$ aryloxy group optionally substituted with a $C_{1-3}$ alkyl group, a $C_{1-3}$ alkoxy group, halogen, nitro group, hydroxyl group or amino group, which are exemplified, more specifically, phenoxy and 4-chlorophenoxy.

Preferable examples of the acyloxy group include $C_{2-15}$ acyloxy groups such as $C_{2-7}$ alkanoyloxy groups (e.g. acetyloxy, propionyloxy, butyryloxy and isobutyryloxy), $C_{6-14}$ aryl-carbonyloxy (e.g. benzoyloxy and naphthoyloxy).

Examples of the optionally substituted thiol group include mercapto group, alkylthio group, cycloalkylthio group, alkenylthio group, aralkylthio group, arylthio group, heteroarylthio group, heteroarylalkylthio group and acylthio group.

Preferable examples of the alkylthio group include $C_{1-10}$ alkylthio groups such as methylthio, ethylthio, propylthio, isopropylthio, butylthio, isobutylthio, sec.-butylthio, tert.-butylthio, pentylthio, isopentylthio, neopentylthio, hexylthio, heptylthio and nonylthio.

Preferable examples of the cycloalkylthio group include $C_{3-10}$ cycloalkylthio groups such as cyclobutylthio, cyclopentylthio and cyclohexylthio.

Preferable examples of the alkenylthio group include $C_{2-10}$ alkenylthio groups such as allylthio, crotylthio, 2-pentenylthio and 3-hexenylthio.

Preferable examples of the aralkylthio group include $C_{7-20}$ aralkylthio groups such as $C_{6-14}$ arylthio groups, exemplified, more specifically, by phenyl-$C_{1-6}$ alkylthio (e.g. benzylthio and phenethylthio), and naphthyl-$C_{1-6}$ alkylthio.

Preferable examples of the arylthio group include a $C_{6-14}$ arylthio group optionally substituted with a $C_{1-3}$ alkyl group, a $C_{1-3}$ alkoxy group, halogen, nitro group, hydroxyl group or amino group, such as phenylthio, naphthylthio and 4-chlorophenylthio.

As the heteroarylthio group, mention is made of, for example, the mercapto group substituted with an aromatic heterocyclic group as mentioned above, especially preferable one being imidazolylthio (e.g. 2-imidazolylthio) or triazoylthio (e.g. 1,2,4-triazol-5-ylthio).

As the heteroarylalkylthio group, mention is made of, for example, the above-mentioned alkyl thio group substituted with the above-mentioned aromatic heterocyclic group. Preferable examples of the heteroarylthio group include pyridyl-$C_{1-6}$ alkylthio groups (e.g. 2-pyridylmethylthio and pyridylmethylthio).

Preferable examples of the acylthio group include $C_{2-15}$ acylthio groups, such as $C_{2-7}$ alkanoylthio groups (e.g. acetylthio, propionylthio, butyrylthio and isobutyrylthio), $C_{6-14}$ aryl-carbonylthio (e.g. benzoylthio and naphthoylthio).

As optionally esterified or amidated carboxyl groups, mention is made of carboxyl group, esterified carboxyl group and amidated carboxyl group.

Examples of the esterified carboxyl group include alkoxy carbonyl groups, aralkyloxy carbonyl groups, aryloxycarbonyl groups and heteroarylalkyloxycarbonyl groups.

Preferable examples of the alkoxycarbonyl groups include $C_{2-7}$ alkoxycarbonyl groups such as methoxycarbonyl, ethoxycarbonyl, propoxycarbonyl and butoxycarbonyl.

Preferable examples of the alkoxycarbonyl group include $C_{8-21}$ aralkyloxycarbonyl such as phenyl-$C_{2-7}$ alkoxycarbonyl (e.g. benzyloxycarbonyl) and naphthyl-$C_{2-7}$ alkoxycarbonyl.

Preferable examples of the aryloxycarbonyl group include, $C_{7-15}$ aryloxycarbonyl groups optionally substituted with $C_{1-3}$ alkyl groups, $C_{1-3}$ alkoxy groups, halogen, nitro group, hydroxyl group or amino group, such as phenoxycarbonyl and p-tolyloxycarbonyl.

As the heteroarylalkyloxycarbonyl, mention is made of, for example, the above-mentioned alkoxycarbonyl groups substituted with the above-mentioned aromatic heterocyclic groups. Preferable examples of the heteroarylalkyloxycarbonyl group include pyridyl-$C_{2-7}$ alkoxycarbonyl groups (e.g. 2-pyridylmethoxycarbonyl and 3-pyridylmethoxycarbonyl).

As the amidated carboxyl group, mention is made of groups represented by the formula: —CON($R^1$)($R^2$) [wherein $R^1$ and $R^2$ independently stand for H and optionally substituted hydrocarbon groups or optionally substituted heterocyclic groups]. As the hydrocarbon group in optionally substituted hydrocarbon groups shown by $R^1$ or $R^2$, mention is made of the aliphatic hydrocarbon groups, alicyclic hydrocarbon groups and aromatic hydrocarbon groups exemplified as substituents on the aromatic heterocyclic groups shown by R. And, as the heterocyclic group in optionally substituted heterocyclic groups shown by $R^1$ or $R^2$, mention is made of the aromatic heterocyclic groups exemplified as substituents on the aromatic heterocyclic groups shown by R.

As substituents on the hydrocarbon groups or heterocyclic groups in $R^1$ or $R^2$, mention is made of 1 to 3 substituents selected from halogen atoms (e.g. chlorine, fluorine, bromine and iodine), $C_{1-6}$ alkyl groups and $C_{1-6}$ alkoxy groups.

In the general formula (I), when the aromatic heterocyclic group shown by R, the aromatic azole group shown by the cyclic group

—N̂B or the substituent on ring A is an alicyclic hydrocarbon group, aromatic hydrocarbon group, aliphatic hydrocarbon group substituted with aromatic hydrocarbon group, aromatic heterocyclic group, non-aromatic heterocyclic group or aliphatic hydrocarbon group substituted with aromatic heterocyclic group, the said alicyclic hydrocarbon group, aromatic hydrocarbon group, the aromatic hydrocarbon group in the aliphatic hydrocarbon group substituted with an aromatic hydrocarbon group, aromatic heterocyclic group, non-aromatic hydrocarbon group or the aromatic heterocyclic group in the aliphatic hydrocarbon group substituted with an aromatic heterocyclic group may optionally have further 1 to 3 (preferably 1 or 2) substituents on respectively substitutable positions. Examples of such substituents include optionally substituted $C_{1-6}$ alkyl groups, $C_{2-6}$ alkenyl groups, $C_{2-6}$ alkynyl groups, $C_{3-10}$ cycloalkyl groups, $C_{5-10}$ cycloalkenyl groups, $C_{6-14}$ aryl groups (e.g. phenyl and naphthyl), aromatic heterocyclic groups (e.g. thienyl, furyl, pyridyl, oxazolyl, thiazolyl and tetrazolyl), non-aromatic heterocyclic groups (e.g. tetrahydrofuryl, morpholinyl, pyrrolidyl and piperazinyl), $C_{7-20}$ aralkyl groups (e.g. phenyl-$C_{1-6}$ alkyl groups, naphthyl-$C_{1-6}$ alkyl groups), amino group, N-mono($C_{1-6}$)alkylamino group, N,N-di($C_{1-6}$)alkylamino groups, $C_{2-7}$ acylamino groups (e.g. $C_{2-7}$ alkanoylamino groups such as acetylamino and propionylamino, and benzoylamnino group), amidino group, $C_{2-7}$ acyl groups (e.g. $C_{2-7}$ alkanoyl groups and benzoyl group), carbamoyl group, N-mono($C_{1-6}$) alkylcarbamoyl groups, N,N-di($C_{1-6}$)alkylcarbamoyl groups, sulfamoyl group, N-mono($C_{1-6}$)alkylsulfamoyl group, N,N-di ($C_{1-6}$)alkylsulfamoyl group, carboxyl group, $C_{2-7}$ alkoxycarbonyl groups, $C_{8-21}$ aralkyloxycarbonyl groups (e.g. phenyl-$C_{2-7}$ alkoxycarbonyl and naphthyl-$C_{2-7}$ alkoxycarbonyl), hydroxyl group, optionally substituted $C_{1-6}$ alkoxy groups, $C_{2-6}$ alkenyloxy groups, $C_{3-10}$ cycloalkyloxy groups, $C_{5-10}$ cycloalkenyloxy groups, $C_{7-20}$ aralkyloxy groups (e.g. phenyl-$C_{1-6}$ alkoxy groups, naphthyl-$C_{1-6}$ alkoxy groups), $C_{6-14}$ aryloxy groups (e.g. phenoxy and naphthyloxy), mercapto, $C_{1-6}$ alkylthio groups, $C_{3-10}$ cycloalkylthio groups, $C_{7-20}$ aralkylthio groups (e.g. phenyl-$C_{1-6}$ alkyl groups and naphthyl-$C_{1-6}$ alkylthio), $C_{6-14}$ arylthio groups (e.g. phenylthio and naphthylthio), sulfo group, cyano group, azide group, nitro group, nitroso group, and halogen atoms (e.g. fluorine, chlorine, bromine and iodine).

As substituents in the above-mentioned optionally substituted $C_{1-6}$ alkoxy groups and optionally substituted $C_{1-6}$ alkyl groups, mention is made of, for example, 1 to 3 substituents selected from halogen atoms (e.g. fluorine, chlorine, bromine and iodine), hydroxyl group and $C_{1-6}$ alkoxy groups.

As the substituted $C_{1-6}$ alkoxy groups, mention is made of, for example, trifluoromethoxy, difluoromethoxy, 2,2,2-trifluoroethoxy and 1,1-difluoroethoxy.

As the substituted $C_{1-6}$ alkyl groups, mention is made of, for example, trifluoromethyl, difluoromethyl, 2,2,2-trifluoroethyl, trichloromethyl, hydroxymethyl, methoxymethyl, 2-methoxyethyl and 2,2-dimethoxyethyl.

In the general formula (I), when the aromatic heterocyclic group shown by R, the aromatic azole group shown by the cyclic group

—N̂B or the substituent on ring A is an aliphatic hydrocarbon group substituted with an aliphatic hydrocarbon group or aromatic hydrocarbon group, or an aliphatic hydrocarbon group substituted with a aromatic heterocyclic group, said aliphatic hydrocarbon group, the aliphatic hydrocarbon group in the aliphatic hydrocarbon group substituted with an aromatic hydrocarbon group, or the aliphatic hydrocarbon group in the aliphatic hydrocarbon group substituted with an aromatic heterocyclic group may have further 1 to 3 (preferably 1 or 2) substituents at respectively substitutable positions. Examples of these substituents include non-aromatic heterocyclic groups (e.g. tetrahydrofuryl, morpholinyl, piperidyl, pyrrolidyl and piperazinyl), amino group, N-mono($C_{1-6}$)alkylamino groups, N,N-di($C_{1-6}$) alkylamino groups, $C_{2-7}$ acylamino groups (e.g. $C_{2-8}$ alkanoylamino groups such as acetylamino and propionylamino, and benzoylamino group), amidino group, $C_{2-7}$ acyl groups (e.g. $C_{2-7}$ alkanoyl group and benzoyl group), carbamoyl group, N-mono($C_{1-6}$)alkylcarbamoyl groups, N,N-di($C_{1-6}$)alkylcarbamoyl groups, sulfamoyl group, N-mono($C_{1-6}$)alkylsulfamoyl groups, N,N-di($C_{1-6}$) alkylsulfamoyl groups, carboxyl group, $C_{2-7}$ alkoxycarbonyl groups, $C_{8-21}$ aralkyloxycarbonyl groups (e.g. phenyl-$C_{2-7}$ alkoxycarbonyl groups and naphthyl-$C_{2-7}$ alkoxycarbonyl groups), hydroxyl group, optionally substituted $C_{1-6}$ alkoxy groups, $C_{2-6}$ alkenyloxy groups, C3-10 cycloalkyloxy groups, $C_{5-10}$ cycloalkenyloxy groups, $C_{7-20}$ aralkyloxy groups (e.g. phenyl-$C_{1-6}$ alkoxy groups and naphthyl-$C_{1-6}$ alkoxy groups), $C_{6-14}$ aryloxy groups (e.g. phenoxy and naphthyloxy), mercapto group, $C_{1-6}$ alkylthio groups, $C_{3-10}$ cycloalkylthio groups, $C_{7-20}$ aralkylthio groups (e.g. phenyl-$C_{1-6}$ alkyl groups, naphthyl-$C_{1-6}$ alkyl groups), $C_{6-14}$ arylthio groups (e.g. phenylthio and naphthylthio), sulfon group, cyano group, azide group, nitro group, nitroso group, halogen atoms (e.g. fluorine, chlorine, bromine and iodine).

As the substituents in the above-mentioned optionally substituted $C_{1-6}$ alkoxy group, mention is made of, for example, 1 to 3 substituents selected from halogen atoms (e.g. fluorine, chlorine, bromine and iodine), hydroxyl group, and $C_{1-6}$ alkoxy groups.

As the above-mentioned substituted $C_{1-6}$ alkoxy groups, mention is made of, for example, trifluoromethoxy, difluoromethoxy, 2,2,2-trifluoroethoxy and 1,1-difluoroethoxy.

Preferable examples of R are oxazolyl group or thiazolyl group respectively substituted with 1 or 2 substituents selected from (i) aryl group optionally substituted with 1 or 2 substituents selected form hydroxyl group, alkoxy group (e.g. $C_{1-6}$ alkoxy group), arylalkoxy group (e.g. phenyl-$C_{1-6}$ alkoxy group), alkyl group (e.g. $C_{1-6}$ alkyl group), cyano group, halogen atom and tetrazolyl group (e.g. phenyl group and naphthyl group), (ii) alkyl group (e.g. $C_{1-10}$ alkyl group), (iii) hydroxyalkyl group (e.g. hydroxy-$C_{1-10}$ alkyl group), (iv) alkoxycarbonylalkyl group (e.g. $C_{2-7}$ alkoxycarbonyl-$C_{1-10}$ alkyl group), (v) alkyl group substituted with 1 or 2 aryl groups (e.g. $C_{1-6}$ alkyl group substituted with 1 or 2 phenyl groups), (vi) alkenyl group substituted with 1 or 2 aryl groups (e.g. $C_{2-6}$ alkenyl group substituted with 1 or 2 phenyl group), (vii) cycloalkyl group (e.g. $C_{3-10}$ cycloalkyl group), (viii) partially saturated naphthyl group (e.g. dihydronaphthyl group), (ix) thienyl or furyl group optionally substituted with 1 or 2 substituents selected from hydroxyl group, alkoxy group, arylalcohol group, alkyl group, cyano group, aryl group and halogen atom, (x) benzofuranyl group and (xi) benzothienyl, and oxazolyl group substituted with arylalkenyl group (e.g. phenyl-$C_{2-6}$ alkenyl group) and oxazolyl group or benzoxazlolyl substituted with arylalkoxy-aryl group (e.g. phenyl-$C_{1-6}$ alkoxy-phenyl group) are more preferable.

Preferable examples of the cyclic group

include pyrrolyl group, imidazolyl group, pyrazolyl group, triazolyl group, tetrazolyl group or benzimidazolyl group respectively substituted with 1 or 2 substituents selected from (i) alkyl group (e.g. $C_{1-10}$ alkyl group), (ii) aryl group (e.g. phenyl group), (iii) hydroxylalkyl group (e.g. hydroxy-$C_{1-10}$ alkyl group), (iv) carboxyl group, (v) alkoxycarbonyl group (e.g. $C_{2-7}$ alkoxycarbonyl group) and (vi) carbamoyl group, and imidazolyl group and triazolyl group are more preferable.

The ring A forms, depending on the kind of Y (CH or N), optionally substituted benzene ring or optionally substituted pyridine ring. As preferable examples, mention is made of optionally substituted benzene ring. More preferable examples include benzene ring optionally substituted with 1 or 2 $C_{1-6}$ alkoxy groups or pyridine ring.

Preferable examples of the ring A

include

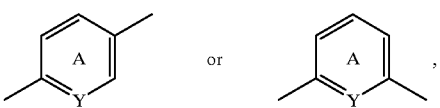

and most preferable ones are 1,3-phenylene group or 1,4-phenylene group.

X stands for oxygen atom (O), an optionally oxidized sulfur atom [$S(O)_k$ (k denotes an integer of 0 to 2)], —C(=O)— or —CH(OH)—, and the preferable examples include oxygen atom.

The symbol m denotes an integer of 0 to 10, preferable 0 to 6, more preferably 3 to 5.

The symbol n denotes an integer of 1 to 5, preferably 1.

As salts of the compound (I) of this invention, pharmaceutically acceptable ones are preferable, as exemplified by salts of inorganic bases, salts of organic bases, salts with inorganic acids, salts of organic acids, and salts of basic or acidic amino acids. Preferable examples of salts with inorganic bases include alkali metal salts such as sodium salt and potassium salt; alkaline earth metal salts such as calcium salt and magnesium salt; and aluminum salt and ammonium salt. Preferable examples of salts with organic bases include salts with trimethylamine, triethylamine, pyridine, picoline, ethanolamine, diethanolamine, triethanolamine, dicyclohexylamine and N,N-dibenzylethylenediamine. Preferable examples of salts with inorganic acids include salts with hydrochloric acid, hydrobromic acid, nitric acid and phosphoric acid. Preferable examples of salts with organic acids include salts with formic acid, acetic acid, trifluoroacetic acid, fumaric acid, oxalic acid, tartaric acid, maleic acid, citric acid, succinic acid, malic acid, methanesulfonic acid, benzenesulfonic acid and p-toluenesulfonic acid. Preferable examples of salts with basic amino acids include salts with arginine, lysine and ornithine. Preferable example of salts with acidic amino acid include salts with aspartic acid and glutamic acid. The compound (I) of this invention or salts thereof may optionally be used as hydrates.

The compound (I) or a salt thereof of this invention [hereinafter containing the compound (I) or a salt thereof] can be produced by, for example, the following methods. Additionally stating, in the following production methods, not only the compounds shown by the respective formulae but also their salts may optionally be used. Examples of these salts include those set forth as the salts of the compound (I). And, in each production method, when the product is obtained as free form, it can be converted to the corresponding salt, and, when the product is obtained as a salt, it can be converted to the the free compound, in accordance with conventional methods, respectively.

In the reactions described in the following, when, for example, $NH_2$, OH or COOH is included in the substituents, the compounds in which these groups are protected may optionally be employed as starting compounds, and, after completion of the reaction, the protecting group is removed to produce the object compound. As amino-protecting group, mention is made of, for example, acyl group (e.g. $C_{2-7}$ alkanoyl group such as acetyl; $C_{2-7}$ alkoxycarbonyl such as benzyloxycarbonyl and tert.-butoxycarbonyl; phthaloyl group and hydroxyl group). As hydroxyl-protecting group, mention is made of, for example, $C_{1-6}$ alkyl groups, phenyl-$C_{1-6}$ alkyl groups, $C_{2-7}$ alkanoyl groups and benzoyl group. As carboxyl-protecting group, mention is made of, for example, $C_{1-6}$ alkyl group and phenyl-$C_{1-6}$ alkyl groups.

Incidentally stating, when the object compound contains unsaturated bonds in the substituents, it may optionally be subjected to, for example, conventional catalytic reduction to lead to the object compound having the corresponding saturated substituents.

Method A

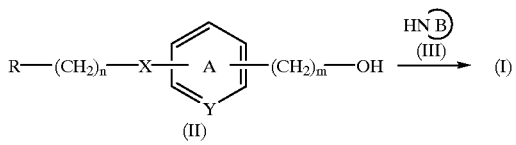

wherein each symbol is of the same meaning as defined above.

In this method, the compound (I) is produced by subjecting the compound (II) to condensation with the compound (III). This reaction is conducted, in accordance with a conventional method, in a solvent inert to the reaction, in the presence of an organic phosphorus compound such as triphenylphosphine or tributylphosphine and an electrophilic agent such as diethyl azodicarboxylate, diisopropyl azodicarboxylate or azodicarbonyl dipiperazine. Examples of the solvent include ethers such as diethyl ether, tetrahydrofuran and dioxane; halogenated hydrocarbons such as chloroform and dichloromethane; aromatic hydrocarbons such as benzene, toluene and xylene; N,N-dimethylformamide; dimethyl sulfoxide; and a mixed solvent of them. The amount of these organic phosphorus compounds and electrophilic agents to be employed ranges, preferably from 1 to 5 molar equivalents relative to the compound (II). The amount of the compound (III) to be employed ranges, preferably from 1 to 10 molar equivalents relative to the compound (II). This reaction is conducted usually at temperatures ranging from −50 to 150° C., preferably from about −1 to 100° C. over a period ranging from 0.5 to 20 hours. The compound (I) thus obtained can be isolated and purified by a known isolating and purifying means such as concentration, concentration under reduced pressure, solvent extraction, crystallization, recrystallization, phasic transfer and chromatography.

Method B

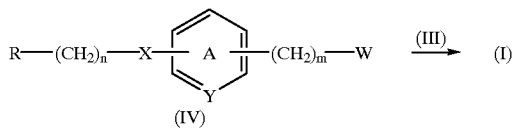

wherein W stands for a leaving group, and other symbols are of the same meaning as defined above.

Examples of the leaving group shown by W include halogen atoms and a group shown by the formula: —OSO$_2$R$^3$, R$^3$ stands for an aryl group optionally substituted with a $C_{1-6}$ alkyl group such as methyl and ethyl or p-tolyl (e.g. phenyl group optionally substituted with a $C_{1-6}$ alkyl group).

In this method, the compound (I) is produced by subjecting the compound (IV) to condensation with the compound (III). This reaction is conducted in accordance with a conventional method, in a solvent inert to the reaction in the presence of a base. Examples of the solvent include aromatic hydrocarbons such as benzene, toluene and xylene; ethers such as tetrahydrofuran and dioxane; ketones such as acetone and 2-butanone; halogenated hydrocarbons such as chloroform and dichloromethane; N,N-dimethylformamide; dimethyl sulfoxide; and a mixed solvent of them. Examples of the base include alkali metal salts such as potassium hydroxide, sodium hydroxide, sodium hydrogen carbonate and potassium carbonate; amines such as pyridine, triethylamine and N,N-dimethyl aniline; metal hydrides such as potassium hydride and sodium hydride; and sodium methoxide, sodium ethoxide and tert.-butoxide. The amount of these bases to be employed ranges, preferably, from 1 to 5 molar equivalents relative to the compound (IV). The amount of the compound (III) to be employed ranges, preferably, from about 1 to 10 molar equivalents relative to the compound (IV). This reaction is conducted at temperatures usually ranging from −50 to 150° C., preferably from about −10 to 100° C., over a period ranging from 0.5 to 20 hours. The compound (I) thus obtained can be isolated and purified by a known isolating and purifying means such as concentration, concentration under reduced pressure, solvent extraction, crystallization, recrystallization, phasic transfer and chromatography.

Method C

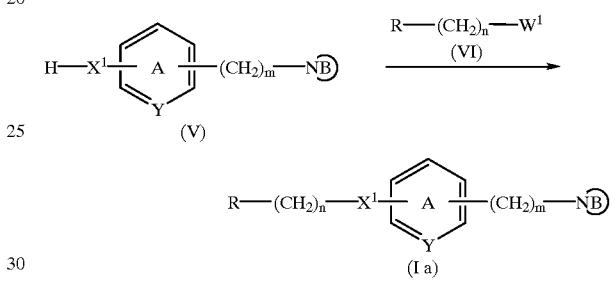

wherein X$^1$ stands for oxygen atom or sulfur atom, W$^1$ stands for a leaving group, and other symbols are of the same meaning as defined above.

Examples of the leaving group shown by W$^1$ include halogen atoms and a group shown by the formula: —OSO$_2$R$^4$, R$^4$ stands for an aryl group optionally substituted with a $C_{1-6}$ alkyl group such as methyl and ethyl or p-tolyl (e.g. phenyl group optionally substituted with a $C_{1-6}$ alkyl group).

In this method, the compound (V) is allowed to react with the compound (VI) to produce the compound (Ia). This reaction is conducted in a solvent inert to the reaction, in the presence of a base. Examples of the solvent include ethers such as tetrahydrofuran and dioxane; aromatic hydrocarbons such as toluene and xylene; N,N-dimethylformamide, dimethyl sulfoxide, acetone or water; and a mixed solvent of them. Examples of the base include potassium carbonate, sodium hydrogencarbonate, sodium methoxide, sodium ethoxide, sodium hydride, potassium hydroxide, sodium hydroxide and lithium hydroxide. The amount of the compound (VI) to be employed ranges from about 1 to 10 molar equivalents relative to the compound (V). This reaction is conducted at temperatures ranging usually from −20 to 15° C., preferably from about 0 to 100° C. over a period ranging from 1 to 20 hours. The compound (Ia) thus obtained can be isolated and purified by a known isolating and purifying means such as concentration, concentration under reduced pressure, solvent extraction, crystallization, recrystallization, phasic transfer and chromatography.

Method D

It is also possible that the compound (Ic), which is a compound (I) wherein R and/or

is a group having an optionally esterified carboxyl group, is subjected to reduction to give the compound (Id), which is a compound (I) wherein R and/or

is a group having hydroxymethyl group. This reduction can be conducted by a per se known means, for example, reduction using a metal hydride, a metal hydride complex compound, diborane or a substituted borane. More specifically, this reaction is conducted by processing the compound (Ic) with a reducing agent. Examples of the reducing agent include alkali metal borohydrides (e.g. sodium borohydride and lithium borohydride), metal hydride complex compounds such as lithium aluminum hydride, organotin compounds such as triphenyltin hydride, and diborane. This reaction is conducted in an organic solvent inert to the reaction. As the solvent, use is made of, for example, aromatic hydrocarbons such as benzene, toluene and xylene, halogenated hydrocarbons such as chloroform, dichloromethane and carbon tetrachloride, ethers such as tetrahydrofuran and dioxane, alcohol such as methanol and ethanol, N,N-dimethylformamide or a mixed solvent of them, suitably depending on kinds of the reducing agent then employed. This reaction is conducted at temperatures ranging usually from −20 to 150° C., preferably from about 0 to 100° C. over a period ranging from 0.1 to 10 hours. The compound (Id) thus obtained can be isolated and purified by a known isolating and purifying means such as concentration, concentration under reduced pressure, solvent extraction, crystallization, recrystallization, phasic transfer and chromatography.

Method E

It is also possible that the compound (Ie), which is a compound (I) wherein R and/or

is a group having cyano group is allowed to react with an azide compound to give the compound (If), which is a compound (I) wherein R and/or

is a group having 1H-tetrazol-5-yl group. This reaction can be conducted by a per se known method. For example, the reaction is conducted, in accordance with the method described in Journal of American Chemical Society Vol.80 p.3908 (1957), by the reaction with sodium azide and ammonium chloride in N,N-dimethylformamide. The amounts of sodium azide and ammonium chloride are respectively 1 to 7 molar equivalents, preferably 1 to 5 molar equivalents, relative to the compound (Ie). This reaction is conducted at temperatures ranging usually from 0 to 180° C., preferably from 50 to 150° C. over a period ranging from 1 to 48 hours. And, this reaction can be conducted also, in accordance with the method described in Journal of organic Chemistry Vol.56 p.2395 (1991), by the reaction with trimethyltin azide or tributyltin azide, followed by treating with an acid. The compound (If) thus obtained can be isolated and purified by a known separating and purifying means such as concentration, concentration under reduced pressure, solvent extraction, crystallization, recrystallization, phasic transfer and chromatography.

Method F

It is also possible that the compound (Ih), which is the compound (I) wherein X is oxidized sulfur atom $[S(O)_k$ (wherein k denotes 1 or 2)], by subjecting the compound (Ig), which is the compound (I) wherein X is oxidized sulfur atom $[S(O)_k$ (wherein k denotes 0)], to oxidation. This reaction is conducted by oxidizing the compound (Ig) with an oxidizing agent. As the oxidizing agent, use is made of, for example, m-chloroperbenzoic acid, hydrogen peroxide, peresters and sodium metaperiodate. This reaction is conducted in an organic solvent inert to the reaction. As the solvent, use is suitably made of, depending on the kinds of the oxidizing agent then employed, aromatic hydrocarbons such as benzene, toluene and xylene; halogenated hydrocarbons such as dichloromethane, chloroform and carbon tetrachloride; alcohols such as methanol and ethanol; or a mixed solvent of them. When the oxidizing agent is used in the equimolar or less amount relative to the compound (Ig), the compound (Ih) wherein k=1 is produced preferentially. When the oxidizing agent is used in an excess equimolar amount relative to the compound (Ig), the compound (Ih) wherein k=2 is produced preferentially. This reaction is conducted usually at temperatures ranging from 50 to +100° C., preferably from −20 to +50° C. over a period of 0.5 to 10 hours. The compound (Ih) thus obtained can be isolated and purified by a known separating and purifying means such as concentration, concentration under reduced pressure, solvent extraction, crystallization, recrystallization, phasic transfer and chromatography.

Method G

It is also possible that the compound (Ij), which is the compound (I) wherein X is —CH(OH)—, can be produced by subjecting the compound (Ii), which is the compound (I) wherein X is —C(=O)—, to reduction. This reaction is conducted by processing the compound (Ii) with a reducing agent. As the reducing agent, use is made of, for example, alkali metal borohydrides such as sodium borohydride and lithium borohydride; metal hydride complex compounds such as lithium aluminum hydride; and diborane. This reaction is conducted in an organic solvent inert to the reaction. As the solvent, use is suitably made of, depending on the kinds of the reducing agent then employed, aromatic hydrocarbons such as benzene, toluene and xylene; halogenated hydrocarbons such as dichloromethane, chloroform and carbon tetrachloride; ethers such as tetrahydrofuran and dioxane; alcohols such as methanol and ethanol; N,N-dimethylformamide or a mixed solvent of them. This reaction is conducted at temperatures usually ranging from −20 to +150° C., preferably from 0 to +100° C., over a period of 0.5 to 10 hours. The compound (Ij) thus obtained can be isolated and purified by a known separating and purifying means such as concentration, concentration under reducing pressure, solvent extraction, crystallization, recrystallization, phasic transfer and chromatography.

Method H

It is also possible that the compound (Im), which is the compound (I) wherein R is alkoxy group, can be produced by subjecting the compound (Ik), which is the compound (I) wherein R is hydroxyl group. This reaction is conducted in substantially the same manner as in Method A or C. The compound (Im) thus obtained can be isolated and purified by a known separating and purifying means such as concentration, concentration under reduced pressure, solvent extraction, crystallization, recrystallization, phasic transfer and chromatography.

Method I

It is also possible that the compound (Io), which is the compound (I) wherein R is alkoxy, can be produced by allowing the compound (In), which is the compound (I) wherein R is halogen or a group having sulfonyloxy group, to react with aryl boric acid. This reaction is conducted by a known method per se, for example, in the presence of a metal catalyst such as zero-valent palladium or zero-valent nickel and a base in accordance with a method described in Journal of Organic Chemistry Vol. 58, 2201 (1993) or Journal of Organic Chemistry Vol. 60, 1060 (1955). As the palladium catalyst, use is made of, for example, tris(dibenzylideneacetone)dipalladium, tetrakis(triphenylphosphine)palladium; as the nickel catalyst, used is made of, for example, 1,1'-bis(diphenylphosphino) ferrocen nickel, etc. As the base, use is made of, for example, sodium hydrogen carbonate, sodium carbonate, potassium carbonate, tripotassium phosphate. This reaction is conducted in an organic solvent inert to the reaction. As the solvent, use is made of, for example, benzene, toluene, methanol, ethanol, tetrahydrofuran, dioxan and water, or a mixed solvent of them, suitably depending on kinds of the metal catalyst then employed. The amount of aryl boric acid to be employed is 1–7 molar equivalents, preferably 1–5 molar equivalents relative to the compound (In). The amount of the metal catalyst to be employed is 0.01–1 molar equivalent, preferably 0.05–0.5 molar equivalents. This reaction is usually conducted at −20–+150° C., preferably 0–100° C. for 0.1–24 hours. The compound (Io) thus obtained can be isolated and purified by a known isolation and purification mean such as concentration, concentration under reduced pressure, solvent extraction, crystallization, recrystallization, phasic transfer and chromatography.

The compound (II) to be employed in Method A can be synthesized by, for example, the method as shown below.

(1) When X is oxygen atom or sulfur atom:

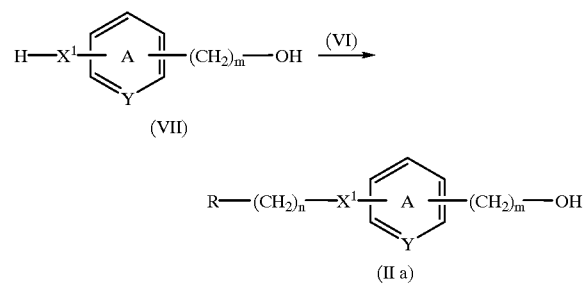

wherein each symbol is of the same meaning as defined above.

This reaction is to synthesize the compound (IIa) by subjecting the compound (VII) and the compound (VI) to condensation. This reaction is conducted in substantially the same manner as in Method C.

Incidentally, it is preferable that the hydroxyl group of $-(CH_2)_m-OH$ in the compound (VII) is protected, then the compound (VII) is subjected to condensation with the compound (VI), and the protective group is removed after completing the reaction.

(2) When X is oxidated sulfur atom $[S(O)_k$ (wherein k denotes 1 or 2)]:

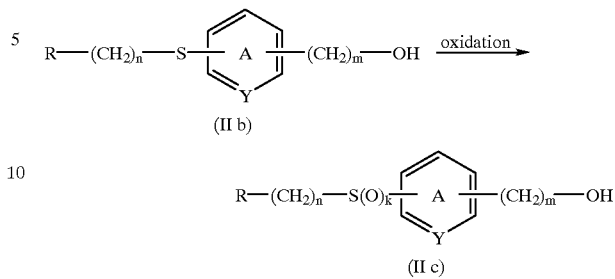

wherein each symbol is of the same meaning as defined above.

This reaction is a method of synthesizing the compound (IIc) by subjecting the compound (IIb) to oxidation. This reaction is conducted in substantially the same manner as in Method F.

The compound (IIb) employed herein can be obtained by allowing the afore-mentioned compound (VII) to react with the compound (VI).

(3) When X is $-C(=O)-$:

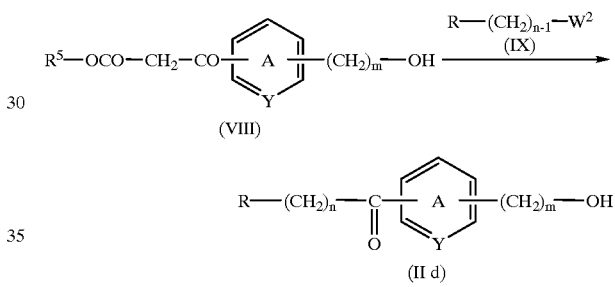

wherein $R^5$ stands for a $C_{1-6}$ alkyl group or a phenyl-$C_{1-6}$ alkyl group, $W^2$ stands for a halogen atom and other symbols are of the same meaning as defined above.

This reaction is a method to synthesize the compound (IId) by condensing the compound (VIII) with the compound (IX), followed by decarboxylation. In this reaction, at first, the compound (VIII) is condensed with the compound (IX) in a solvent in the presence of a base. Examples of the solvent include aromatic hydrocarbons such as benzene, toluene and xylene; ethers such as tetrahydrofuran and dioxane; alcohols such as methanol and ethanol; N,N-dimethylformamide, dimethylsulfoxide; or a mixed solvent of them. As the base, mention is made of, for example, sodium hydroxide, potassium hydroxide, sodium methoxide, sodium ethoxide, potassium t-butoxide, sodium hydride and potassium hydride. The amount of the base to be employed ranges from about 1 to 5 molar equivalents relative to the compound (VIII). This reaction is conducted at temperatures ranging usually from −20 to +150° C., preferably from 0 to +100° C. over a period of 0.5 to 10 hours.

Then, the condensed product obtained thus above was subjected to hydrolysis, which was then subjected to decarboxylation to synthesize the compound (IId). The hydrolysis is conducted, in accordance with a per se known method, in a hydrous solvent in the presence of an acid or a base. The carboxylic acid compound thus obtained is subjected to decarboxylation after isolation or without isolation to produce the compound (IId). This decarboxylation reaction is conducted in a solvent under heating. Examples of the solvent include aromatic hydrocarbons such as benzene, toluene and xylene; halogenated hydrocarbons such as dichloromethane, chloroform and carbon tetrachloride; ethers such as tetrahydrofuran and dioxane; alcohols such as methanol and ethanol; N,N-dimethylformamide, dimethylsulfoxide, pyridine, water; or a mixed solvent of them. This reaction is conducted at temperatures ranging usually form +50 to +250° C., preferably from +70 to +150° C. over a period of 5 to 24 hours.

The compound (VIII) employed herein can be synthesized by, for example, the method as shown below.

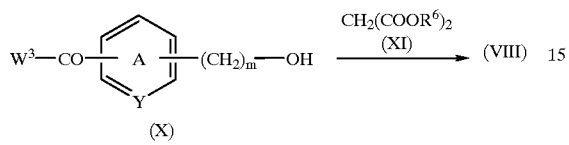

wherein $W^3$ stands for a halogen atom; $R^6$ stands for a $C_{1-6}$ alkyl group or phenyl-$C_{1-6}$ alkyl group; and other symbols are of the same meaning as defined above.

This reaction is a method to synthesize the compound (VIII) by condensing the compound (X) with the compound (XI), followed by decarboxylation. In this reaction, at first, the compound (X) is condensed with the compound (XI) in a solvent in the presence of a base. Examples of the solvent include aromatic hydrocarbons such as benzene, toluene and xylene; ethers such as tetrahydrofuran and dioxane; alcohols such as methanol and ethanol; N,N-dimethylformamide, dimethylsulfoxide; or a mixed solvent of them. As the base, mention is made of, for example, magnesium ethoxide. The amount of the base to be employed ranges from about 1 to 5 molar equivalents relative to the compound (XI). This reaction is conducted at temperatures ranging usually from −20 to +150° C., preferably from 0 to +100° C. over a period of 0.5 to 10 hours.

Subsequently, the condensed product thus obtained is subjected to hydrolysis, followed by decarboxylation to synthesize the compound (VIII). This hydrolysis and decarboxylation are conducted in substantially the same manner as in the hydrolysis and decarboxylation after the condensation of the compound (VIII) with the compound (IX).

Incidentally, it is also possible that the compound (VIII) is obtained by subjecting the compound (XI) to condensation after protecting the hydroxyl group of —(CH$_2$)$_m$—OH in the compound (X) and by subjecting the condensate to decarboxylation, followed by removing the protective group; or, without subjecting the compound (VIII), in which the hydroxyl group is protected, to deprotecting reaction, by subjecting the compound (VIII) to condensation with the compound (IX) and decarboxylation, followed by removing the protective group.

(4) When X is —CH(OH)—:

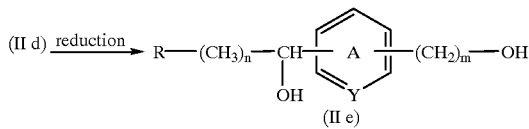

wherein each symbol is of the same meaning as defined above.

This reaction is a method of synthesizing the compound (IIe) by subjecting the compound (IId) to reduction. This reaction is conducted in substantially the same manner as in Method G.

The compound (IV) to be employed in Method B can be synthesized by, for example, the method as shown below.

(II)→(IV)

This reaction is a method of synthesizing the compound (IV) by allowing a halogenizing agent of sulfonylating agent to react with the compound (II). As the halogenating agent, use is made of, for example, hydrochloric acid, thionyl chloride or phosphorus tribromide, and, in this case, the compound (IV), in which W is halogen (e.g. chlorine or bromine), is produced. This reaction is conducted in a solvent such as benzene, toluene, xylene, dichloromethane or chloroform, or using an excess amount of a halogenating agent as the solvent, at temperatures ranging from −20 to +100° C. over a period of 5 to 24 hours. The amount of the halogenating agent to be employed ranges from 1 to 10 molar equivalents relative to the compound (II). As the sulfonylating agent, use is made of, for example, methanesulfonyl chloride, benzene sulfonyl chloride and p-toluenesulfonyl chloride. The compound (IV), in which W is a group represented by the formula: —OSO$_2$R$^3$ (wherein R$^3$ is of the same meaning as defined above), for example, methanesulfonyloxy, benzenesulfonyloxy or p-toluenesulfonyloxy, is produced. This reaction is conducted in a solvent such as benzene, toluene, xylene, dichloromethane, chloroform and ethyl acetate in the presence of a base at temperatures ranging from −20 to +100° C. over a period of 5 to 24 hours. Examples of the base include triethylamine, N-methyl morpholine, sodium hydrogencarbonate, potassium hydrogencarbonate, sodium carbonate and potassium carbonate. The amount of the base to be used ranges from 1 to 10 molar equivalents relative to the compound (II).

The compound (V) to be employed in Method C can be synthesized by, for example, a method as shown below.

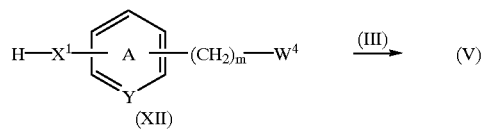

wherein $W^4$ stands for a leaving group, and other symbols are of the same meaning as defined above.

As the leaving group shown by $W^4$, mention is made of, for example, halogen atoms and groups represented by the formula: —OSO$_2$R$^7$ wherein R$^7$ stands for a C$_{1-6}$ alkyl group such as methyl and ethyl, or an optionally substituted aryl group such as p-tolyl (e.g. phenyl group optionally substituted with a C$_{1-6}$ alkyl group).

This reaction is a method of synthesizing the compound (V) by subjecting the compound (XII) to condensation with the compound (III). This reaction is conducted in substantially the same manner as in Method B.

The compound (I) of this invention or salts thereof are relatively low in toxicity and can be used as such or as a medicinal composition, for mammals including man (e.g. horse, cow, dog, cat, rat and mouse, rabbit, pig and monkey), prepared by mixing with a per se known pharmaceutically acceptable carrier or the like. And, in the medicinal composition, besides the compound (I) of this invention or a salt thereof, any other active component such as the following hormone therapeutic agents, chemotherapeutic agents and immunotherapeutic agents may optionally be allowed to be present.

The administration of the compound (I) or a salt thereof as a medicine to mammals including man is usually performed orally in the form of, for example, tablets, capsules (including soft capsules and microcapsules), powdery preparations and granular preparations, and, depending on cases, non-orally in the form of, for example, injections, suppositories and pellets. The dosage of the compound (I) or a salt thereof for a patient (40 to 80 kg body weight) having breast cancer or prostatic cancer ranges, while varying with the administration routes, symptoms or the like, in the case of oral administration, preferably from 1.0 to 100 mg/kg, more preferably from 5 to 50 mg/kg per day. This amount can be administered once daily or dividing into two to three times a day.

The compounds (I) and (II) or their salts of this invention, mixed with pharmaceutically acceptable carriers, can be administered orally or non-orally in the form of solid preparations such as tablets, capsules, granules and powdery preparations; or in the form of liquid preparations such as syrups and injections.

As pharmaceutically acceptable carriers, use is made of conventional organic or inorganic carriers for pharmaceutical preparations, more specifically, for example, excipients, lubricants, binders and disintegrators for solid preparations; and solvents, solubilizers, suspending agents, isotonizers, buffering agents and local anesthetic agents for liquid preparations. And, upon necessity, such additives as antiseptics, antioxidants, colorants and sweetners are further used.

Preferable examples of excipients include lactose, sucrose, D-mannitol, starch, crystalline cellulose and light silicon dioxide.

Preferable examples of lubricants include magnesium stearate, calcium stearate, talc and colloid silica.

Preferable examples of binders include crystalline cellulose, sucrose, D-mannitol, dextrin, hydroxypropyl cellulose, hydroxypropyl methyl cellulose and polyvinyl pyrrolidine.

Preferable examples of disintegrators include starch, carboxymethyl cellulose, carboxymethyl cellulose calcium, croscarmellose sodium and carboxymethyl starch sodium.

Preferable examples of solvents include distilled water for injection, alcohol, propylene glycol, macrogol, sesame oil and corn oil.

Preferable examples of solubilizers include polyethylene glycol, propylene glycol, D-mannitol, benzyl benzoate, ethanol, tris-amino methane, cholesterol, triethanolamine, sodium carbonate and sodium citrate.

Preferable examples of suspending agents include surfactants such as stearyl triethanolamine, sodium lauryl sulfate, lauryl aminopropionate, lecithin, benzalkonium chloride, benzethonium chloride and glycerin monostearate; and hydrophilic polymers such as polyvinyl alcohol, polyvinyl pyrrolidone, sodium carboxymethyl cellulose, methylcellulose, hydroxymethylcellulose, hydroxyethylcellulose and hydroxypropylcellulose.

Preferable examples of isotonizers include sodium chloride, glycerin and D-mannitol.

Preferable examples of buffering agents include buffer solutions of phosphates, acetates, carbonates and citrates.

Preferable examples of local anesthetic agents include benzyl alcohol.

Preferable examples of antiseptics include parahydroxybenzoic acid esters, chlorobutanol, benzyl alcohol, phenethyl alcohol, dehydroacetic acid and sorbic acid.

Preferable examples of antioxidants include sulfites and ascorbic acid.

The pharmaceutical preparation of this invention can be formulated, while varying with for example forms, administration routes and carriers, in accordance with a conventional method, by allowing the compound (I) of this invention or a salt thereof to be contained in an amount of 0.1 to 90% (w/w) relative to the total weight of the preparation.

And, the compound (I) of this invention can be administered to the same subject simultaneously with any other agents of hormone therapy, chemotherapy or immunotherapy, or it can be administered to the same subject with a time lag.

Examples of the hormone therapeutic agents include estrogen preparations or estrogen antagonistic preparations (e.g. tamoxifen), androgen preparations or androgen antagonistic preparations (e.g. flutamide), or LH-RH analog (e.g. leuprorelin, goserelin) or LH-RH antagonist.

Examples of the chemotherapeutic agents include alkylating agent (e.g. cyclophosphamide, iphosphamide), matabolic antagonists (e.g. methotrexate, 5-fluorouracil), antitumor antibiotics (e.g. mitomycin, adriamycin), and antineoplastic agents derived from plants (e.g. vincristine, vindesine, taxol), cisplatin, carboplatin and etoposide.

Examples of immunotherapeutic agents include microorganisms or cell components (e.g. muramyl dipeptide derivatives, pycivanyl), polysaccharides having immunostimulant activity (e.g. lentinan, sizofiran, krestin), cytokines obtained by means of genetic engineering (e.g. interferon, interleukin).

BEST MODE FOR CARRYING OUT THE INVENTION

The present invention will be illustrated in further detail in the following Test Examples, Formulation Examples, Reference Examples and Working Examples, which are not intended to limit this invention within the scope of these Examples.

Elution in the column chromatography conducted in Reference Examples and Working Examples was carried out while monitoring with TLC (Thin Layer Chromatography). In the TLC monitoring, as the TLC plate, use was made of $60F_{254}$ (70 to 230 mesh) plates manufactured by Merck & Co., Inc., as the developing solvent, use was made of the same solvent as employed for eluting in the column chromatography, and the detection was conducted with a UV detector. The silica gel for the column was Kieselguhr $60F_{254}$ (70 to 230 mesh) manufactured by Merck & Co. Inc. NMR spectra show proton NMR and were measured using tetramethylsilane as the internal standard with VARIAN Gemini-200 (270 MHZ type spectrometer). All δ values were expressed in ppm. And, the abbreviations used in Working Examples have the following meanings.

s:singlet, br:broad, d:doublet, t:triplet, q:quartet, dd:double doublet, dt:double triplet, ddd:doublet doublet doublet, m:multiplet, J:coupling constant, Hz:Hertz.

In the Test Examples, compound number means Working Example number (for example, the compound of Working Example 2 is expressed as Compound 2)

[WORKING EXAMPLES]

Test Example 1

Inhibition of the Activity of Human Growth Factor Receptor Tyrosine Kinases

As enzyme standard, the tyrosine kinase domain of the human HER2 gene was cloned to prepare the recombinant gene of insect virus vector, with which the insect cell line SF-21 was infected to produce an enzyme protein (Guy P. M.

et al., Journal of Biological Chemistry Vol. 267, pp.13851–13856, 1992). As substrate, the phosphorylated tyrosine domain of the HER3 protein was cloned to prepare the recombinant gene of plasmid vector with which *Escherichia Coli* strain JM109 was infected to give an enzyme protein (Sierke S. L. et al., Biochemistry Vol. 32, pp.10102–10108, 1993). The enzymatic reaction was performed by the enzyme-linked immunological method which consisted of fixing the substrate protein in wells of a 96-well microtiter plate, adding the enzyme into the wells and quantitating phosphorylated tyrosine, which was the reaction product, by use of the anti-phosphorylated tyrosine antibody (Cleaveland J. S. et al., Analytical Biochemistry Vol. 190, pp249–253, 1990). The results were expressed in terms of $IC_{50}$, the concentration of the compound which inhibited the phosphorylation of tyrosine by 50%, designating the phosphorylation of tyrosine in the control which did not contain the compound solution as 100%.

The results are shown in [Table 1].

TABLE 1

Inhibition of the HER2 receptor type tyrosine kinase activity

| Compound | Concentration of inhibiting HER2 ($IC_{50}$, $\mu M$) |
|---|---|
| 2 | 67 |
| 8 | 20 |

Test Example 2

Inhibition of Phosphorylation of Receptor Tyrosine in Human Breast Cancer Cells (1)

Human breast cancer cell line T-47D was cultured for 7 days in the medium containing 0.1% bovine fetus albumin instead of serum to deprive the medium of estrogen. On the 7th day, 1,000 $\mu l$ of the cell suspension (250,000 cells) was seeded in each well of the 24-well plates. The culture were incubated at 37° C. in a 5% carbon dioxide gas incubator. On the next day, 100 $\mu l$ of the 10-fold serial dilution of each compound solution was added to each well and, 2 hours later, 0.5 $\mu g/ml$ of heregulin was added to it. After 5 minutes the extract solution was added to it to terminate the reaction, and the protein fraction was extracted. To the extract was added an antibody against the human receptor type oncogene HER2 to precipitate the human receptor type oncogene HER2 protein by the reaction of immunoprecipitation. The precipitate was fractionated by the protein electrophoresis. The protein in the electrophoretic gel was transferred to a nylon filter. The filter was allowed to react with the phosphorylated tyrosine-specific antibody. The reaction product was fluorescence-labeled to expose a photofilm. The intensity of the exposure on the photofilm was quantitated by an image-analyzing apparatus. The proportion of the phosphorylation of HER2 tyrosine in the cells added with a compound solution of each concentration was calculated designating the phosphorylation of HER2 tyrosine in the heregulin-added cells as 100%.

The results are shown in [Table 2]. Compound 8 of the present invention has been shown to inhibit dose-dependently the phosphorylation reaction of the tyrosine residue in the receptor protein which was induced by activation of the receptor tyrosine kinase accompanied with the stimulation of the growth factors when human mammary cancer cells were stimulated by a growth factor heregulin.

TABLE 2

Inhibition of phosphorylation of receptor tyrosine residue

| Concentration of Compound 8 ($\mu M$) | 0 | 0.4 | 1.6 | 6.3 | 25 |
|---|---|---|---|---|---|
| Phosphorylation of the tyrosine residue (%) | 100 | 62 | 52 | 33 | 20 |

Test Example 3

Inhibition of Phosphorylation of Receptor Tyrosine in Human Breast Cancer Cells (2)

Human breast cancer cell line MCF-7 was used. 1,000 $\mu l$ of the cell suspension (250,000 cells) was seeded in each well of the 24-well plates. The culture were incubated at 37° C. in a 5% carbon dioxide gas incubator. On the next day, 100 $\mu l$ of the 10-fold serial dilution of each compound solution was added to each well and, 2 hours later, 0.5 $\mu g/ml$ of heregulin was added to it. After 5 minutes the extract solution was added to it to terminate the reaction, and the protein fraction was extracted. The protein was fractionated by the protein electrophoresis. The protein in the electrophoretic gel was transferred to a nylon filter. The filter was allowed to react with the phosphorylated tyrosine-specific antibody. The reaction product was fluorescence-labeled to expose a photofilm. The intensity of the exposure on the photofilm was quantitated by an image-analyzing apparatus. The proportion of the phosphorylation of HER2 tyrosine in the cells added with a compound solution of each concentration was calculated designating the phosphorylation of HER2 tyrosine in the heregulin-added cells as 100%.

The results are shown in [Table 3]. Compound (I) of the present invention has been shown to inhibit dose-dependently the phosphorylation reaction of the tyrosine residue in the receptor protein which was induced by activation of the receptor tyrosine kinase accompanied with the stimulation of the growth factors when human mammary cancer cells were stimulated by a growth factor heregulin.

TABLE 3

Phosphorylation of receptor tyrosine residue (%)

| Concentration of Compounds ($\mu M$) | 0 | 0.4 | 1.6 | 6.3 | 25 |
|---|---|---|---|---|---|
| Compound 8 | 100 | 67 | 41 | 32 | 30 |
| Compound 72 | 100 | 96 | 48 | 19 | 7 |
| Compound 80 | 100 | 46 | 40 | 34 | |
| Compound 94 | 100 | 93 | 86 | 45 | 25 |
| Compound 109 | 100 | 92 | 89 | 43 | 31 |

Test Example 4

In vitro Inhibition of Cell Proliferation (1)

100 $\mu l$ (containing 2,000 cells) of a cell suspension of human breast cancer cell line MDA-MB-453 was seeded in each well of the 96-well microtiter plates. The cultures were incubated at 37° C. in a 5% carbon dioxide gas incubator. On the next day, 100 $\mu l$ of the 2-fold serial dilution of each compound solution was added to each well and the mixtures were cultured for 3 days. The solution containing the compound was removed and the cells were washed with water. To the cells was added a 0.4% (W/V) dye SRB (dissolved in 1% acetic acid) solution to fix and stain the cell protein (Skehan P. et al., Journal of the National Cancer Institute Vol.82, pp.1107–1112, 1990). The dye solution was removed and the fixed and stained cell protein was washed. The protein-bound dye was extracted with 200 μl of 10 mM Tris buffer. The optical density of the extracted dye was determined at the wavelength of 540 nm to estimate the quantity of the cells in terms of the protein quantity. Designating the protein quantity in the control to which no compound solution was added as 100%, the proportion of the residual protein quantity in each treated group was calculated, and $IC_{50}$, which was concentration of the compound required to inhibit the residual protein quantity to 50% the quantity of the control, was calculated.

The results are shown in [Table 4].

TABLE 4

Inhibition of cell proliferation

| Compound | $IC_{50}$ (μM) Breast cancer MDA-MB-453 |
|---|---|
| 2 | 0.66 |
| 8 | 0.25 |

Test Example 5

In vitro Inhibition of Cell Proliferation (2)

100 μl (containing 2,000 cells) of a cell suspension of human breast cancer cell line MDA-MB-453 was seeded in each well of the 96-well microtiter plates. The cultures were incubated at 37° C. in a 5% carbon dioxide gas incubator. On the next day, 100 μl of the 2-fold serial dilution of each compound solution was added to each well and the mixtures were cultured for 3 days. The solution containing the compound was removed and the cells were washed with water. To the cells was added a 0.4% (W/V) dye SRB (dissolved in 1% acetic acid) solution to fix and stain the cell protein (Skehan P. et al., Journal of the National Cancer Institute Vol.82, pp.1107–1112, 1990). The dye solution was removed and the fixed and stained cell protein was washed. The protein-bound dye was extracted with 200 μl of 10 mM Tris buffer. The optical density of the extracted dye was determined at the wavelength of 540 nm to estimate the quantity of the cells in terms of the protein quantity. Designating the protein quantity in the control to which no compound solution was added as 100%, the proportion of the residual protein quantity in each treated group was calculated, and $IC_{50}$, which was concentration of the compound required to inhibit the residual protein quantity to 50% the quantity of the control, was calculated.

The results are shown in [Table 5].

TABLE 5

Inhibition of cell proliferation

| Compound | $IC_{50}$ (μM) Breast cancer MDA-MB-453 |
|---|---|
| 72 | 1.7 |
| 80 | 0.09 |
| 94 | 4.8 |
| 109 | 2.5 |

Test Example 6

Selective in vitro Inhibition of Breast Cancer Cell Growth

100 μl (containing 2,000 cells) of a cell suspension of various human breast cancer cell lines shown in [Table 6] was seeded in each well of the 96-well microtiter plates. The cells were incubated at 37° C. in a 5% carbon dioxide gas incubator. Next day, 100 μl of a 2 fold serial dilution of a compound solution was added to each well. The cultures were incubated for 3 days. The solution containing the compound was removed and the cells were washed with water. To the cells was added a 0.4% (V/W) dye SRB (dissolved in 1% acetic acid) solution to fix and stain the cell protein. The dye solution was removed and the fixed and stained cell protein was washed. The protein-bound dye was extracted with 200 μl of 10 mM Tris buffer. The optical density of the extracted dye was determined at the wavelength of 540 nm to estimate the quantity of the cells in terms of the protein quantity. Designating the protein quantity in the control to which no compound solution was added as 100%, the proportion of the residual protein quantity in each treated group was calculated, and $IC_{50}$, which was the concentration of the compound required to inhibit the residual protein quantity to 50% the quantity of the control, was calculated.

The results are shown in [Table 6]. Compound 8 of the present invention has been shown to inhibit specifically the cell growth of human mammary cancer cell line.

TABLE 6

Inhibition of cell proliferation of various cell lines

| Cancer | Cell lines | $IC_{50}$ for Compound 8 (μM) |
|---|---|---|
| Mammary cancer | MDA-MB-453 | 0.25 |
|  | MDA-MB-468 | 0.52 |
|  | BT-20 | 0.52 |
|  | BT-474 | 0.29 |
|  | SKBR3 | 1.0 |
|  | T-47D | 0.57 |
| Pancreatic cancer | ASPC-1 | 2.5 |
| Epidermal cancer | HSC-1 | 2.1 |
| Large intestinal cancer | WiDr | 2.1 |
| Normal | MRC5 | 15 |

Test Example 7

Selective in vitro Inhibition of Breast Cancer and Prostate Cancer Cell Growth

100 μl (containing 2,000 cells) of a cell suspension of various human cancer cell lines shown in [Table 7] was seeded in each well of the 96-well microtiter plates. The cells were incubated at 37° C. in a 5% carbon dioxide gas incubator. Next day, 100 μl of a 2 fold serial dilution of a compound solution was added to each well. The cultures were incubated for 3 days. The solution containing the compound was removed and the cells were washed with water. To the cells was added a 0.4% (V/W) dye SRB (dissolved in 1% acetic acid) solution to fix and stain the cell protein. The dye solution was removed and the fixed and stained cell protein was washed. The protein-bound dye was extracted with 200 μl of 10 mM Tris buffer. The optical density of the extracted dye was determined at the wavelength of 540 nm to estimate the quantity of the cells in terms of the protein quantity. Designating the protein quantity in the control to which no compound solution was added as 100%, the proportion of the residual protein quantity in each treated group was calculated, and $IC_{50}$, which was the concentration of the compound required to inhibit the residual protein quantity to 50% the quantity of the control, was calculated.

The results are shown in [Table 7]. Compound (I) of the present invention has been shown to inhibit specifically the cell growth of human mammary cancer cell line.

TABLE 7

Inhibition of cell proliferation of various cell lines

| Cancer | Cell lines | IC$_{50}$ for Compounds ($\mu$M) | | | |
|---|---|---|---|---|---|
| | | 72 | 80 | 94 | 109 |
| Breast cancer | MDA-MB-453 | 1.7 | 0.09 | 4.8 | 2.5 |
| | T-47D | 3.5 | | | |
| | MCF-7 | 0.62 | 0.01 | 1.1 | 0.19 |
| Prostate cancer | LNCaP | 7.9 | 1.6 | 5.6 | 11 |
| | PC3 | 9.5 | 6.5 | 15 | 16 |
| Normal | MRC5 | >25 | >25 | >25 | >25 |

As seen in Tables 1, 2, 3, 4, 5, 6 and 7, the compounds of the present invention have been shown to inhibit growth factor stimulated activation of tyrosine kinases in the receptor. They have no adverse effects on the proliferation of normal cells and inhibit the proliferation of tumor cells, especially of mammary and prostate cancer cells.

Test Example 8

In vivo Mammary Cancer Inhibiting Effect (1)

5,000,000 cells of human breast cancer cell line, MDA-MB-453, were suspended in a gelmatrix solution. The suspension was subcutaneously implanted at the breast in 7-week-old female Balb/C strain athymic nude mice (Friedman R. et al., Proceedings of the National Academy of Sciences of the U.S.A. Vol. 87, pp.6698–6702, 1990). Twelve days after the implantation, the diameters of tumors were determined. For the experiment were used 5 mice per group with similar tumor size. Compound 8 of the present invention was suspended in a 5% gum arabic solution (physiological saline) and administered orally twice daily in dose of 30 mg/kg body weight for 10 days, or 2 cycle oral administrations consisting of 45 mg/kg body weight twice daily for 3 days and no treatment for 3 days were performed. On the day when the dosing was ended, the diameters of tumors were measured. Tumor volume was calculated by the following formula: volume of tumor=longest diameter× shortest diameter×shortest diameter×½. The growth rate of tumors was obtained as the proportion to the volume of tumor in the control animals in which only the gum arabic solution was administered. The body weights of mice administered with Compound 8 of the present invention were measured during the experiment to observe no decrease.

The results are shown in [Table 8].

TABLE 8

Inhibition of athymic nude mice implanted cancer growth

| Dose of compound (mg/kg/day) | Tumor growth rate (%) |
|---|---|
| 0 | 100 |
| 60 | 71 |
| 90 | 46 |

Compound 8 of the present invention inhibited dose-dependently the growth of human breast cancer implanted to athymic nude mice.

Test Example 9

In vivo Mammary Cancer Inhibiting Effect (2)

5,000,000 cells of human breast cancer cell line, MDA-MB-453, were suspended in a gelmatrix solution. The suspension was subcutaneously implanted at the breast in 7-week-old female Balb/C strain athymic nude mice (Friedman R. et al., Proceedings of the National Academy of Sciences of the U.S.A. Vol. 87, pp.6698–6702, 1990). Twelve days after the implantation, the diameters of tumors were determined. For the experiment were used 5 mice per group with similar tumor size. Compound 72 or 109 of the present invention was suspended in a 5% gum arabic solution (physiological saline) and administered orally twice daily in dose of 60 mg/kg or 90 mg/kg body weight for 10 days. On the day when the dosing was ended, the diameters of tumors were measured. Tumor volume was calculated by the following formula: volume of tumor=longest diameter× shortest diameter×shortest diameter×½. The growth rate of tumors was obtained as the proportion of the gained tumor volume which was substracted the initial volume from the final volume in the treated animals to the gained tumor volume which was substracted the initial volume from the final volume in the control animals. The body weights of mice administered with compounds of the present invention were measured during the experiment to observe no decrease.

The results are shown in [Table 9].

TABLE 9

Inhibition of athymic nude mice implanted cancer growth

| Compound | Dose (mg/kg/day) | Tumor growth rate (%) |
|---|---|---|
| 72 | 120 | 84 |
| | 180 | 71 |
| 109 | 120 | 35 |

Compounds of the present invention inhibited dose-dependently the growth of human breast cancer implanted to athymic nude mice.

Test Example 10

In vivo Inhibition of Prostate Cancer (1)

5,000,000 cells of human prostatic cancer cell line, LNCaP, were suspended in a gelmatrix solution and implanted subcutaneously at the breast in 8-week old male Balb/C-strain athymic nude mice (Friedman R. et al., Proceedings of the National Academy of Sciences of the U.S.A. Vol. 87, pp.6698–6702, 1990). 42 days (in the case of compound 72) or 57 days (in the case of compound 109) after the implantation, the diameters of tumors were measured. Five mice per group with similar tumor size were used for the experiment. Compounds 72 or 109 of the present invention was suspended in a 5% gum arabic solution (physiological saline) and administered orally twice daily in a dose of 60 mg/kg and 90 mg/kg body weight for 10 days. After the completion of the dosing, the diameters of tumor were measured. The tumor volume was calculated by the following formula: volume of tumor=longest diameter× shortest diameter×shortest diameter×½. The growth rate of tumors was obtained as the proportion of the gained tumor volume which was substracted the initial volume from the final volume in the treated animals to the gained tumor volume which was subtracted the initial volume from the final volume in the control animals. The body weights of mice administered with compounds of the present invention were measured during the experiment to observe no decrease.

The results are shown in [Table 10].

TABLE 10

Inhibition of athymic nude mice implanted cancer growth

| Compound | Dose (mg/kg/day) | Tumor growth rate (%) |
|---|---|---|
| 72 | 0 | 100 |
|  | 120 | 91 |
|  | 180 | 57 |
| 109 | 0 | 100 |
|  | 120 | 28 |

Compounds 72 and 109 of the present invention have the effect of inhibiting tumor growth of hormone dependent prostate cancer LNCaP.

Test Example 11

In vivo Inhibition of Prostate Cancer (2)

5,000,000 cells of human prostate cancer cell line, LNCaP, were suspended in a gelmatrix solution and implanted subcutaneously at the breast in 8-week old male Balb/C-strain athymic nude mice (Friedman R. et al., Proceedings of the National Academy of Sciences of the U.S.A. Vol. 87, pp.6698–6702, 1990). 33 days after the implantation, the diameters of tumors were measured. Five mice per group with similar tumor size were used for the experiment. Compound 8 of the present invention was suspended in a 5% gum arabic solution (physiological saline) and administered orally twice daily in a dose of 30 mg/kg body weight for 21 days. For another experiment, the mice were castrated 33 days after implantation of the cancer cell for observing the effect of hormone depletion on the prostate cancer growth. Furthermore, Compound 8 of the present invention was administered orally twice daily in a dose of 30 mg/kg body weight for 21 days to the castrated mice. After the completion of the dosing, the diameters of tumor were measured. The tumor volume was calculated by the following formula: volume of tumor=longest diameter× shortest diameter×shortest diameter×½. The growth rate of tumors was obtained as the proportion to the volume of tumor in the control animals in which only the gum arabic solution was administered. The body weights of mice administered with Compound 8 of the present invention were measured during the experiment to observe no decrease.

The results are shown in [Table 11].

TABLE 11

Inhibition of athymic nude mice implanted cancer growth

| Concentration of compound (mg/kg/day) | Tumor growth rate (%) |
|---|---|
| 0 | 100 |
| 60 | 80 |
| 0 (castrated group) | 69 |
| 60 (castrated group) | 55 |

Compound 8 of the present invention has the effect of inhibiting tumor growth of hormone dependent prostate cancer LNCaP. The tumor growth inhibiting effect of this compound was found to be further enhanced when the hormone levels were reduced by castration. Testectomy is widely practiced for treatment of patients with prostatic cancer. Also, hormone therapy such as treatment with an LH-RH antagonist is now practiced for the treatment. Therefore, the compounds of the present invention may offer a more effective therapeutic method for treatment of prostatic cancer by combination with these conventional therapeutic methods.

Formulation Example 1

(Dosage Per Tablet)

| (1) Compound of Working Example 8 | 10.0 mg |
| (2) Lactose | 60.0 mg |
| (3) Corn starch | 35.0 mg |
| (4) Gelatin | 3.0 mg |
| (5) Magnesium stearate | 2.0 mg |

A mixture of 10.0 mg of the compound of Working Example 8, 60.0 mg of lactose and 35.0 mg of corn starch was granulated, by using 0.03 ml of a 10 weight % aqueous solution of gelatin (3.0 mg. in terms of gelatin), through a sieve of 1 mm mesh. The granules were dried at 40° C., which were again subjected to sieving. The resulting granules were mixed with 2.0 mg of magnesium stearate, which was compressed. Thus-obtained core tablets was sugar-coated with a suspension consisting of sucrose, titanium dioxide, talc and gum arabica, followed by polishing with bee wax.

Formulation Example 2

(Dosage Per Tablet)

| (1) Compound of Working Example 8 | 10.0 mg |
| (2) Lactose | 70.0 mg |
| (3) Corn starch | 50.0 mg |
| (4) Soluble starch | 7.0 mg |
| (5) Magnesium stearate | 3.0 mg |

A mixture of 10.0 mg of the compound of Working Example 8 and 3.0 mg of magnesium stearate was granulated by using 0.07 ml of an aqueous solution of soluble starch (7.0 mg in terms of soluble starch) and dried, which was mixed with 70.0 mg of lactose and 50.0 mg of corn starch. The mixture was compressed to give a tablet.

Reference Example 1

To a suspension of lithium aluminum hydride (350 mg) in diethyl ether (10 ml) was added dropwise, at 0° C., a solution of ethyl 4-[4-[2-[(E)-2-phenylethenyl]-4-oxazolylmethoxy]phenyl]butyrate (3.00 g) in diethyl ether (10 ml)—tetrahydrofuran (10 ml). The mixture was stirred at 0° C. for one hour and at room temperature for further one hour, followed by addition of water. The mixture was acidified with 2N hydrochloric acid and extracted with ethyl acetate. The ethyl acetate layer was washed with water, dried (MgSO$_4$), and concentrated under reduced pressure. The residue was subjected to a silica gel column chromatography. From the fraction eluted with ethyl acetate-hexane (1:1,v/v), 4-[4-[2-[(E)-2-phenylethenyl]-4-oxazolylmethoxy]phenyl]butanol (2.00 g, 74%) was obtained. Recrystallization from ethyl acetate-hexane afforded colorless needles, mp 90–91° C.

Reference Example 2

In substantially the same manner as in Reference Example 1, ethyl 3-[4-[2-[(E)-2-phenylethenyl]-4-oxazolylmethoxy]phenyl]propionate was reduced to give 3-[4-[2-[(E)-2-phenylethenyl]-4-oxazolylmethoxy]phenyl] propanol. The yield was 94%. Recrystallization from ethyl acetate-hexane gave colorless needles, mp 95–96° C.

Reference Example 3

In substantially the same manner as in Reference Example 1, methyl 4-[2-((E)-2-phenylethenyl]-4-oxazolylmethoxy]phenylacetate was reduced to give 2-[4-[2-[(E)-2-phenylethenyl]-4-oxazolylmethoxy]phenyl]ethanol. The yield was 50%. Recrystallization from acetone-isopropyl ether gave colorless prisms, mp 123–124° C.

Reference Example 4

In substantially the same manner as in Reference Example 1, ethyl 5-[4-[2-[(E)-2-phenylethenyl]-4-oxazolylmethoxy]phenyl]pentanoate was reduced to give 5-[4-[2-[(E)-2-phenylethenyl]-4-oxazolylmethoxy]phenyl]pentanol. The yield was 68%. Recrystallization from ethyl acetate-hexane gave colorless prisms, mp 93–94° C.

Reference Example 5

In substantially the same manner as in Reference Example 1, ethyl 6-[4-[2-[(E)-2-phenylethenyl]-4-oxazolylmethoxy]phenyl]hexanoate was reduced to give 6-[4-[2-[(E)-2-phenylethenyl]-4-oxazolylmethoxy]phenyl]hexanol. The yield was 60%. Recrystallization from ethyl acetate-hexane gave colorless prisms, mp 94–95° C.

Reference Example 6

In substantially the same manner as in Reference Example 1, ethyl 3-[3-[2-[(E)-2-phenylethenyl]-4-oxazolyl methoxy]phenyl]propionate was subjected to reduction to give 3-[3-[2-[(E)-2-phenylethenyl]-4-oxazolylmethoxy]phenyl] propanol. The yield was 82%. Recrystallization from ethyl acetate-hexane gave colorless prisms, mp 57–58° C.

Reference Example 7

In substantially the same manner as in Reference Example 1, ethyl 3-[2-[2-[(E)-2-phenylethenyl]-4-oxazolylmethoxy]phenyl]propionate was reduced to give 3-[2-[2-[(E)-2-phenylethenyl]-4-oxazolylmethoxy]phenyl]propanol. The yield was 33%. Recrystallization from ethyl acetate-hexane gave colorless prisms, mp 76–77° C.

Reference Example 8

In substantially the same manner as in Reference Example 1, ethyl 3-[3-methoxy-4-[2-[(E)-2-phenylethenyl]-4-oxazolylmethoxy]phenyl]propionate was reduced to give 3-[3-methoxy-4-[2-[(E)-2-phenylethenyl]-4-oxazolylmethoxy]phenyl]propanol. The yield was 68%. Recrystallization from ethyl acetate-hexane gave colorless needles, mp 95–96° C.

Reference Example 9

In substantially the same manner as in Reference Example 1, ethyl 3-[4-methoxy-3-[2-[(E)-2-phenylethenyl]-4-oxazolylmethoxy]phenyl]propionate was reduced to give 3-[4-methoxy-3-[2-[(E)-2-phenylethenyl]-4-oxazolylmethoxy]phenyl]propanol. The yield was 60%. Recrystallization from ethyl acetate-hexane gave colorless needles, mp 126–128° C.

Reference Example 10

In substantially the same manner as in Reference Example 1, ethyl 4-[4-benzyloxyphenyl)butyrate was reduced to give 4-(4-benzyloxyphenyl) butanol. The yield was 87%. Recrystallization from isopropyl ether gave colorless leaflets, mp 59–60° C.

Reference Example 11

In substantially the same manner as in Reference Example 1, ethyl 3-(4-benzyloxyphenyl)propionate was reduced to give 3-(4-benzyloxyphenyl) propanol. The yield was 95%. Recrystallization from ethyl acetate-hexane gave colorless prisms, mp 63–64° C.

Reference Example 12

To a mixture of 4-[4-[2-(E)-2-phenylethenyl]-4-oxazolylmethoxy]phenyl]butanol (1.74 g), triethylamine (660 mg) and ethyl acetate (50 ml) was added, at 0° C., methanesulfonyl chloride (745 mg). The mixture was stirred for two hours at room temperature. To the reaction mixture were supplemented triethylamine (350 mg) and methanesulfonyl chloride (405 mg). The mixture was stirred at room temperature overnight. The reaction mixture was poured into water and extracted with ethyl acetate. The ethyl acetate layer was washed successively with saturated aqueous sodium hydrogencarbonate, 1N hydrochloric acid and brine, dried (MgSO$_4$), and concentrated under reduced pressure to give 4-[4-[2-[(E)-2-phenylethenyl]-4-oxazolylmethoxy]phenyl]butyl methanesulfonate (2.00 g, 94%). Recrystallization from ethyl acetate-hexane gave colorless prisms, mp 82–83° C.

Reference Example 13

In substantially the same manner as in Reference Example 12, 3-[4-[2-[(E)-2-phenylethenyl]-4-oxazolylmethoxy]phenyl]propanol was allowed to react with methanesulfonyl chloride to give 3-[4-[2-[(E)-2-phenylethenyl]-4-oxazolylmethoxy]phenyl]propyl methanesulfonate. The yield was 92%. Recrystallization from ethyl acetate-hexane gave colorless prisms, mp 111–112° C.

Reference Example 14

In substantially the same manner as in Reference Example 12, 2-[4-[2-[(E)-2-phenylethenyl]-4-oxazolylmethoxy]phenyl]ethanol was allowed to react with methanesulfonyl chloride to give 2-[4-[2-[(E)-2-phenylethenyl]-4-oxazolylmethoxy]phenyl]ethyl methanesulfonate. The yield was 82%. Recrystallization from acetone-isopropyl ether gave colorless prisms, mp 121–122° C.

Reference Example 15

In substantially the same manner as in Reference Example 12, 5-[4-[2-[(E)-2-phenylethenyl]-4-oxazolylmethoxy]phenyl]pentanol was allowed to react with methanesulfonyl chloride to give 5-[4-[2-[(E)-2-phenylethenyl]-4-oxazolylmethoxy]phenyl]pentyl methanesulfonate. The yield was 96%. Recrystallization from ethyl acetate-hexane gave colorless prisms, mp 105–106° C.

Reference Example 16

In substantially the same manner as in Reference Example 12, 6-[4-[2-[(E)-2-phenylethenyl]-4-oxazolyl methoxy]phenyl]hexanol was allowed to react with methanesulfonyl chloride to give 6-[4-[2-[(E)-2-phenyl ethenyl]-4-oxazolylmethoxy]phenyl]hexyl methanesulfonate. The yield was 97%. Recrystallization from ethyl acetate-hexane gave colorless prisms, mp 88–89° C.

Reference Example 17

In substantially the same manner as in Reference Example 12, 3-[3-[2-[(E)-2-phenylethenyl]-4-oxazolylmethoxy]phenyl]propanol was allowed to react with methanesulfonyl chloride to give 3-[3-[2-[(E)-2-phenylethenyl]-4-oxazolylmethoxy]phenyl]propyl methanesulfonate. The yield was 78%. Recrystallization from ethyl acetate-hexane gave colorless prisms, mp 75–76° C.

Reference Example 18

In substantially the same manner as in Reference Example 12, 3-[2-[2-[(E)-2-phenylethenyl]-4-oxazolylmethoxy]phenyl]propanol was allowed to react with methanesulfonyl chloride to give 3-[2-[2-[(E)-2-phenylethenyl]-4-oxazolylmethoxy]phenyl]propyl methanesulfonate. The yield was 95%. Recrystallization from ethyl acetate-hexane gave colorless prisms, mp 93–94° C.

Reference Example 19

In substantially the same manner as in Reference Example 12, 3-[3-methoxy-4-[2-[(E)-2-phenylethenyl]-4-oxazolylmethoxy]phenyl]propanol was allowed to react with methanesulfonyl chloride to give 3-[3-methoxy-4-[2-[(E)-2-phenylethenyl]-4-oxazolylmethoxy]phenyl]propyl methanesulfonate. The yield was 99%. Recrystallization from ethyl acetate-hexane gave colorless prisms, mp 130–131° C.

Reference Example 20

In substantially the same manner as in Reference Example 12, 3-[4-methoxy-3-[2-[(E)-2-phenylethenyl]-4-oxazolylmethoxy]phenyl]propanol was allowed to react with methanesulfonyl chloride to give 3-[4-methoxy-3-[2-[(E)-2-phenylethenyl]-4-oxazolylmethoxy]phenyl]propyl methanesulfonate. The yield was 94%. Recrystallization from ethyl acetate-hexane gave pale yellow needles, mp 112–113° C.

Reference Example 21

In substantially the same manner as in Reference Example 12, 3-(4-benzyloxyphenyl)propanol was allowed to react with methanesulfonyl chloride to give 3-(4-benzyloxyphenyl)propyl methanesulfonate. The yield was 98%. Recrystallization from ethyl acetate-hexane gave colorless prisms, mp 74–75° C.

Reference Example 22

A mixture of 3-[4-methoxy-3-[2-[(E)-2-phenylethenyl]-4-oxazolylmethoxy]phenyl]propyl methanesulfonate (900 mg), sodium iodide (3.00 g) and acetone (20 ml) was heated for one hour under reflux. The reaction mixture was poured into water and extracted with ethyl acetate. The ethyl acetate layer was washed with water, dried ($MgSO_4$), and concentrated under reduced pressure. The residue was subjected to a silica gel column chromatography. From the fraction eluted with ethyl acetate-hexane (1:4, v/v), 4-[3-(3-iodopropyl)-2-methoxyphenoxymethyl]-2-[(E)-2-phenylethenyl]oxazole (905 mg, 95%) was obtained. Recrystallization from ethyl acetate-hexane gave colorless needles, mp 103–104° C.

Reference Example 23

A mixture of 4-[2-[(E)-2-phenylethenyl]-4-oxazolyl methoxy]benzaldehyde (5.00 g), sodium borohydride (620 mg), tetrahydrofuran (50 ml) and ethanol (50 ml) was stirred for 16 hours at room temperature. The reaction mixture was poured into water and acidified with 2N hydrochloric acid. The resulting precipitate was collected by filtration and dried, which was suspended in chloroform (50 ml). To the suspension was added thionyl chloride (2.00 g). The mixture was stirred for one hour at room temperature. The reaction mixture was concentrated, to which was added ethyl acetate, followed by washing with saturated aqueous sodium hydrogencarbonate and water. The ethyl acetate layer was separated and dried ($MgSO_4$). The solvent was distilled off to leave crystals, followed by recrystallization from chloroform-isopropyl ether to give 4-(4-chloromethylphenoxymethyl)-2-[(E)-2-phenylethenyl]oxazole (3.25 g, 61%) as colorless prisms, mp 116–117° C.

Reference Example 24

A solution of aluminum chloride (7.07 g) in diethyl ether (90 ml) was added dropwise, at 0° C., to a suspension of lithium aluminum hydride (7.59 g) in diethyl ether (300 ml). The mixture was stirred for 15 minutes, to which was added dropwise, at 0° C., a solution of ethyl 4-benzyloxy-3-methoxycinnamate (50,0 g) in diethyl ether (250 ml). The mixture was stirred for one hour at room temperature, to which was added water (200 ml), then, was carefully added 5N sulfuric acid (280 ml) at 0° C. The diethyl ether layer was taken. The aqueous layer was extracted with ethyl acetate. Organic layers were combined, washed with water, dried ($MgSO_4$), and concentrated under reduced pressure. The residue was subjected to a silica gel column chromatography. From the fraction eluted with ethyl acetate-hexane (3:2, v/v), 3-(4-benzyloxy-3-methoxyphenyl)-2-propen-1-ol (34.2 g, 79%) was obtained. Recrystallization from ethyl acetate-hexane gave colorless prisms, mp 81–82° C.

Reference Example 25

To a solution of 4-(4-benzyloxyphenyl)butanol (3.55 g), tributyl phosphine (6.84 g) and 1,2,4-triazole (1.86 g) in tetrahydrofuran (75 ml) was added dropwise, at room temperature, diethyl azodicarboxylate (40% toluene solution, 11.8 g). The mixture was heated for two hours under reflux. The reaction mixture was poured into water and extracted with ethyl acetate. The ethyl acetate layer was washed with water, dried ($MgSO_4$), and concentrated under reduced pressure. The residue was subjected to a silica gel column chromatography. From the fraction eluted with ethyl acetate-hexane (1:2, v/v), 1-[4-(4-benzyloxyphenyl)butyl]-1,2,4-triazole (3.45 g, 83%) was obtained. Recrystallization from isopropyl ether gave colorless prisms, mp 68–69° C.

Reference Example 26

In substantially the same manner as in Reference Example 25, 3-(4-benzyloxy-3-methoxyphenyl)-2-propen-1-ol was allowed to react with 1,2,4-triazole to give 1-[3-(4-benzyloxy-3-methoxyphenyl)-2-propenyl]-1,2,4-triazole. The yield was 34%. Recrystallization from ethyl acetate-hexane gave colorless prisms, mp 70–72° C.

Reference Example 27

A mixture of 3-(4-benzyloxyphenyl)propyl methanesulfonate (55.0 g), imidazole (17.6 g), potassium carbonate (35.7 g) and N,N-dimethylformamide (500 ml) was stirred for 6 hours at 80° C. The reaction mixture was poured into water and extracted with ethyl acetate. The ethyl acetate layer was washed with water, dried ($MgSO_4$), and concentrated under reduced pressure to give 1-[3-(4-benzyloxyphenyl)propyl]imidazole (34.7 g, 69%). Recrystallization from ethyl acetate-hexane gave colorless needles, mp 80–81° C.

Reference Example 28

A mixture of 1-[4-(4-benzyloxyphenyl)butyl]-1,2,4-triazole (3.15 g), palladium-carbon (5%, 3.0 g) and ethanol (50 ml) was subjected to catalytic hydrogenation under atmospheric pressure at room temperature. The catalyst was filtered off, and the filtrate was concentrated. The residue was subjected to a silica gel column chromatography. The crystalline product obtained from the fraction eluted with tetrahydrofuran-hexane (1:1, v/v) was recrystallized from ethyl acetate-hexane to give 1-[4-(4-hydroxyphenyl)butyl]-1,2,4-triazole (1.22 g, 55%) as colorless prisms, mp 135–136° C.

Reference Example 29

In substantially the same manner as in Reference Example 28, 1-[3-(4-benzyloxy-3-methoxyphenyl)-2-propenyl]-1,2,4-triazole was subjected to catalytic hydrogenation to give 1-[3-(4-hydroxy-3-methoxyphenyl)propyl]-1,2,4-triazole. The yield was 78%. Recrystallization from ethyl acetate-hexane gave colorless prisms, mp 97–98° C.

Reference Example 30

In substantially the same manner as in Reference Example 28, 1-[3-(4-benzyloxyphenyl)propyl]imidazole was subjected to catalytic hydrogenation to give 1-[3-(4-hydroxyphenyl)propyl]imidazole. The yield was 81%. Recrystallization from ethanol gave colorless prisms, mp 158–160° C.

Reference Example 31

A mixture of cinnamamide (25.3 g) and 1,3-dichloroacetone (20.9 g) was stirred for one hour at 130° C. The reaction mixture was diluted with water, neutralized with potassium carbonate, and extracted with ethyl acetate. The ethyl acetate layer was washed with water, dried ($MgSO_4$), and concentrated under reduced pressure. The residue was subjected to a silica gel column chromatography. From the fraction eluted with diethyl ether-hexane, 4-chloromethyl-2-[(E)-2-phenylethenyl]oxazole (16.9 g, 47%) was obtained. Recrystallization from diethyl ether-hexane gave colorless needles, mp 72–73° C.

Reference Example 32

In substantially the same manner as in Reference Example 31, 3,4-dihydro-2-naphthalenecarboxamide was allowed to react with 1,3-dichloroacetone to give 4-chloromethyl-2-(3,4-dihydro-2-naphthyl)oxazole. The yield was 60%. Recrystallization from isopropyl ether gave colorless prisms, mp 73–74° C.

Reference Example 33

In substantially the same manner as in Reference Example 31, phenylacetamide was allowed to react with 1,3-dichloroacetone to give 2-benzyl-4-chloromethyl oxazole. The yield was 33%. Recrystallization from hexane gave colorless prisms, mp 31–32° C.

Reference Example 34

In substantially the same manner as in Reference Example 31, isobutyramide was allowed to react with 1,3-dichloroacetone to give 4-chloromethyl-2-isopropyl oxazole as an oily product. The yield was 6.2%.

NMR (δ ppm in $CDCl_3$): 1.35(6H,d,J=7 Hz), 3.0–3.15 (1H,m), 4.50(2H,s), 7.55(1H,s).

Reference Example 35

In substantially the same manner as in Reference Example 31, 4-chlorobenzamide was allowed to react with 1,3-dichloroacetone to give 4-chloromethyl-2-(4-chlorophenyl) oxazole. The yield was 54%. Recrystallization from isopropyl ether gave colorless needles, mp 97–98° C.

Reference Example 36

In substantially the same manner as in Reference Example 31, 4-benzyloxybenzamide was allowed to react with 1,3-dichloroacetone to give 2-(4-benzyloxyphenyl)-4-chloromethyloxazole. The yield was 33%. Recrystallization from ethyl acetate-hexane gave colorless prisms, mp 119–120° C.

Reference Example 37

In substantially the same manner as in Reference Example 31, 3-benzyloxybenzamide was allowed to react with 1,3-dichloroacetone to give 2-(3-benzyloxyphenyl)-4-chloromethyloxazole. The yield was 26%. Recrystallization from ethyl acetate-hexane gave colorless prisms, mp 49–50° C.

Reference Example 38

In substantially the same manner as in Reference Example 31, 3,5-dimethoxybenzamide was allowed to react with 1,3-dichloroacetone to give 4-chloromethyl-2-(3,5-dimethoxyphenyl)oxazole. The yield was 59%. Recrystallization from ethyl acetate-hexane gave colorless needles, mp 85–86° C.

Reference Example 39

In substantially the same manner as in Reference Example 31, 3,5-dimethylbenzamide was allowed to react with 1,3-dichloroacetone to give 4-chloromethyl-2-(3,5-dimethylphenyl)oxazole. The yield was 52%. Recrystallization from isopropyl ether gave colorless needles, mp 76–77° C.

Reference Example 40

In substantially the same manner as in Reference Example 31, 4-cyanobenzamide was allowed to react with 1,3-dichloroacetone to give 4-chloromethyl-2-(4-cyanophenyl) oxazole. The yield was 41%. Recrystallization form ethyl acetate-hexane gave colorless prisms, mp 134–135° C.

Reference Example 41

In substantially the same manner as in Reference Example 31, cyclohexanecarboxamide was allowed to react with 1,3-dichloroacetone to give 4-chloromethyl-2-cyclohexyloxazole as an oily product. The yield was 2.7%.

NMR (δ ppm in CDCl$_3$): 1.2–1.9(8H,m), 2.0–2.15(2H, m), 2.6–2.95(1H,m), 4.49(2H,s), 7.54(1H,s).

Reference Example 42

A mixture of thiocinnamamide (11.7 g), 1,3-dichloroacetone (9.10 g) and ethanol (145 ml) was heated for one hour under reflux. The reaction mixture was poured onto ice-water, neutralized with potassium carbonate, and extracted with ethyl acetate. The ethyl acetate layer was washed with water, dried (MgSO$_4$), and concentrated under reduced pressure. The residue was subjected to a silica gel column chromatography. From the fraction eluted with diethyl ether-hexane (1:5, v/v), 4-chloromethyl-2-[(E)-2-phenylethenyl]thiazole (9.40 g, 66%) was obtained. Recrystallization from diethyl ether-hexane gave colorless plates, mp 88–89° C.

Reference Example 43

In substantially the same manner as in Reference Example 31, 2-naphthalenecarboxamide was allowed to react with 1,3-dichloroacetone to give 4-chloromethyl-2-(2-naphthyl)oxazole. The yield was 68%. Recrystallization from ethyl acetate-hexane gave colorless prisms, mp 116–117° C.

Reference Example 44

In substantially the same manner as in Reference Example 31, 2-benzo[b]thiophenecarboxamide was allowed to react with 1,3-dichloroacetone to give 2-(2-benzo[b]thienyl)-4-chloromethyloxazole. The yield was 33%. Recrystallization from ethyl acetate-hexane gave colorless prisms, mp 150–151° C.

Reference Example 45

In substantially the same manner as in Reference Example 31, ethyl succinamidate was allowed to react with 1,3-dichloroacetone to give ethyl 4-chloromethyl-2-oxazolepropionate as an oily product. The yield was 7.2%.

NMR (δ ppm in CDCl$_3$): 1.26(3H,t,J=7 Hz), 2.81(2H,t, J=7.5 Hz), 3.09(2H,t,J=7.5 Hz), 4.19(2H,q,J=7 Hz), 4.48 (2H,s), 7.56(1H,s).

Reference Example 46

In substantially the same manner as in Reference Example 31, 3,3-diphenylpropenamide was allowed to react with 1,3-dichloroacetone to give 2-(2,2-diphenylethenyl)-4-chloromethyloxazole. The yield was 49%. Recrystallization from ethyl acetate-hexane gave colorless prisms, mp 107–108° C.

Reference Example 47

A mixture of 2-thiophenecarboxamide (5.09 g) and 1,3-dichloroacetone (457 g) was stirred at 120° C. for 2 hours. The reaction mixture was poured into water, nautralized with potassium carbonate, and then extracted with ethyl acetate. The ethyl acetate layer was washed with water, dried (MgSO$_4$), and concentrated under reduced pressure. The residue was subjected to a silica gel column chromatography. From the fraction eluted with diethyl ether-hexane (1:9, v/v), 4-chloromethyl-2-(2-thienyl)oxazole (4.09 g, 57%) was obtained. Recrystallization from isopropylether gave colorless needles, mp 59–59° C.

Reference Example 48

In substantially the same manner as in Reference Example 47, crotonamide was allowed to react with 1,3-dichloroacetone to give 4-chloromethyl-2-(1-propenyl) oxazole. The yield is 10%. Oily substance.

NMR(δ ppm in CDCl$_3$): 1.94(3H,dd,J=6.6,1.6 Hz), 4.50 (2H,s), 6.29(1H,dd,J=15.8,1.6 Hz), 6.76(1H,dq,J=15.8,6.6 Hz), 7.53(1H,s).

Reference Example 49

In substantially the same manner as in Reference Example 47, 3-cyclohexylpropeneamide was allowed to react with 1,3-dichloroacetone to give 4-chloromethyl-2-[(E)-2-cyclohexylethenyl]oxazole. The yield was 4.5%. Oily substance.

NMR (δ ppm in CDCl$_3$): 1.05–1.4(5H,m), 1.65–1.9(5H, m), 2.05–2.3(1H,m), 4.49(2H,s), 6.23(1H,d,J=16.2 Hz), 6.70(1H,dd,J=16.2,7 Hz), 7.53(1H,s).

Reference Example 50

In substantially the same manner as in Reference Example 47, 4-benzoylbenzamide was allowed to react with 1,3-dichloroacetone to give 2-(4-benzoylphenyl)-4-chloromethyloxazole. The yield was 46%. Recrystallization from ethyl acetate-hexane gave colorless prisms, mp 138–139° C.

Reference Example 51

In substantially the same manner as in Reference Example 47, 2-benzofurancarboxamide was allowed to react with 1,3-dichloroacetone to give 2-(2-benzofuranyl)-4-chloromethyloxazole. The yield was 30%. Recrystallization from ethyl acetate-hexane gave colorless needles, mp 133–134° C.

Reference Example 52

In substantially the same manner as in Reference Example 47, 9-fluorenone-2-carboxamide was allowed to react with 1,3-dichloroacetone to give 4-chloromethyl-2-(9-fluorenone-2-yl)oxazole. The yield was 18%. Recrystallization from ethyl acetate-hexane was yellow prisms, mp 188–189° C.

Reference Example 53

In substantially the same manner as in Reference Example 47, 9-fluorenylideneacetamide was allowed to react with 1,3-dichloroacetone to give 4-chloromethyl-2-(9-fluorenylidene)methyloxazole. The yield was 36%. Recrystallization from ethyl acetate-hexane gave yellow prisms, mp 175–176° C.

Reference Example 54

In substantially the same manner as in Reference Example 47, 5-methyl-2-thiophenecarboxamide was allowed to react with 1,3-dichloroacetone to give 4-chloromethyl-2-(5-methyl-2-thienyl)oxazole. The yield was 46%. Recrystallization from ethyl acetate-hexane gave colorless prisms, mp 84–85° C.

Reference Example 55

In substantially the same manner as in Reference Example 47, 5-chloro-2-thiophenecarboxamide was allowed to react with 1,3-dichloroacetone to give 4-chloromethyl-2-(5-chloro-2-thienyl)oxazole. The yield was 51%. Recrystallization from ethyl acetate-hexane gave colorless needles, mp 90–91° C.

Reference Example 56

In substantially the same manner as in Reference Example 47, 3-thiophenecarboxamide was allowed to react with 1,3- dichloroacetone to give 4-chloromethyl-2-(3-thienyl) oxazole. The yield was 50%. Recrystallization from ethyl acetate-hexane gave colorless needles, mp 91–92° C.

Reference Example 57

In substantially the same manner as in Reference Example 47, 2-furancarboxamide was aollowed to react with 1,3-dichloroacetone to give 4-chloromethyl-2-(2-furyl)oxazole. The yield was 47%. Oily substance.

NMR (δ ppm in $CDCl_3$): 4.56(2H,s), 6.54(1H,dd,J=3.5, 1.8 Hz), 7.06(1H,dd,J=3.5,0.6 Hz), 7.55–7.6(2H,m).

Reference Example 58

In substantially the same manner as in Reference Example 47, 2-phenyl-5-benzoxazolecarboxamide was allowed to react with 1,3-dichloroacetone to give 5-(4-chloromethyl-2-oxazolyl)-2-phenylbenzoxazole. The yield was 65%. Recrystallization from ethyl acetate-hexane gave brown needles, mp 194–195° C.

Reference Example 59

In substantially the same manner as in Reference Example 47, 3-methyl-2-thiophenecarboxamide was allowed to react with 1,3-dichloroacetone to give 4-chloromethyl-2-(3-methyl-2-thienyl)oxazole. The yield was 61%. Recrystallization from ethyl acetate-hexane gave colorless needles, mp 95–96° C.

Reference Example 60

In substantially the same manner as in Reference Example 47, 5-ethyl-2-thiophenecarboxamide was allowed to react with 1,3-dichloroacetone to give 4-chloromethyl-2-(5-ethyl-2-thienyl)oxazole. The yield was 54%.

NMR (δ ppm in $CDCl_3$): 1.34(3H,t,J=7.6 Hz), 2.89(2H, qd,J=7.6,1 Hz), 4.54(2H,d,J=0.8 Hz), 6.80(1H,dt,J=3.8,1 Hz), 7.51(1H,d,J=3.8 Hz), 7.61(1H,t,J=0.8 Hz).

Reference Example 61

In substantially the same manner as in Reference Example 47, 4,5,6,7-tetrahydro-2-benzothiophene carboxamide was allowed to react with 1,3-dichloroacetone to give 4-chloromethyl-2-(4,5,6,7-tetrahydro-2-benzothienyl) oxazole. The yield was 53%. Recrystallization from ethyl acetate-hexane gave colorless needles, mp 102–103° C.

Reference Example 62

In substantially the same manner as in Reference Example 47, 5-bromo-4-methyl-2-thiophenecarboxamide was allowed to react with 1,3-dichloroacetone to give 2-(5-bromo-4-methyl-2-thienyl)-4-chloromethyloxazole. The yield was 53%. Recrystallization from ethyl acetate-hexane gave clolorless prisms, mp 71–72° C.

Reference Example 63

In substantially the same manner as in Reference Example 47, 5-chloro-2-furancarboxamide was allowed to react with 1,3-dichloroacetone to give 2-(5-chloro-2-furyl)-4-chloromethyloxazole. The yield was 24%. Recrystallization from diethyl ether-hexane gave colorless prisms, mp 107–108° C.

Reference Example 64

In substantially the same manner as in Reference Example 47, 5-bromo-2-furancarboxamide was allowed to react with 1,3-dichloroacetone to give 2-(5-bromo-2-furyl)-4-chloromethyloxazole. The yield was 23%. Recrystallization from diethyl ether-hexane gave colorless needles, mp 90–92° C.

Reference Example 65

In substantially the same manner as in Reference Example 47, 5-methyl-2-furancarboxamide was allowed to react with 1,3-dichloroacetone to give 4-chloromethyl-2-(5-methyl-2-furyl)oxazole. The yield was 38%. Recrystallization from diethyl ether-hexane gave. Colorless needles, mp 93–94° C.

Reference Example 66

In substantially the same manner as in Reference Example 47, 3-chloro-2-thiophenecarboxamide was allowed to react with 1,3-dichloroacetone to give 4-chloromethyl-2-(3-chloro-2-thienyl)oxazole. The yield was 54%. Recrystallization from ethyl acetate-hexane gave colorless prisms, mp 84–85° C.

Reference Example 67

In substantially the same manner as in Reference Example 47, 4-chloro-2-thiophenecarboxamide was allowed to react with 1,3-dichloroacetone to give 4-chloromethyl-2-(4-chloro-2-thienyl)oxazole. The yield was 48%. Recrystallization from diethyl ether-hexane gave colorless needles, mp 72–73° C.

Reference Example 68

In substantially the same manner as in Reference Example 47, 5-methoxy-2-thiophenecarboxamide was allowed to react with 1,3-dichloroacetone to give 4-chloromethyl-2-(5-methoxy-2-thienyl)oxazole. The yield was 1.2%. Recrystallization from ethyl acetate-hexane gave colorless prisms, mp 64–65° C.

Reference Example 69

A mixture of 2-amino-4-phenylphenol (5.00 g), chloro-acetylchloride (3.35 g), triethylamine (3.00 g), pyridinium tosylate (2.24 g) and xylene (100 ml) was heated under reflux for 15 hours. To the reaction mixture was added ethyl acetate, washed with water, dried ($MgSO_4$), and concentrated under reduced pressure. The residue was subjected to a silica gel chromatography. From the fraction eluted with the ethyl acetate-hexane (1:9, v/v), crystals of 2-chloromethyl-5-phenylbenzoxazole (2.01 g, 31%) was obtained. Recrystallization from ethyl acetate-hexane gave yellow needles, mp 96–97° C.

Reference Example 70

A mixture of 2-amino-5-bromopyridine (10.0 g). 1,3-dichloroacetone (7.71 g) and 1,2-dimethoxyethane (40 ml) was stirred at room temperature for 4 hours. The precipitated crystals were collected by filtration, to which ethanol (100 ml) was added and heated under reflux. The reaction mixture was concentrated, diluted with saturated aqueous sodium bicarbonate, and extracted with ethyl acetate. The ethyl acetate layer was washed with water, dried ($MgSO_4$), and concentrated under reduced pressure to give crystals of 6-bromo-2-chloromethylimidazo-[1,2-a]pyridine (1.48 g, 10%). Recrystallization from ethyl acetate-hexane gave colorless needles, mp 129–130° C.

Reference Example 71

To a solution of methyl 3-amino-4-hydroxybenzoate and triethylamine (2.42 g) in tetrahydrofuran (60 ml) was added dropwise a solution of 2-thiophenecarbonyl chloride (3.50 g) in tetrahydrofuran (40 ml) at 0° C. The resultant was stirred at room temperature for 2 hours. The reaction mixture was poured into water, and extracted with ethyl acetate. The ethyl acetate layer was washed with 1N-hydrochloric acid and water, dried (MgSO$_4$), and concentrated under reduced pressure. The residue was subjected to a silica gel column chromatography. From the fraction eluted with chloroform-methanol (100:1, v/v), the crystals of methyl 3-(2-thiophenecarboxamide)-4-hydroxybenzoate (2.24 g, 34%) was obtained. Recrystallization from ethyl acetate-hexane gave colorless prisms, mp 241–242° C. A mixture methyl of 3-(2-thiophenecarboxamide)-4-hydroxybenzoate ester (2.20 g), phosphorus pentoxide (4.49 g), hexamethyldisiloxane (10.3 g) and 1,2-dichlorobenzene (30 ml) was heated for 3 hours under reflux. The reaction mixture was poured into water, and extracted with ethyl acetate. The ethyl acetate layer was washed with water, dried (MgSO$_4$), and concentrated under reduced pressure. The residue was subjected to a silica gel column chromatography. From the fraction eluted with ethyl acetate-hexane (1:4, v/v), methyl 2-(2-thienyl)-5-benzoxazolcarboxylate (1.70 g, 83%) was obtained. Recrystallization from ethyl acetate-hexane gave colorless prisms, mp 141–142° C.

Reference Example 72

To a solution of methyl 2-(2-thienyl)-5-benzoxazolecarboxylate (1.50 g) in tetrahydrofuran (30 ml) was slowly added lithium aluminum hydride (220 mg) at 0° C., stirred for 30 minutes. To the reaction mixture was added water, which was made acidic with 1N-hydrochloric acid, and extracted with ethyl acetate. The ethyl acetate layer was washed with water, dried (MgSO$_4$), and concentrated under reduced pressure. The residue was subjected to a silica gel column chromatography. From the fraction eluted with ethyl acetate-hexane (4:1, v/v), 2-(2-thienyl)-5-benzoxazolyl methanol (1.03 g, 77%) was obtained. The recrystalization from ethyl acetate-hexane gave colorless needles, mp 158–159° C.

Reference Example 73

To 2-(2-thienyl)-5-benzoxazolylmethanol (600 mg) was added thionyl chloride (3 ml) at 0° C., stirred for 3 hours. The reaction mixture was concentrated, which was neutalized with saturated aqueous sodium bicarbonate, and extracted with ethyl acetate. The ethyl acetate layer was washed with water, dried (MgSO$_4$), and concentrated under reduced pressure to give crystals of 5-chloromethyl-2-(2-thienyl) benzoxazole (550 mg, 85%). The recrystalization from ethyl acetate-hexane gave colorless needles, mp 152–153° C.

Reference Example 74

A mixture of 2-thiophenecarboxamide (10.2 g), Lawesson's reagent (16.2 g) and toluene (150 ml) was heated for 1 hour under reflux. The reaction mixture was concentrated, to which were added ethyl bromopyruvate (15.7 g) and ethanol (100 ml) and stirred for 1.5 hours at 50° C. To the reaction mixture was add water, which was neutralized with saturated aqueous sodium bicarbonate, and extracted with ethyl acetate. The ethyl acetate layer was washed with water, dried (MgSo$_4$), and concentrated under reduced pressure. The residue was subjected to a silica gel column chromatography. From the fraction eluted with ethyl acetate-hexane (1:4, v/v), ethyl 2-(2-thienyl)-4-thiazolecarboxylate (14.6 g, 76%) was obtained. Recrystallization from ethyl acetate-hexane gave colorless prisms, mp 72–73° C.

Reference Example 75

In substantially the same manner as in Reference Example 72, ethyl 2-(2-thienyl)-4-thiazolecarboxylate was reduced with lithium aluminum hydride to give crystals of 2-(2-thienyl)-4-thiazolylmethanol. The yield was 94%. Recrystallization from ethyl acetate-hexane gave colorless needles, mp 54–55° C.

Reference Example 76

In substantially the same manner as in Reference Example 73, 2-(2-thienyl)-4-thiazolylmethanol was allowed to react with thionylchloride to give 4-chloromethyl-2-(2-thienyl) thiazole. The yield was 65%. Recrystallization from ethyl acetate-hexane gave colorless needles, mp 54–55° C.

Reference Example 77

A mixture of 4-chloromethyl-2-[(E)-2-phenylethenyl] oxazole (5.0 g), sodium acetate (7.48 g) and N,N-dimethylformamide (50 ml) was stirred at 90° C. for 4.5 hours. The reaction mixture was poured onto ice-water, and extracted with ethyl acetate. The ethyl acetate layer was washed with water dried (MgSO$_4$), and concentrated under reduced pressure. To the residue was added potassium carbonate (4.73 g), water (25 ml) and methanol (50 ml) and then the resultant was stirred for 2 hours at room temperature. The reaction mixture was concentrated, to which was added brine, and extracted with ethyl acetate. The ethyl acetate layer was washed with water, dried (MgSO$_4$), and concentrated under reduced pressure to give 2-[(E)-2-phenylethenyl]-4-oxazolylmethanol (4.18 g, 91%). Recrystallization from ethyl acetate-hexane gave colorless prisms, mp 94–95° C.

Reference Example 78

In substantially the same manner as in Reference Example 77, 4-chloromethyl-2-(2-thienyl)oxazole was allowed to react with sodium acetate, and then hydrolyzed to give 2-(2-thienyl)oxazolylmethanol. The yield was 80%. Recrystallization from ethyl acetate-hexane gave pale yellow prisms, mp 98–99° C.

Reference Example 79

To a solution of 3-(4-mercaptophenyl)propionic acid (2.0 g) and triethylamine (2.23 g) in N,N-dimethylformamide (50 ml) was added dropwise a solution of 4-chloromethyl-2-[(E)-2-phenyl ethenyl]oxazole (2.20 g) in N,N-dimethylformamide (10 ml) at 0° C. and then stirred for 2.5 hours. To the reaction mixture was added water, and extracted with diethyl ether. The water layer was made acidic with concentrated hydrochloric acid, and extracted with ethyl acetate. The ethyl acetate layer was washed with water, dried (MgSO$_4$), and concentrated under reduced pressure to give crystals of 3-[4-[2-[(E)-2-phenyl ethenyl]-4-oxazolylmethylthio]phenyl]propionic acid (3.05 g, 84%). Recrystallization from ethyl acetate-hexane gave colorless prisms, mp 120–121° C.

Reference Example 80

To a mixture of 3-[4-[2-[(E)-2-phenylethenyl]-4-oxazolylmethylthio]phenyl]propionic acid (365 mg) and ethanol (10 ml) was added concentrated sulfuric acid (one drop) and heated for 4 hours under reflux. The reaction mixture was concentrated, to which was added saturated aqueous sodium bicarbonate, and extracted with ethyl acetate. The ethyl acetate layer was washed with water, dried (MgSO$_4$), and concentrated under reduced pressure to give crystals of ethyl 3-[4-[2-[(E)-2-phenylethenyl]-4-oxazolylmethylthio]phenyl]propionate (310 mg, 80%). Recrystallization from ethyl acetate-hexane gave colorless prisms, mp 77–78° C.

Reference Example 81

To a solution of ethyl 3-[4-[2-[(E)-2-phenylethenyl]-4-oxazolylmethylthio]phenyl]propionate (205 mg) in tetrahydrofuran (10 ml) was added lithium aluminum hydride at 0° C. and then stirred for one hour at room temperature. To the reaction mixture were added water and 1N-hydrochloric acid, and extracted with ethyl acetate. The ethyl acetate layer was washed with water, dried (MgSO$_4$), and concentrated under reduced pressure to give crystals of 3-[4-[2-[(E)-2-phenyl ethenyl]-4-oxazolylmethylthio]phenyl]propanol (135 mg, 77%). Recrystallization from ethyl acetate-hexane gave colorless needles, mp 91–92° C.

Reference Example 82

A solution of ethyl 3-benzyloxycinnamate in tetrahydrofuran (300 ml) was added dropwise to a suspension of lithium aluminum hydride in tetrahydrofuran (300 ml) at 0° C. and then stirred for 2 hours. To the reaction mixture was added carefully water and the insoluble material was filtered off. The filtrate was concentrated. The residue was dissolved in ethyl acetate and washed with 1N-hydrochloric acid and water, dried (MgSO$_4$), and concentrated under reduced pressure. The residue was subjected to a silica gel column chromatography. From the fraction eluted with ethyl acetate-hexane (1:4, v/v), 3-(3-benzyloxyphenyl)propanol (52.7 g, 62%) was obtained. Oily substance.

NMR (δ ppm in CDCl$_3$): 1.8–1.95(2H,m), 2.68(2H,t,J= 6.8 Hz); 3.65(2H,t,J=6.6 Hz), 5.05(2H,s), 6.75–6.85(3H,m), 7.15–7.5(6H,m).

Reference Example 83

A solution of 4-(3-benzyloxyphenyl)butyric acid (22.0 g) in tetrahydrofuran (150 ml) was added dropwise to a suspension of lithium aluminum hydride (6.18 g) in tetrahydrofuran (150 ml) at 0° C. and then stirred for one hour at room temperature. The reaction mixture was quenched with H$_2$O, acidified with 1N-hydrochloric acid, and extracted with ethyl acetate. The ethyl acetate layer was washed with 1N-hydrochloric acid, saturated aqueous sodium bicarbonate and water, dried (MgSO$_4$), and concentrated under reduced pressure to give 4-(3 -benzyloxyphenyl)butanol (20.5 g, 99%). Oily substance.

NMR (δ ppm in CDCl$_3$): 1.5–1.8(4H,m), 2.62(2H,t,J=7.4 Hz), 3.64(2H,t,J=6.4 Hz), 5.05(2H,s), 6.75–6.85(3H,m), 7.15–7.45(6H,m).

Reference Example 84

Methanesulfonyl chloride (320 mg) was added to a solution of 3-[4-[2-[(E)-2-phenylethenyl]-4-oxazolylmethylthio] phenyl]propanol (500 mg) and triethylamine (280 mg) in tetrahydrofuran (30 ml) at 0° C. and then stirred for 4 hours at room temperature. To the reaction mixture was added water, and extracted with ethyl acetate. The ethyl acetate layer was washed with water, dried (MgSO$_4$), and concentrated under reduced pressure to give 3-[4-[2-[(E)-2-phenylethenyl]-4-oxazolylmethylthio]phenyl]propyl methanesulfonate (540 mg, 90%). Recrystallization from ethyl acetate-hexane gave pale yellow prisms, mp 97–98° C.

Reference Example 85

Methanesulfonyl chloride (17.9 g) was added to a solution of 4-(4-benzyloxyphenyl)butanol (20.0 g) and triethyl amine (15.8 g) in ethyl acetate (500 ml) at 0° C. and then stirred for 5 hours at room temperature. The reaction mixture was washed with water, dried (MgSo$_4$) and concentrated under reduced pressure to give 4-(4-benzyloxyphenyl)butyl methanesulfonate (26.0 g, quantitatively). Oily substance.

NMR(δ ppm in CDCl$_3$): 1.6–1.85(4H,m), 2.60(2H,t,J=7 Hz), 2.97(3H,s), 4.22(2H,t,J=6 Hz), 5.04(2H,s), 6.90(2H,d, J=8.6 Hz), 7.08(2H,d,J=8.6 Hz), 7.3–7.45(5H,m).

Reference Example 86

In substantially the same manner as in Reference Example 85, 3-(3-benzyloxyphenyl)propanol was allowed to react with methanesulfonyl chloride to give 3-(3-benzyloxyphenyl)propyl methanesulfonate. The yield was quantative. Oily substance.

NMR(δ ppm in CDCl$_3$): 2.0–2.15(2H,m), 2.73(2H,t,J=7.6 Hz), 2.98(3H,s), 4.22(2H,t,J=6.2 Hz), 5.06(2H,s), 6.75–6.85 (3H,m), 7.15–7.5(6H,m).

Reference Example 87

In substantially the same manner as in Reference Example 85, 4-(3-benzyloxyphenyl)butanol was allowed to react with methanesulfonylchloride to give 4-(3-benzyloxyphenyl) butyl methanesulfonate. The yield was quantative. Oily substance.

NMR(δ ppm in CDCl$_3$): 1.7–1.8(4H,m), 2.64(2H,t,J=7 Hz), 2.98(3H,s), 4.22(2H,t,J=6 Hz), 5.06(2H,s), 6.75–6.85 (3H,m), 7.21(1H,dd,J=9.2,7.2 Hz), 7.3–7.5(5H,m).

Reference Example 88

A mixture of 4-(4-benzyloxyphenyl)butyl methane sulfonate (25.0 g), imidazole (11.2 g), potassium carbonate (15.5 g) and N,N-dimethylformamide (200 ml) was stirred for 16 hours at 80° C. The reaction mixture was poured into water, and extracted with ethyl acetate. The ethyl acetate layer was washed with water, dried (MgSO$_4$), and concentrated under reduced pressure. The residue was subjected to a silica gel column chromatography. From the fraction eluted with ethyl acetate-methanol (20:1, v/v), 1-[4-(4-benzyloxyphenyl)butyl]imidazole (14.0 g, 61%) was obtained. Recrystallization from ethyl acetate-hexane gave colorless prisms, mp 97–98° C.

Reference Example 89

In substantially the same manner as in Reference Example 88, 3-(3-benzyloxyphenyl)propyl methanesulfonate was allowed to react with imidazole to give 1-[3-(3-benzyloxyphenyl)propyl]imidazole. The yield was 44%. Recrystallization from ethyl acetate-hexane gave colorless prisms, mp 82–83° C.

Reference Example 90

In substantially the same manner as in Reference Example 88, 4-(3-benzyloxyphenyl)butyl methanesulfonate was allowed to react with imidazole to give 1-[4-(3 -benzyloxyphenyl)butyl]imidazole. The yield was 61%. Oily substance.

NMR(δ ppm in CDCl$_3$): 1.5–1.8(4H,m), 2.58(2H,t,J=7.2 Hz), 3.88(2H,t,J=7 Hz), 5.03(2H,s), 6.7–6.85(4H,m), 7.04 (1H,s), 7.15–7.5(7H,m).

Reference Example 91

A mixture of 1-[4-(4-benzyloxyphenyl)butyl]imidazole (13.0 g), palladium-carbon (5%, 10.0 g) and ethanol (100 ml) was subjected to catalitic hydrogenation at room temperature under 1 atom. The catalyst was filtered off, and the filtrate was concentrated to give 1-[4-(4-hydroxyphenyl) butyl]imidazole (8.58 g, 94%). Recrystallization from ethyl acetate-hexane gave colorless prisms, mp 124–125° C.

Reference Example 92

In substantially the same manner as in Reference Example 91, 1-[3-(3-benzyloxyphenyl)propyl]imidazole was subjected to catalitic hydrogenation to give 1-[3-(3-hydroxyphenyl)propyl]imidazole. The yield was 90%. Recrystallization from ethyl acetate-hexane gave colorless prisms, mp 110–111° C.

Reference Example 93

In substantially the same manner as in Reference Example 91, 1-[4-(3-benzyloxyphenyl)butyl]imidazole was subjected to catalitic hydrogenation to give 1-[4-(3-hydroxyphenyl) butyl]imidazole. The yield was 80%. Recrystallization from ethyl acetate-hexane gave colorless prisms, mp 133–134° C.

Reference Example 94

To a mixture of 5-amino-2-methoxypyridine (5.00 g), 47% hydrobromic acid (8.75 g) and acetone (50 ml) was added dropwise a solution of sodium nitrite (3.06 g) in water (5 ml) at 5–10° C. After stirring for 30 minutes, methyl acrylate (20.8 g) was added, to which cuprous oxide (50 mg) was added while stirring vigorously at 15° C. After stirring for one hour at room temperature, the reaction mixture was concentrated, concentrated aqueous ammonia was added, and extracted with ethyl acetate. The ethyl acetate layer was washed with water, dried ($MgSO_4$), and concentrated under reduce pressure. The residue was subjected to a silica gel chromatography. From the fraction eluted with ethyl acetate-hexane (1:9, v/v), methyl 2-bromo-3-(2-methoxy-5-pyridyl) propionate (6.40 g, 58%) was obtained. Oily substance.

NMR($\delta$ ppm in $CDCl_3$): 3.18(1H,dd,J=14.6,7.6 Hz), 3.42 (1H,dd,J=14.6,7.6 Hz), 3.75(3H,s), 3.92(3H,s), 4.33(1H,t,J= 7.6 Hz), 6.70(1H,d,J=8.6 Hz), 7.44(1H,dd,J=8.6,2.4 Hz), 8.02(1H,d,J=2.4 Hz).

The oily substance (6.30 g) was dissolved in methanol (150 ml), and subjected to catalytic hydrogenation on palladium-carbon (5%, 4.0 g). The catalyst was filtered off and the filtrate was concentrated. To the residue was added saturated aqueous sodium bicarbonate, and extracted with ethyl acetate. The ethyl acetate layer was washed with water, dried ($MgSO_4$), and concentrated under reduced pressure to give methyl 3-(2-methoxy-5-pyridyl)propionate (3.68 g, 82%). Oily substance.

NMR($\delta$ ppm in $CDCl_3$): 2.59(2H,t,J=7.6 Hz), 2.88(2H,t, 7.6 Hz), 3.67(3H,s), 3.91(3H,s), 6.68(1H,d,J=8.4 Hz), 7.42 (1H,dd,J=8.4,2.4 Hz), 8.00(1H,d,J=2.4 Hz).

Reference Example 95

In substantially the same manner as in Reference Example 82, methyl 3-(2-methoxy-5-pyridyl)propionate was reduced by lithium aluminum hydride to give 3-(2-methoxy-5-pyridyl)propanol. The yield was quantative. Oily substance.

NMR($\delta$ ppm in $CDCl_3$): 1.8–2.0(2H,m), 2.64(2H,t,J=7.6 Hz), 3.6–3.75(2H,m), 3.91(3H,s), 6.69(1H,d,J=8.4 Hz), 7.43 (1H,dd,J=8.4,2.6 Hz), 7.99(1H,d,J=2.6 Hz).

Reference Example 96

In substantially the same manner as in Reference Example 85, 3-(2-methoxy-5-pyridyl)propanol was reacted with methanesulfonyl chloride to give 3-(2-methoxy-5-pyridyl) propyl methanesulfonate. The yield was quantative. Oily substance.

NMR($\delta$ ppm in $CDCl_3$): 1.95–2.1(2H,m), 2.68(2H,t,J=7.4 Hz), 3.01(3H,s), 3.91(3H,s), 4.23(2H,t,J=7.4 Hz), 6.70(1H, d,J=7.8 Hz), 7.41(1H,dd,J=7.8,1.2 Hz), 7.98(1H,d,J=1.2 Hz).

Reference Example 97

In substantially the same manner as in Reference Example 88, 3-(2-methoxy-5-pyridyl)propyl methanesulfonate was reacted with imidazole to give 5-[3-(1-imidazolyl)propyl]-2-methoxypyridine. The yield was 94%. Oily substance.

NMR($\delta$ ppm in $CDCl_3$): 2.0–2.2(2H,m), 2.54(2H,t,J=7.5 Hz), 3.9–4.0(5H,m), 6.70(1H,d,J=8.4 Hz), 6.92(1H,s), 7.08 (1H,s), 7.3–7.4(1H,m), 7.47(1H,s), 7.96(1H,s).

Reference Example 98

A mixture of 5-[3-(1-imidazolyl)propyl]-2-methoxypyridine(2.10 g), phosphorus oxychloride (7.44 g) and N,N-dimethylformamide (14.6 g) was stirred at 100° C. for 10 hours. To the reaction mixture was added saturated aqueous sodium acetate and saturated aqueous sodium bicarbonate, and extracted with ethyl acetate. The ethyl acetate layer was washed with water, dried ($MgSO_4$), and concentrated under reduced pressure. The residue was subjected to a silica gel chloromatography. From the fraction eluted with ethyl acetate-methanol (20:1, v/v), 2-chloro-5-[3-(1-imidazolyl)propyl]pyridine (1.28 g, 60%) was obtained. Oily substance.

NMR($\delta$ ppm in $CDCl_3$): 2.0–2.2(2H,m), 2.60(2H,t,J=7.9 Hz), 3.99(2H,t,J=7 Hz), 6.91(1H,s), 7.09(1H,s), 7.25–7.3 (1H,m), 7.4–7.5(2H,m), 8.21(1H,d,J=2.4 Hz).

Reference Example 99

In substantially the same manner as in Reference Example 47, 3-furancarboxamide was reacted with 1,3-dichloroacetone to give 4-chloromethyl-2-(3-furyl)oxazole. The yield was 44%. Recrystallization from diethyl ether-hexane gave colorless prisms. mp 70–71° C.

Reference Example 100

In substantially the same manner as in Reference Example 47, 2-thiopheneacetamide was reacted with 1,3-dichloroacetone to give 4-chloromethyl-2-(2-thienylmethyl) oxazole. The yield was 27%. Oily substance.

NMR($\delta$ ppm in $CDCl_3$): 4.32(2H,s), 4.49(2H,s), 6.95–7.0 (2H,m), 7.15–7.25(1H,m), 7.58(1H,s).

Reference Example 101

In substantially the same manner as in Reference Example 77, ethyl 2-(1-pyrrolyl)-4-thiazolecarboxylate was reduced by lithium aluminum hydride to give 2-(1-pyrrolyl)-4-thiazolylmethanol. The yield was 69%. Recrystallization from ethyl acetate-hexane gave colorless prisms, mp 111–113° C.

Reference Example 102

In substantially the same manner as in Reference Example 77, ethyl 2-(3-pyridyl)-4-thiazolecarboxylate was reduced by lithium aluminum hydride to give 2-(3-pyridyl)-4-thiazolylmethanol. The yield was 16%. Recrystallization from ethyl acetate-hexane gave colorless needles, mp 121–122° C.

Reference Example 103

In substantially the same manner as in Reference Example 47, 5-cyano-2-thiophenecarboxamide was reacted with 1,3-dichloroacetone to obtain 4-chloromethyl-2-(5-cyano-2-thienyl)oxazole. The yield was 22%. Recrystallization from ethyl acetate-hexane gave colorless prisms, mp 146–147° C.

Reference Example 104

A mixture of 2-thiophenecarboxamide (15.2 g) and ethyl 4-chloroacetoacetate (19.6 g) was stirred at 130° C. for 4 h. Water, ethyl acetate and potassium carbonate were added to the reaction mixture. The ethyl acetate layer was separated, washed with water, dried ($MgSO_4$), and concentrated. The residue was purified by silica gel column chromatography. From the fraction eluted with diethyl ether-hexane (1:9, v/v) ethyl 2-(2-thienyl)-4-oxazolylacetate (1.48 g, 5%) was obtained. Recrystallization from hexane gave colorless prisms, mp 56–57° C.

Reference Example 105

Sodium hydride (60% in oil, 1.20 g) was added to a stirred solution of diethyl malonate (6.01 g) in N,N-dimethylformamide (40 ml) at room temperature. After stirring for 30 min, a solution of 4-chloromethyl-2-(2-thienyl)oxazole (5.0 g) in N,N-dimethylformamide (20 ml) was added dropwise to the mixture, and then the stirring was continued for 5 h. The reaction mixture was poured into water and extracted with ethyl acetate. The ethyl acetate layer was washed with water, dried ($MgSO_4$), and concentrated. The residue was dissolved in acetic acid (100 ml) and 6N HCl (40 ml). After refluxing for 5 h, the reaction mixture was concentrated. The residue was made alkaline with aqueous sodium hydroxide and extracted with diethyl ether. The aqueous layer was separated, acidified with conc.HCl and extracted with ethyl acetate. The ethyl acetate layer was washed with brine, dried ($MgSO_4$), and concentrated. Ethanol (200 ml) and conc.$H_2SO_4$ (0.5 ml) were added to the residue, and then the resultant was refluxed for 9 h. The reaction mixture was concentrated and diluted with ethyl acetate. The ethyl acetate layer was washed with saturated aqueous sodium bicarbonate and water, dried ($MgSO_4$), and concentrated to give an oil which was purified by silica gel column chromatography. From the fraction eluted with ethyl acetate-hexane (1:9, v/v) ethyl 3-[2-(2-thienyl)-4-oxazolyl]propionate (1.81 g, 29%) was obtained. Recrystallization from hexane gave colorless prisms, mp 42–43° C.

Reference Example 106

In substantially the same manner as in Reference Example 72. ethyl 2-(2-thienyl)-4-oxazolylacetate was subjected to reduction with lithium alminum hydride to obtain 2-[2-(2-thienyl)-4-oxazolyl]ethanol as an oil. The yield was 73%.

NMR($\delta$ ppm in $CDCl_3$): 2.82(2H,td,J=6,1 Hz), 3.94(2H, t,J=6 Hz), 7.11(1H,dd,J=5,3.6 Hz), 7.42(1H,dd,J=5,1.2 Hz), 7.46(1H,t,J=1Hz), 7.65(1H,dd,J=3.6,1.2 Hz).

Reference Example 107

In substantially the same manner as in Reference Example 72, ethyl 3-[2-(2-thienyl)-4-oxazolyl]propionate was subjected to reduction with lithium alminum hydride to obtain 3-[2-(2-thienyl)-4-oxazolyl]propanol as an oil. The yield was 97%.

NMR($\delta$ ppm in $CDCl_3$): 1.8–2.2(2H,m), 2.70(2H,t,J=7 Hz), 3.75(2H,td,J=6,1 Hz), 7.05–7.15(1H,m), 7.35–7.45 (2H,m), 7.6–7.7(1H,m).

Reference Example 108

A mixture of 2-bromoacetylthiophene (4.10 g), ethyl thiooxamate (2.93 g) and ethanol (40 ml) was refluxed for 4 h. The reaction mixture was poured into water and extracted with ethyl acetate. The ethyl acetate layer was washed with water, dried ($MgSO_4$), and concentrated to give an oil which was purified by silica gel column chromatography. From the fraction eluted with ethyl acetate-hexane (1:5, v/v) ethyl 4-(2-thienyl)-2-thiazolecarboxylate was obtained. Recrystallization from isopropyl ether gave pale yellow prisms (1.37 g, 29%), mp 50–52° C.

Reference Example 109

2-bromoacetylthiophene (10.3 g) was added to a stirred solution of hexamethylenetetramine (7.71 g) in chloroform (60 ml), and stirred at room temperature for 3 h. The precipitated 2-thiophenecarbonylmethylhexaminium bromide (15.9 g, 92%) was collected by filtration. The cryst. (10.4 g) was added to a mixture of ethanol (100 ml) and conc.HCl (24 ml), and then stirred at 50° C. for 1 h. The reaction mixture was cooled and the insoluble crystals were removed by filtration. The filtrate was concentrated to give crystals which were collected by filtration. The cryst. (1.80 g) was added to a mixture of ethyl chloroglyoxylate (1.34 ml) and toluene (20 ml), and then stirred at 80° C. for 6 h. The reaction mixture was poured into wate and extracted with ethyl acetate. The ethyl acetate layer was washed with saturated aqueous sodium bicarbonate and water, dried ($MgSO_4$), and concentrated to give an oil which was purified by silica gel column chromatography. From the fraction eluted with ethyl acetate-hexane (1:1, v/v) the crystals of ethyl N-(2-thiophenecarbonylmethyl)oxamate (1.24 g, 51%) were obtained. The cryst. (1.11 g) and diphosphorus pentasulfide (2.05 g) were suspended in chloroform (20 ml) and refluxed for 3 h. The reaction mixture was diluted with water and the insoluble material was removed by filtration. The chloroform layer was separated, washed with water, dried ($MgSO_4$), and concentrated to obtain ethyl 5-(2-thienyl)-2-thiazolecarboxylate (1.07 g, 97%). Recrystallization from ethyl acetate-hexane gave colorless needles, mp 68–69° C.

Reference Example 110

Acetic acid (3.78 ml) was added to a stirred mixture of 2-thiophenecarbothioamide (3.15 g), ethyl chloroformylacetate potassium salt (6.23 g) and ethanol (60 ml). Afte refluxing for 4 h, ethyl chloroformylacetate potassium salt (4.15 g) and acetic acid (2.52 ml) were added, and then the refluxing was continued for further 20 h. The reaction mixture was concentrated, diluted with saturated aqueous sodium bicarbonate, and extracted with ethyl acetate. The ethyl acetate layer was washed with water, dried ($MgSO_4$), and concentrated to give an oil which was purified by silica gel column chromatography. From the fraction eluted with ethyl acetate-hexane (1:1, v/v) the crystals of ethyl 2-(2-thienyl)-5-thiazolecarboxylate (3.29 g, 63%) were obtained. Recrystallization from ethyl acetate-hexane gave colorless needles, mp 61–62° C.

Reference Example 111

Methanol (1.5 ml) in tetrahydrofuran (2 ml) was added dropwise to a stirred and refluxed mixture of ethyl 4-(2-thienyl)-2-thiazolecarboxylate (1.36 g), sodium borohydride (0.35 g) and tetrahydrofuran (15 ml). After refluxing for 1 h, the reaction mixture was poured into water, acidified with 1N HCl and extracted with ethyl acetate. The ethyl acetate layer was washed with water, dried (MgSO$_4$), and concentrated to give 4-(2-thienyl)-2-thiazolylmethanol (0.92 g, 82%). Recrystallization from ethyl acetate-hexane gave colorless prisms, mp 113–114° C.

Reference Example 112

In substantially the same manner as in Reference Example 111, ethyl 5-(2-thienyl)-2-thiazolecarboxylate was subjected to reduction with sodium borohydride to obtain 5-(2-thienyl)-2-thiazolylmethanol. The yield was 74%. Recrystallization from ethyl acetate-hexane gave pale yellow prisms, mp 67–68° C.

Reference Example 113

In substantially the same manner as in Reference Example 111, ethyl 2-(2-thienyl)-5-thiazolecarboxylate was subjected to reduction with sodium borohydride to obtain 2-(2-thienyl)-5-thiazolylmethanol. The yield was 94%. Recrystallization from ethyl acetate-hexane gave colorless prisms, mp 89–90° C.

Reference Example 114

A mixture of 5-methyl-2-thiophenecarboxamide (0.79 g), 1,3-dichloroacetone (0.63 g), and ethanol (20 ml) was refluxed for 2 h. The reaction mixture was concentrated, diluted with saturated aqueous sodium bicarbonate, and extracted with ethyl acetate. The ethyl acetate layer was washed with water, dried (MgSO$_4$), and concentrated. The residue was purified by silica gel column chromatography. From the fraction eluted with diethyl ether-hexane (1:10, v/v) 4-chloromethyl-2-(5-methyl-2-thienyl)thiazole (0.60 g, 52%) was obtained. Recrystallization from diethyl ether-hexane gave colorless prisms, mp 89–90° C.

Reference Example 115

A mixture of 2-thiophenecarbonylmethylhexaminium bromide (10.4 g), ethanol (100 ml) and conc.HCl (24 ml) was stirred at 50° C. for 1 h. The reaction mixture was cooled and the insoluble crystals were removed by filtration. The filtrate was concentrated to give crystals (5.20 g, quant.) which were collected by filtration. The cryst. (3.55 g) was added to a mixture of toluene (20 ml) and water (20 ml), and then chloroacetyl chloride (1.43 ml) and 2N sodium hydroxide (10 ml) were added dropwise to the mixture at 0° C. After stirring at room temperature for 2 h, the crystals were collected by filtration. The toluene layer was separated, washed with water, dried (MgSO$_4$), and concentrated to give crystals. The crystals combined were recrystallized from ethyl acetate to give N-(2-thiophenecarbonylmethyl) chloroacetamide (1.82 g, 42%). A mixture of the cryst. (1.67 g), toluene (20 ml) and phosphorus oxychloride (1.8 ml) was stirred at 80° C. for 4H. The reaction mixture was concentrated, diluted with water, neutralized with potassium carbonate, and extracted with ethyl acetate. The ethyl acetate layer was washed with water, dried (MgSO$_4$), and concentrated. The residue was purified by silica gel column chromatography. From the fraction eluted with ethyl acetate-hexane (1:3, v/v) 2-chloromethyl-5-(2-thienyl)oxazole (1.40 g, 92%) was obtained as an oil.

NMR(δ ppm in CDCl$_3$): 4.65(2H,s), 7.09(1H,dd,J=5,3.8 Hz), 7.18(1H,s), 7.3–7.4(2H,m).

Reference Example 116

A mixture of ethyl 7-methoxy-3-quinolinecarboxylate (12.0 g) and 47% HBr (200 ml) was refluxed for 24 h. The precipitated crystals (12.63 g) were collected and added to a mixture of ethanol (400 ml) and conc.H$_2$SO$_4$ (2 ml). After refluxing for 20 h, the reaction mixture was concentrated, diluted with saturated aqueous sodium bicarbonate, and extracted with ethyl acetate. The ethyl acetate layer was washed with water, dried (MgSO$_4$), and concentrated to give ethyl 7-hydroxy-3-quinoline-carboxylate (5.70 g, 51%). Recrystallization from ethyl acetate-hexane gave colorless prisms, 179–180° C.

Reference Example 117

Sodium hydride (60% in oil, 1.07 g) was added to a stirred solution of ethyl 7-hydroxy-3-quinolinecarboxylate (5.30 g) in tetrahydrofuran (200 ml) at 0° C., and stirred at room temperature for 1 h. N-phenyltrifluoromethanesulfonimide (10.47 g) was added to the mixture, and the resultant was stirred for 1 h. The reaction mixture was poured into water and extracted with ethyl acetate. The ethyl acetate layer was washed with water, dried (MgSO$_4$), and concentrated. The residue was purified by silica gel column chromatography. From the fraction eluted with ethyl acetate-hexane (1:4, v/v) ethyl 7-trifluoromethanesulfonyloxy-3-quinolinecarboxylate (7.65 g, 90%) was obtained. Recrystallization from ethyl acetate-hexane gave colorless prisms, 153–154° C.

Reference Example 118

A solution of phenylboronic acid (2.48 g) in ethanol (30 ml) was added dropwise to a stirred mixture of ethyl 7-trifluoromethanesulfonyloxy-3-quinolinecarboxylate (7.40 g), 2N sodium carbonate (28 ml), lithium chloride (2.70 g), tetrakis(triphenylphosphine)palladium (1.27 g) and toluene (120 ml) under argon atmospher. After stirring at 90° C. for 14 h, the insoluble material was removed by filtration. The filtrate was extgracted with ethyl acetate. The ethyl acetate layer was washed with saturated aqueous sodium bicarbonate and water, dried (MgSO$_4$), and concentrated. The residue was purified by silica gel column chromatography. From the fraction eluted with ethyl acetate-hexane (1:4, v/v) ethyl 7-phenyl-3-quinolinecarboxylate (5.14 g, 87%) was obtained. Recrystallization from ethyl acetate-hexane gave colorless prisms, 118–119° C.

Reference Example 119

In substantially the same manner as in Reference Example 118, 7-trifluoromethanesulfonyloxy-3-quinolinecarboxylate was reacted with 2-thienylboronic acid to obtain ethyl 7-(2-thienyl)-3-quinolinecarboxylate. The yield was 67%. Recrystallization from ethyl acetate-hexane gave colorless prisms, 146–147° C.

Reference Example 120

In substantially the same manner as in Reference Example 72, 7-phenyl-3-quinolinecarboxylate was subjected to reduction with lithium aluminum hydride to obtain 7-phenyl-3-quinolylmethanol. The yield was 39%. Recrystallization from ethyl acetate-hexane gave colorless prisms, 128–129° C.

Reference Example 121

Diisobutylalminium hydride (1M in toluene, 7.2 ml) was added dropwise to a stirred solution of 7-(2-thienyl)-3-quinolinecarboxylate (500 mg) in tetrahydrofuran (30 m) at 0° C. After stirring for 30 min, the reaction mixture was poured into water and extracted with ethyl acetate. The ethyl acetate layer was washed with brine, dried (MgSO$_4$), and concentrated. The residue was purified by silica gel column chromatography. From the fraction eluted with ethyl acetate-hexane (1:2, v/v) 7-(2-thienyl)-3-quinolylmethanol (270 mg, 63%) was obtained. Recrystallization from ethyl acetate-hexane gave yellow prisms, 143–144° C.

Reference Example 122

In substantially the same manner as in Reference Example 73, 7-phenyl-3-quinolylmethanol was reacted with thionyl chloride to obtain 3-chloromethyl-7-phenylquinoline. The yield was 96%. Recrystallization from ethyl acetate-hexane gave colorless prisms, 105–106° C.

Reference Example 123

In substantially the same manner as in Reference Example 73, 7-(2-thienyl)-3-quinolylmethanol was reacted with thionyl chloride to obtain 3-chloromethyl-7-(2-thienyl) quinoline. The yield was 77%. Recrystallization from ethyl acetate-hexane gave colorless leaflets, 120–121° C.

Reference Example 124

In substantially the same manner as in Reference Example 82, ethyl 4-benzyloxy-3-methoxycinnamate was subjected to reduction with lithium aluminum hydride to obtain 3-(4-benzyloxy-3-methoxyphenyl)propanol. The yield was 56%. Recrystallization from ethyl acetate-hexane gave colorless prisms, 57–58° C.

Reference Example 125

In substantially the same manner as in Reference Example 85, 3-(4-benzyloxy-3-methoxyphenyl)propanol was reacted with methanesulfonyl chlorode to obtain 3-(4-benzyloxy-3-methoxyphenyl)propyl methanesulfonate. The yield was quantitative. Recrystallization from ethyl acetate-hexane gave colorless prisms, 87–88° C.

Reference Example 126

In substantially the same manner as in Reference Example 88, 3-(4-benzyloxy-3-methoxyphenyl)propyl methanesulfonate was reacted with imidazole to obtain 1-[3-(4-benzyloxy-3-methoxyphenyl)propyl]imidazole as an oil. The yield was 57%.

NMR(δ ppm in CDCl$_3$): 2.0–2.2(2H,m), 2.55(2H,t,J=7.4 Hz), 3.88(3H,s), 3.92(2H,t,J=7 Hz), 5.13(2H,s), 6.6–6.7(3H, m), 6.82(1H,d,J=8 Hz), 6.9–7.5(8H,m).

Reference Example 127

In substantially the same manner as in Reference Example 91, 1-[3-(4-benzyloxy-3-methoxyphenyl)propyl]imidazole was subjected to catalytic hydrogenation to obtain 1-[3-(4-hydroxy-3-methoxyphenyl)propyl]imidazole. The yield was 83%. Recrystallization from ethyl acetate gave colorless prisms, 127–128° C.

Reference Example 128

In substantially the same manner as in Reference Example 82, ethyl 3-(3-chloro-4-methoxymethoxyphenyl)propionate was subjected to reduction with lithium aluminum hydride to obtain 3-(3-chloro-4-methoxymethoxyphenyl)propanol as an oil. The yield was 97%.

NMR(δ ppm in CDCl$_3$): 1.8–1.95(2H,m), 2.64(2H,t,J=7.6 Hz), 3.52(3H,s), 3.66(2H,t,J=6.2 Hz), 5.22(2H,s), 6.95–7.25 (3H,m).

Reference Example 129

In substantially the same manner as in Reference Example 85, 3-(3-chloro-4-methoxymethoxyphenyl)propanol was reacted with methanesulfonyl chloride to obtain 3-(3-chloro-4-methoxymethoxyphenyl)propyl methanesulfonate as an oil. The yield was quantitative.

NMR(δ ppm in CDCl$_3$): 1.95–2.15(2H,m), 2.96(2H,t,J= 7.5 Hz), 3.00(3H,s), 3.52(3H,s), 4.22(2H,t,J=6.4 Hz), 5.22 (2H,s), 6.95–7.15(2H,m), 7.2–7.25(1H,m).

Reference Example 130

In substantially the same manner as in Reference Example 88, 3-(3-chloro-4-methoxymethoxyphenyl)propyl methanesulfonate was reacted with imidazole to obtain 1-[3-(3-chloro-4-methoxymethoxyphenyl)propyl]imidazole as an oil. The yield was 65%.

NMR(δ ppm in CDCl$_3$): 2.0–2.2(2H,m), 2.54(2H,t,J=7.7 Hz), 3.52(3H,s), 3.93(2H,t,J=7 Hz), 5.22(2H,s), 6.9–7.0(3H, m), 7.05–7.2(3H,m), 7.46(1H,s).

Reference Example 131

A mixture of 1-[3-(3-chloro-4-methoxymethoxyphenyl) propyl]imidazole (4.50 g), 10% H$_2$SO$_4$ (50 ml) and acetone (50 ml) was refluxed for 3 h. Sodium hydroxide (7.0 g) was added to the mixture at 0° C., and extracted with ethyl acetate. The ethyl acetate layer was washed with water, dried (MgSO$_4$), and concentrated to obtain 1-[3-(3-chloro-4-hydroxyphenyl)propyl]imidazole (3.50 g, 92%). Recrystallization from ethanol gave colorless prisms, 112–113° C.

Reference Example 132

A mixture of 2-cyanothiophene (10.9 g), hydroxylamine hydrochloride (6.96 g), and 70% ethanol (100 ml) was stirred at 80° C. for 2 h. The reaction mixture was poured into water and extracted with ethyl acetate. The ethyl acetate layer was extracted with 2N HCl. The aqueous layer combined was made alkaline with potassium carbonate and extracted with ethyl acetate. The ethyl acetate layer was washed with water, dried (MgSO$_4$), and concentrated to give crystals (12.4 g, 87%). The crystals (7.11 g) was mixed with potassium carbonate in acetone, and then chloroacetyl chloride was added ropwise to the mixture at 0° C. After stirring at room temperature for 16 h, the reaction mixture was concentrated and treated with water to give crystals (8.82 g, 81%) which were collected by filtration. The crystals (7.82 g) was added to xylene (100 ml), and then refluxed with separating wate for 2 h. The reaction mixture was concentrated and diluted with ethyl acetate. The ethyl acetate layer was washed with water, dried (MgSO$_4$), and concentrated. The residue was purified by silica gel column chromatography. From the fraction eluted with ethyl acetate-hexane (1:10, v/v) crystals of 5-chloromethyl-3-(2-thienyl)-1,2,4-oxadiazole were obtained. Recrystallization from ethyl acetate-hexane gave colorless prisms (6.23 g, 87%), mp 58–59° C.

Working Example 1

To a solution of 3-[4-[2-[(E)-2-phenylethenyl]-4-oxazolylmethoxy]phenyl]propanol (760 mg), tributyl phosphine (1.01 g) and 1,2,4-triazole (280 mg) in tetrahydrofuran (15 ml) was added dropwise, at 0° C., diethyl azodicarboxylate (700 mg). The mixture was heated for one hour under reflux, poured into water, and extracted with ethyl acetate. The ethyl acetate layer was washed with water, dried (MgSO₄), and concentrated. The residue was subjected to a silica gel column chromatography. The crystals obtained from the fraction eluted with ethyl acetate-hexane (2:1, v/v) were recrystallized from ethyl acetate-hexane to give 1-[3-[4-[2-[(E)-2-phenylethenyl]-4-oxazolylmethoxy]phenyl] propyl]-1,2,4-triazole (540 mg, 70%) as colorless prisms, mp 108–109° C.

Working Example 2

In substantially the same manner as in Working Example 1, 4-[4-[2-[(E)-2-phenylethenyl]-4-oxazolylmethoxy] phenyl]butanol was allowed to react with 1,2,4-triazole to give 1-[4-[4-[2-[(E)-2-phenylethenyl]-4-oxazolylmethoxy] phenyl]butyl]-1,2,4-triazole. The yield was 71%. Recrystallization from ethyl acetate-hexane gave colorless prisms, mp 94–95° C.

Working Example 3

In substantially the same manner as in Working Example 1, 5-[4-[2-[(E)-2-phenylethenyl]-4-oxazolylmethoxy] phenyl]pentanol was allowed to react with 1,2,4-triazole to give 1-[5-[4-[2-[(E)-2-phenylethenyl]-4-oxazolylmethoxy] phenyl]pentyl]-1,2,4-triazole. The yield was 60%. Recrystallization from ethyl acetate-hexane gave colorless prisms, mp 103–104° C.

Working Example 4

In substantially the same manner as in Working Example 1, 3-[3-[2-[(E)-2-phenylethenyl]-4-oxazolylmethoxy] phenyl]propanol was allowed to react with 1,2,4-triazole to give 1-[3-[3-[2-[(E)-2-phenylethenyl]-4-oxazolylmethoxy] phenyl]propyl]-1,2,4-triazole. The yield was 61%. Recrystallization from ethyl acetate-hexane gave colorless prisms, mp 59–60° C.

Working Example 5

In substantially the same manner as in Working Example 1, 3-[2-[2-[(E)-2-phenylethenyl]-4-oxazolylmethoxy] phenyl]propanol was allowed to react with 1,2,4-triazole to give 1-[3-[2-[2-[(E)-2-phenylethenyl]-4-oxazolylmethoxy] phenyl]propyl]-1,2,4-triazole. The yield was 54%. Recrystallization from ethyl acetate-hexane gave colorless prisms, mp 72– 73° C.

Working Example 6

In substantially the same manner as in Working Example 1, 6-[4-[2-[(E)-2-phenylethenyl]-4-oxazolylmethoxy] phenyl]hexanol was allowed to react with 1,2,4-triazole to give 1-[6-[4-[2-[(E)-2-phenylethenyl]-4-oxazolylmethoxy] phenyl]hexyl]-1,2,4-triazole. The yield was 65%. Recrystallization from ethyl acetate-hexane gave colorless prisms, mp 90–91° C.

Working Example 7

In substantially the same manner as in Working Example 1, 2-[4-[2-[(E)-2-phenylethenyl]-4-oxazolylmethoxy] phenyl]ethanol was allowed to react with 1,2,4-triazole to give 1-[2-[4-[2-[(E)-2-phenylethenyl]-4-oxazolylmethoxy] phenyl]ethyl]-1,2,4-triazole. The yield was 75%. Recrystallization from ethyl acetate-hexane gave colorless prisms, mp 136–137° C.

Working Example 8

To a solution of imidazole (70 mg) in N,N-dimethylformamide (5 ml) was added, at 0° C., sodium hydride (60%, in oil, 50 mg). The mixture was stirred for one hour. To the reaction mixture was added 3-[4-[2-[(E)-2-phenylethenyl]-4-oxazolylmethoxy]phenyl]propyl methanesulfonate (350 mg). The mixture was stirred for 1.5 hour at 70° C. The reaction mixture was diluted with water and extracted with ethyl acetate. The ethyl acetate layer was washed with water, dried (MgSO₄), and concentrated. The resulting crystalline product was recrystallized from ethyl acetate-hexane to give 4-[4-[3-(1-imidazolyl)propyl] phenoxymethyl]-2-[(E)-2-phenylethenyl]oxazole (200 mg, 61%) as colorless prisms, mp 127–128° C.

Working Example 9

In substantially the same manner as in Working Example 8, imidazole was allowed to react with 4-[4-[2-[(E)-2-phenylethenyl]-4-oxazolylmethoxy]phenyl]butyl]-methanesulfonate to give 4-[4-[4-(1-imidazolyl)butyl] phenoxymethyl]-2-[(E)-2-phenylethenyl]oxazole. The yield was 61%. Recrystallization from ethyl acetate-hexane gave colorless prisms, mp 103–104° C.

Working Example 10

In substantially the same manner as in Working Example 8, 1,2,3-triazole was allowed to react with 4-[4-[2-[(E)-2-phenylethenyl]-4-oxazolylmethoxy]phenyl]butyl methanesulfonate. The extracted mixture was subjected to a silica gel column chromatography. From the fraction eluted with ethyl acetate-hexane (2:3, v/v), 2-[4-[4-[2-[(E)-2-phenylethenyl]-4-oxazolylmethoxy]phenyl]butyl]-2H-1,2,3-triazole. The yield was 35%. Recrystallization from ethyl acetate-hexane gave colorless leaflets, mp 90–91° C.

Working Example 11

In the column chromatography in Working Example 10, from the fraction subsequently eluted with ethyl acetate-hexane (2:1, v.v), 1-[4-[4-[2-[(E)-2-phenylethenyl]-4-oxazolylmethoxy]phenyl]butyl]-1H-1,2,3-triazole was obtained. The yield was 25%. Recrystallization from ethyl acetate-hexane gave colorless needles, mp 125–126° C.

Working Example 12

In substantially the same manner as in Working Example 8, 1,2,3-triazole was allowed to react with 3-[4-[2-[(E)-2-phenylethenyl]-4-oxazolylmethoxy]phenyl]propyl methanesulfonate. The reaction mixture was subjected to a silica gel column chromatography. From the fraction eluted with ethyl acetate-hexane (1:1, v/v), 2-[3-[4-[2-[(E)-2-phenylethenyl]-4-oxazolylmethoxy]phenyl]propyl]-2H-1,2,3-triazole was obtained. The yield was 35%. Recrystallization from ethyl acetate-hexane gave colorless prisms, mp 103–104° C.

Working Example 13

In the column chromatography in Working Example 12, from the fraction eluted subsequently, 1-[3-[4-[2-[(E)-2-phenylethenyl]-4-oxazolylmethoxy]phenyl]propyl]-1H-1,2, 3-triazole was obtained. The yield was 22%. Recrystallization from ethyl acetate gave colorless needles, mp 142–143° C.

Working Example 14

In substantially the same manner as in Working Example 8, pyrazole was allowed to react with 3-[4-[2-[(E)-2-phenylethenyl]-4-oxazolylmethoxy]phenyl]propyl methanesulfonate to give 2-[(E)-2-phenylethenyl]-4-[4-3-(1-pyrazolyl)propyl]phenoxymethyl]oxazole. The yield was 67%. Recrystallization from isopropyl ether gave colorless leaflets, mp 94–95° C.

Working Example 15

In substantially the same manner as in Working Example 8, 2-methylimidazole was allowed to react with 3-[4-[2-[(E)-2-phenylethenyl]-4-oxazolylmethoxy]phenyl]propyl methanesulfonate to give 4-[4-[3-(2-methyl-1-imidazolyl)propyl]phenoxymethyl]-2-[(E)-2-phenylethenyl]oxazole. The yield was 47%. Recrystallization form ethyl acetate-hexane gave colorless prisms, mp 93–94° C.

Working Example 16

In substantially the same manner as in Working Example 8, imidazole was allowed to react with 3-[3-methoxy-4-[2-[(E)-2-phenylethenyl]-4-oxazolylmethoxy]phenyl]propyl methanesulfonate to give 4-[4-[3-(1-imidazolyl)propyl]-2-methoxyphenoxymethyl]-2-[(E)-2-phenylethenyl]oxazole. The yield was 60%. Recrystallization from ethyl acetate-hexane gave colorless prisms, m,p.95–96° C.

Working Example 17

In substantially the same manner as in Working Example 8, imidazole was allowed to react with 5-[4-[2-[(E)-2-phenylethenyl]-4-oxazolylmethoxy]phenyl]pentyl methanesulfonate to give 4-[4-[5-(1-imidazolyl)pentyl]phenoxymethyl]-2-[(E)-2-phenylethenyl]oxazole. The yield was 66%. Recrystallization from ethyl acetate-hexane gave colorless prisms, mp 101–102° C.

Working Example 18

In substantially the same manner as in Working Example 8, imidazole was allowed to react with 3-[3-[2-[(E)-2-phenylethenyl]-4-oxazolylmethoxy]phenyl]propyl methanesulfonate to give 4-[3-[3-(1-imidazolyl)propyl]phenoxymethyl]-2-[(E)-2-phenylethenyl]oxazole. The yield was 63%. Recrystallization from ethyl acetate-hexane gave colorless prisms, mp 86–87° C.

Working Example 19

In substantially the same manner as in Working Example 8, imidazole was allowed to react with 3-[2-[2-[(E)-2-phenylethenyl]-4-oxazolylmethoxy]phenyl]propyl methanesulfonate to give 4-[2-[3-(1-imidazolyl)propyl]phenoxymethyl]-2-[(E)-2-phenylethenyl]oxazole as an oily product. The yield was 80%.

NMR (δ ppm in CDCl$_3$): 2.12(2H,quint,J=7.4 Hz), 2.66 (2H,t,J=7.4 Hz), 3.94(2H,t,J=7.4 Hz), 5.04(2H,s), 6.9–7.58 (16H,m).

Working Example 20

In substantially the same manner as in Working Example 8, imidazole was allowed to react with 6-[4-[2-[(E)-2-phenylethenyl]-4-oxazolylmethoxy]phenyl]hexyl methanesulfonate to give 4-[4-[6-(1-imidazolyl)hexyl]phenoxymethyl]-2-[(E)-2-phenylethenyl]oxazole. The yield was 66%. Recrystallization from ethyl acetate-hexane gave colorless prisms, mp 108–109° C.

Working Example 21

In substantially the same manner as in Working Example 8, benzimidazole was allowed to react with 4-[4-[2-[(E)-2-phenylethenyl]-4-oxazolylmethoxy]phenyl]butyl methanesulfonate to give 1-[4-[4-[2-[(E)-2-phenylethenyl]-4-oxazolylmethoxy]phenyl]butyl]benzimidazole. The yield was 36%. Recrystallization from ethyl acetate-hexane gave colorless prisms, mp 148–149° C.

Working Example 22

In substantially the same manner as in Working Example 8, 2-methylimidazole was allowed to react with 4-[4-[2-[(E)-2-phenylethenyl]-4-oxazolylmethoxy]phenyl]butyl methanesulfonate to give 4-[4-[4-(2-methyl-1-imidazolyl)butyl]phenoxymethyl]-2-[(E)-2-phenylethenyl]oxazole. The yield was 42%. Recrystallization from ethyl acetate-hexane gave colorless prisms, mp 122–123° C.

Working Example 23

In substantially the same manner as in Working Example 8, 2-phenylimidazole was allowed to react with 4-[4-[2-[(E)-2-phenylethenyl]-4-oxazolylmethoxy]phenyl]butyl methanesulfonate to give 2-[(E)-2-phenylethenyl]-4-[4-[4-(2-phenyl-1-imidazolyl) butyl]phenoxymethyl]oxazole. The yield was 40%. Recrystallization from ethyl acetate-isopropyl ether gave colorless prisms, mp 85–86° C.

Working Example 24

In substantially the same manner as in Working Example 8, pyrrole was allowed to react with 3-[4-[2-[(E)-2-phenylethenyl]-4-oxazolylmethoxy]phenyl]propyl methansulfonate to give 2-[(E)-2-phenylethenyl]-4-[4-[3-(1-pyrrolyl)propyl]phenoxymethyl]oxazole. The yield was 57%. Recrystallization from ethyl acetate-hexane gave colorless prisms, mp 108–109° C.

Working Example 25

A mixture of 4-[4-[2-[(E)-2-phenylethenyl]-4-oxazolylmethoxy]phenyl]butyl methanesulfonate (430 mg), ethyl 2-imidazolecarboxylate (155 mg), potassium carbonate (305 mg) and N,N-dimethylformamide (10 ml) was stirred for two hours at temperatures ranging from 80 to 90° C. The reaction mixture was poured into water and extracted with ethyl acetate. The ethyl acetate layer was washed with water, dried (MgSO$_4$), and concentrated. The residue was subjected to a silica gel column chromatography. The crystalline product obtained from the fraction eluted with ethyl acetate-hexane (2:1, v/v) was recrystallized from ethyl acetate-hexane to give ethyl 1-[4-[4-[2-[(E)-2-phenylethenyl]-4-oxazolylmethoxy]phenyl]butyl]-2-imidazolecarboxylate (280 mg, 60%) as colorless prisms, mp 96–97° C.

Working Example 26

In substantially the same manner as in Working Example 25, 4-(4-chloromethylphenoxymethyl)-2-[(E)-2-phenylethenyl]oxazole was allowed to react with imidazole to give 4-[4-(1-imidazolylmethyl)phenoxymethyl]-2-[(E)-2-phenylethenyl]oxazole. Recrystallization from ethyl acetate-hexane gave colorless prisms, mp 149–150° C.

Working Example 27

In substantially the same manner as in Working Example 25, 2-[4-[2-[(E)-2-phenylethenyl]-4-oxazolylmethoxy]phenyl]ethyl methanesulfonate was allowed to react with imidazole to give 4-[4-[2-(1-imidazolyl)ethyl]phenoxymethyl]-2-[(E)-2-phenylethenyl]oxazole. The yield

Working Example 28

In substantially the same manner as in Working Example 25, 3-[4-[2-[(E)-2-phenylethenyl]-4-oxazolylmethoxy]phenyl]propyl methanesulfonate was allowed to react with benzimidazole to give 1-[3-[4-[2-[(E)-2-phenylethenyl]-4-oxazolylmethoxy]phenyl]propyl]benzimidazole. The yield was 49%. Recrystallization from ethyl acetate-hexane gave colorless prisms, mp 115–117° C.

Working Example 29

In substantially the same manner as in Working Example 25, 3-[4-[2-[(E)-2-phenylethenyl]-4-oxazolylmethoxy]phenyl]propyl methanesulfonate was allowed to react with ethyl 2-imidazolecarboxylate to give ethyl 1-[3-[4-[2-[(E)-2-phenylethenyl]-4-oxazolylmethoxy]phenyl]propyl]-2-imidazolecarboxylate. The yield was 68%. Recrystallization from ethyl acetate-hexane gave colorless prisms, mp 123–124° C.

Working Example 30

In substantially the same manner as in Working Example 25, 3-[4-[2-[(E)-2-phenylethenyl]-4-oxazolylmethoxy]phenyl]propyl methanesulfonate was allowed to react with dimethyl 4,5-imidazoledicarboxylate to give dimethyl 1-[3-[4-[2-[(E)-2-phenylethenyl]-4-oxazolylmethoxy]phenyl]propyl]-4,5-imidazoledicarboxylate. The yield was 63%. Recrystallization from ethyl acetate-hexane gave colorless prisms, mp 85–86° C.

Working Example 31

In substantially the same manner as in Working Example 25, 3-[4-[2-[(E)-2-phenylethenyl]-4-oxazolylmethoxy]phenyl]propyl methanesulfonate was allowed to react with 4,5-imidazoledicarboxamide to give 1-[3-[4-[2-[(E)-2-phenylethenyl]-4-oxazolylmethoxy]phenyl]propyl]-4,5-imidazoledicarboxamide. The yield was 44%. Recrystallization from ethyl acetate gave colorless prisms, mp 194–195° C.

Working Example 32

In substantially the same manner as in Working Example 25, 3-[4-[2-[(E)-2-phenylethenyl]-4-oxazolylmethoxy]phenyl]propyl methanesulfonate was allowed to react with 4,5-diphenylimidazole to give 4-[4-[3-(4,5-diphenyl-1-imidazolyl)propyl]phenoxymethyl]-2-[(E)-2-phenylethenyl]oxazole. The yield was 53%. Recrystallization from ethyl acetate-hexane gave colorless prisms, mp 137–138° C.

Working Example 33

A mixture of 4-(4-chloromethylphenoxymethyl)-2-[(E)-2-phenylethenyl]oxazole (500 mg), 1,2,4-triazole (160 mg), potassium carbonate (620 mg) and N,N-dimethylformamide (10 ml) was stirred for 2 hours at temperatures ranging from 80 to 90° C. The reaction mixture was poured into water and extracted with ethyl acetate. The ethyl acetate layer was washed with water, dried (MgSO$_4$), and concentrated. The residue was subjected to a silica gel column chromatography. From the fraction eluted with ethyl acetate-methanol (20:1, v/v), 1-[4-[2-[(E)-2-phenylethenyl]-4-oxazolylmethoxy]benzyl]-1H-1,2,4-triazole (430 mg, 80%). Recrystallization from ethyl acetate-hexane gave colorless prisms, mp 148–149° C.

Working Example 34

In the column chromatography in Working Example 33, from the fraction subsequently eluted, 4-[4-[2-[(E)-2-phenylethenyl]-4-oxazolylmethoxy]benzyl]-4H-1,2,4-triazole (40 mg, 7.4%) was obtained. Recrystallization from ethyl acetate gave colorless prisms, mp 209–210° C.

Working Example 35

In substantially the same manner as in Working Example 33, 3-[4-[2-[(E)-2-phenylethenyl]-4-oxazolylmethoxy]phenyl]propyl methanesulfonate was allowed to react with tetrazole, and the reaction mixture was subjected to extraction. The extract was subjected to a silica gel column chromatography. From the fraction eluted with ethyl acetate-hexane (1:1, v/v), 2-[3-[4-[2-[(E)-2-phenylethenyl]-4-oxazolylmethoxy]phenyl]propyl]-2H-tetrazole was obtained. The yield was 41%. Recrystallization from ethyl acetate-hexane gave colorless prisms, mp 97–98° C.

Working Example 36

In the column chromatography in Working Example 35, from the fraction subsequently eluted, 1-[3-[4-[2-[(E)-2-phenylethenyl]-4-oxazolylmethoxy]phenyl]propyl]-1H-tetrazole was obtained. The yield was 23%. Recrystallization from ethyl acetate gave colorless leaflets, mp 147–148° C.

Working Example 37

A mixture of 1-[4-(4-hydroxyphenyl)butyl]-1,2,4-triazole (450 mg), 4-chloromethyl-2-(3,4-dihydro-2-naphthyl)oxazole (565 mg), potassium carbonate (290 mg) and N,N-dimethylformamide (10 ml) was stirred for 6 hours at 80° C. The reaction mixture was poured into water and extracted with ethyl acetate. The ethyl acetate layer was washed with water, dried (MgSO$_4$), and concentrated. The residue was subjected to a silica gel column chromatography. A crystalline product obtained from the fraction eluted with chloroform-methanol (50:1, v/v) was recrystallized from ethyl acetate-hexane to give 1-[4-[4-[2-(3,4-dihydro-2-naphthyl)-4-oxazolylmethoxy]phenyl]butyl]-1,2,4-triazole as colorless prisms, mp 96–97° C. The yield was 49%.

Working Example 38

In substantially the same manner as in Working Example 37, 1-[4-(4-hydroxyphenyl)butyl]-1,2,4-triazole was allowed to react with 4-chloromethyl-5-methyl-2-(2-naphthyl)oxazole to give 1-[4-[4-[5-methyl-2-(2-naphthyl)-4-oxazolylmethoxy]phenyl]butyl]-1,2,4-triazole. The yield was 54%. Recrystallization from ethyl acetate-hexane gave colorless prisms, mp 134–135° C.

Working Example 39

In substantially the same manner as in Working Example 37, 1-[4-(4-hydroxyphenyl)butyl]-1,2,4-triazole was allowed to react with 2-(2-benzofranyl)-4-chloromethyl-5-methyloxazole to give 1-[4-[4-[2-(2-benzofranyl)-5-methyl-4-oxazolylmethoxy]phenyl]butyl]-1,2,4-triazole. The yield was 43%. Recrystallization from ethyl acetate-hexane gave colorless prisms, mp 105–107° C.

Working Example 40

In substantially the same manner as in Working Example 37, 1-[4-(4-hydroxyphenyl)butyl]-1,2,4-triazole was allowed to react with 2-(2-benzo[b]thienyl)-4-chloromethyl-5-methyloxazole to give 1-[4-[4-[2-(2-benzo[b]thienyl)-5-methyl-4-oxazolylmethoxy]phenyl]butyl]-1,2,4-triazole. The yield was 59%. Recrystallization from ethyl acetate-hexane gave colorless prisms, mp 131–132° C.

Working Example 41

In substantially the same manner as in Working Example 37, 1-[3-(4-hydroxy-3-methoxyphenyl)propyl]-1,2,4-triazole was allowed to react with 4-chloromethyl-2-[(E)-2-phenylethenyl]oxazole to give 1-[3-[3-methoxy-4-[2-[(E)-2-phenylethenyl]-4-oxazolylmethoxy]phenyl]propyl]-1,2,4-triazole. The yield was 62%. Recrystallization from ethyl acetate-hexane gave colorless prisms, mp 113–114° C.

Working Example 42

In substantially the same manner as in Working Example 37, 1-[3-(4-hydroxyphenyl)propyl]imidazole was allowed to react with 4-chloromethyl-2-phenyloxazole to give 4-[4-[3-(1-imidazolyl)propyl]phenoxymethyl]-2-phenyloxazole. The yield was 42%. Recrystallization from ethyl acetate-hexane gave colorless prisms, mp 111–112° C.

Working Example 43

In substantially the same manner as in Working Example 37, 1-[3-(4-hydroxyphenyl)propyl]imidazole was allowed to react with 4-chloromethyl-2-(3,4-dihydro-2-naphthyl)oxazole to give 2-(3,4-dihydro-2-naphthyl)-4-[4-[3-(1-imidazolyl)propyl]phenoxymethyl]oxazole. The yield was 42%. Recrystallization from ethyl acetate-hexane gave colorless prisms, mp 99–100° C.

Working Example 44

In substantially the same manner as in Working Example 37, 1-[3-(4-hydroxyphenyl)propyl]imidazole was allowed to react with 2-(2-benzo[b]thienyl)-4-chloromethyl-5-methyloxazole to give 2-(2-benzo[b]thienyl)-4-[4-[3-(1-imidazolyl)propyl]phenoxymethyl]-5-methyloxazole. The yield was 38%. Recrystallization from ethyl acetate-hexane gave colorless prisms, mp 142–143° C.

Working Example 45

In substantially the same manner as in Working Example 37, 1-[3-(4-hydroxyphenyl)propyl]imidazole was allowed to react with 2-benzyl-4-chloromethyloxazole to give 2-benzyl-4-[4-[3-(1-imidazolyl)propyl]phenoxymethyl]oxazole. The yield was 23%. Recrystallization from ethyl acetate-isopropyl ether gave colorless prisms, mp 61–62° C.

Working Example 46

In substantially the same manner as in Working Example 37, 1-(4-hydroxyphenyl)imidazole was allowed to react with 4-chloromethyl-2-[(E)-2-phenylethenyl]oxazole to give 4-[4-(1-imidazolyl)phenoxymethyl]-2-[(E)-2-phenylethenyl]oxazole. The yield was 68%. Recrystallization from ethyl acetate-hexane gave colorless prisms, mp 160–162° C.

Working Example 47

Sodium hydride (90 mg) was added, at room temperature, to a solution of 1-[3-(4-hydroxyphenyl)propyl]imidazole (405 mg) in N,N-dimethylformamide (10 ml). The mixture was stirred for 1.5 hour, to which was added 4-chloromethyl-2-isopropyl oxazole (350 mg). The mixture was stirred for further 4 hours at 80° C. The reaction mixture was poured into water and extracted with ethyl acetate. The ethyl acetate layer was washed with water, dried (MgSO$_4$), and concentrated. The residue was subjected to a silica gel column chromatography. From the fraction eluted with ethyl acetate-hexane-methanol (20:10:1. v/v), 4-[4-[3-(1-imidazolyl)propyl]phenoxymethyl]-2-isopropyloxazole (450 mg, 69%) as an oily product.

NMR(δ ppm in CDCl$_3$): 1.36(5H,d,J=6.8 Hz), 2.0–2.2 (2H,m), 2.56(2H,t,J=7.5 Hz), 3.0–3.2(1H,m), 3.92(2H,t,J=7 Hz), 4.96(2H,s), 6.9–7.0(3H,m), 7.0–7.1(3H,m), 7.46(1H,s), 7.59(1H,s).

Working Example 48

Sodium hydride (440 mg) was added, at room temperature, to a solution of 1-[3-(4-hydroxyphenyl)propyl]imidazole (2.02 g) in N,N-dimethylformamide (50 ml). The mixture was stirred for 1.5 hour, to which was added 2-(4-benzyloxyphenyl)-4-chloromethyloxazole (3.60 g). The mixture was stirred for further 3 hours at 80° C. The reaction mixture was poured into water and extracted with ethyl acetate. The ethyl acetate layer was washed with water, dried (MgSO$_4$), and concentrated. The residue was subjected to a silica gel column chromatography. A crystalline product obtained from the fraction eluted with ethyl acetate-methanol (50:1, v.v) was recrystallized from ethanol to give 2-(4-benzyloxyphenyl)-4-[4-[3-(1-imidazolyl)propyl]phenoxymethyl]oxazole (2.88 g, 62%) as colorless prisms, mp 133–134° C.

Working Example 49

In substantially the same manner as in Working Example 48, 1-[3-(4-hydroxyphenyl)propyl]imidazole was allowed to react with 4-chloromethyl-2-(4-chlorophenyl) oxazole to give 2-(4-chlorophenyl)-4-[4-[3-(1-imidazolyl)propyl]phenoxymethyl]oxazole. The yield was 76%. Recrystallization from ethyl acetate-hexane gave colorless prisms, mp 116–117° C.

Working Example 50

In substantially the same manner as in Working Example 48, 1-[3-(4-hydroxyphenyl)propyl]imidazole was allowed to react with 4-chloromethyl-2-(3,5-dimethoxyphenyl)oxazole to give 2-(3,5-dimethoxyphenyl)-4-[4-[3-(1-imidazolyl)propyl]phenoxymethyloxazole. The yield was 76%. Recrystallization from ethyl acetate-hexane gave colorless prisms, mp 59–60° C.

Working Example 51

In substantially the same manner as in Working example 48, 1-[3-(4-hydroxyphenyl)propyl]imidazole was allowed to react with 4-chloromethyl-2-(3,5-dimethylphenyl)oxazole to give 2-(3,5-dimethylphenyl)-4-[4-[3-(1-(imidazolyl)propyl]phenoxymethyl]oxazole. The yield was 74%. Recrystallization from ethyl acetate-hexane gave colorless prisms, mp 110–111° C.

Working Example 52

In substantially the same manner as in Working Example 48, 1-[3-(4-hydroxyphenyl)propyl]imidazole was allowed to react with 4-chloromethyl-2-(4-cyanophenyl) oxazole to give 2-(4-cyanophenyl)-4-[4-[3-(1-imidazolyl)propyl]phenoxymethyl]oxazole. The yield was 72%. Recrystallization from ethyl acetate-hexane gave colorless prisms, mp 98–99° C.

Working Example 53

In substantially the same manner as in Working Example 48, 1-[3-(4-hydroxyphenyl)propyl]imidazole was allowed to react with 2-(3-benzyloxyphenyl)-4-chloromethyloxazole to give 2-(3-benzyloxyphenyl)-4-[4-[3-(1-imidazolyl)propyl] phenoxymethyl]oxazole. The yield was 65%. Recrystallization from ethyl acetate-hexane gave colorless prisms, mp 112–113° C.

Working Example 54

In substantially the same manner as in Working Example 48, 1-[3-(4-hydroxyphenyl)propyl]imidazole was allowed to react with 4-chloromethyl-2-cyclohexyloxazole to give 2-cyclohexyl-4-[4-[3-(1-imidazolyl)propyl]phenoxymethyl] oxazole. The yield was 38%. Recrystallization from ether-hexane gave colorless prisms, mp 46–47° C.

Working Example 55

In substantially the same manner as in Working Example 48, 1-[3-(4-hydroxyphenyl)propyl]imidazole was allowed to react with 4-chloromethyl-5-methyl-2-[(E)-2-phenylethenyl]oxazole to give 4-[4-[3-(1-imidazolyl) propyl)phenoxymethyl]-5-methyl-2-[(E)-2-phenylethenyl] oxazole. The yield was 66%. Recrystallization from ethyl acetate-hexane gave pale yellow prisms, mp 94–95° C.

Working Example 56

In substantially the same manner as in Working Example 48, 1-[3-(4-hydroxyphenyl)propyl]imidazole was allowed to react with 4-chloromethyl-2-[(E)-2-phenylethenyl]thiazole to give 4-[4-[3-(1-imidazolyl)propyl]phenoxymethyl]-2-[(E)-2-phenylethenyl]thiazole. The yield was 58%. Recrystallization from ethyl acetate gave colorless prisms, mp 129–130° C.

Working Example 57

In substantially the same manner as in Working Example 48, 1-[3-(4-hydroxyphenyl)propyl]imidazole was allowed to react with 5-chloromethyl-2-isopropyl benzoxazole to give 5-[4-[3-(1-imidazolyl)propyl]phenoxymethyl]-2-isopropyl-benzoxazole. The yield was 59%. Recrystallization from ethyl acetate-hexane gave colorless prisms, mp 76–77° C.

Working Example 58

A mixture of ethyl 1-[3-[4-[2-[(E)-2-phenylethenyl]-4-oxazolylmethoxy]phenyl]propyl]-2-imidazolecarboxylate (300 mg), 1N aqueous sodium hydroxide (1.32 ml) and tetrahydrofuran (3 ml) was stirred for 2 hours at room temperature. To the reaction mixture were added 1N hydrochloric acid (1.32 ml) and then water. The resulting crystalline precipitate was collected by filtration and washed with ether. Recrystallization from tetrahydrofuran gave 1-[3-[4-[2-[(E)-2-phenylethenyl]-4-oxazolylmethoxy]-phenyl] propyl]-2-imidazolecarboxylic acid (176 mg, 63%) as colorless prisms, mp 116° C. (decomp.).

Working Example 59

In substantially the same manner as in Working Example 58, dimethyl 1-[3-[4-[2-[(E)-2-phenylethenyl]-4-oxazolylmethoxy]phenyl]propyl]-4,5-imidazole-dicarboxylate was subjected to hydrolysis to give 1-[3-[4-[2-[(E)-2-phenylethenyl]-4-oxazolylmethoxy]phenyl] propyl]-4,5-imidazoledicarboxylic acid. The yield was 26%. Recrystallization from acetone-methanol gave colorless prisms, mp 216° C. (decomp.).

Working Example 60

To a suspension of lithium aluminum hydride (25 mg) in ether (5 ml) was added dropwise, under ice-cooling, a solution of ethyl 1-[3-[4-[2-[(E)-2-phenylethenyl]-4-oxazolylmethoxy]phenyl]propyl]-2-imidazolecarboxylate (300 mg) in ether (5 mg)— tetrahydrofuran (10 ml). The mixture was stirred for one hour, to which was added 4N aqueous sodium hydroxide (0.025 ml). The mixture was stirred for 30 minutes at room temperature. The reaction mixture was poured into water, which was subjected to extraction with ethyl acetate. The ethyl acetate layer was washed with water, dried (MgSO$_4$), and concentrated to leave a crystalline product. Recrystallization from ethyl acetate-hexane gave 1-[3-[4-[2-[(E)-2-phenylethenyl]-4-oxazolyl-methoxy]phenyl]propyl]-2-imidazolemethanol (160 mg, 58%) as colorless prisms, mp 143–144° C.

Working Example 61

In substantially the same manner as in Working Example 60, dimethyl 1-[3-[4-[2-[(E)-2-phenylethenyl]-4-oxazolylmethoxy]phenyl]propyl]-4,5-imidazole-dicarboxylate was subjected to reduction to give 1-[3-[4-[2-[(E)-2-phenylethenyl]-4-oxazolylmethoxy]phenyl]propyl]-4,5-imidazoledimethanol. The yield was 9%. Recrystallization from ethyl acetate-hexane gave colorless prisms, mp 146–148° C.

Working Example 62

To a solution of 4-[4-[3-(1-imidazolyl)propyl]-phenoxymethyl]-2-[(E)-2-phenylethenyl]oxazole (300 mg) in ethanol (100 ml) was added palladium-carbon (5%, wet, 300 mg). The mixture was subjected to catalytic hydrogenation at room temperature under atmospheric pressure. The catalyst was filtered off. The filtrate was concentrated to leave a crystalline product, which was recrystallized from ethyl acetate-hexane to give 4-[4-[3-(1-imidazolyl)propyl] phenoxymethyl]-2-(2-phenylethyl)oxazole (170 mg, 57%) as colorless prisms, mp 67–68° C.

Working Example 63

In substantially the same manner as in Working Example 62, 2-(4-benzyloxyphenyl)-4-[4-[3-(1-imidazolyl)propyl] phenoxymethyl]oxazole was subjected to catalytic hydrogenation to give 2-(4-hydroxyphenyl)-4-[4-[3-(1-imidazolyl) propyl]phenoxymethyl]oxazole. The yield was 60%. Recrystallization from ethanol gave colorless prisms, mp 182–183° C.

Working Example 64

In substantially the same manner as in Working Example 62, 2-(3-benzyloxyphenyl)-4-[4-[3-1-imidazolyl)propyl] phenoxymethyl]oxazole was subjected to catalytic hydrogenation to give 2-(3-hydroxyphenyl)-4-[4-[3-(1-imidazolyl) propyl]phenoxymethyl]oxazole. The yield was 42%. Recrystallization from ethanol gave colorless prisms, mp 164–165° C.

Working Example 65

A mixture of 2-(4-cyanophenyl)-4-[4-[3-(1-imidazolyl) propyl]phenoxymethyl]oxazole (700 mg), sodium azide (585 mg), ammonium chloride (480 mg) and N,N-dimethylformamide (20 ml) was stirred for 24 hours at temperatures ranging from 130 to 135° C. The reaction mixture was poured into water, which was neutralized with 1N hydrochloric acid. The resulting crystalline precipitate was collected by filtration. The filtrate was subjected to extraction with ethyl acetate-tetrahydrofuran. The organic layer was washed with water, dried (MgSO$_4$), and concentrated to leave a crystalline product. Both crystalline products were combined and recrystallized from methanol to give 5-[4-[4-[4-[3-(1-imidazolyl)propyl]phenoxymethyl]-2-oxazolyl]phenyl]-1H-tetrazole (250 mg, 33%) as colorless prisms, mp 273–275° C. (decomp.).

Working Example 66

In substantially the same manner as in Working Example 48, 1-[3-(4-hydroxyphenyl)propyl]imidazole was allowed to react with 4-chloromethyl-2-(2-naphthyl)-oxazole to give 4-[4-[3-(1-imidazolyl)propyl]phenoxymethyl]-2-(2-naphthyl)oxazole. The yield was 77%. Recrystallization from ethyl acetate-hexane gave colorless prisms, mp 131–132° C.

Working Example 67

In substantially the same manner as in Working Example 48, 1-[3-(4-hydroxyphenyl)propyl]imidazole was allowed to react with 2-(2-benzo[b]thienyl)-4-chloromethyloxazole to give 2-(2-benzo[b]thienyl)-4-[4-[3-(1-imidazolyl)propyl]phenoxymethyl]oxazole. The yield was 68%. Recrystallization from ethyl acetate-hexane gave colorless prisms, mp 149–150° C.

Working Example 68

In substantially the same manner as in Working Example 47, 1-[3-(4-hydroxyphenyl)propyl]imidazole was allowed to react with ethyl 4-chloromethyl-2-oxazole-propionate to give ethyl 4-[4-[3-(1-imidazolyl)propyl]phenoxymethyl]-2-oxazolepropionate as an oily product. The yield was 70%.

NMR(δ ppm in CDCl$_3$): 1.25(3H,t,J=7 Hz), 2.0–2.2(2H, m), 2.56(2H,t,J=7.5 Hz), 2.82(2H,t,J=7 Hz), 3.11(2H,t,J=7 Hz), 3.92(2H,t,J=7 Hz), 4.16(2H,q,J=7 Hz), 4.94(2H,s), 6.85–6.95(3H,m), 7.0–7.1(3H,m), 7.46(1H,s), 7.59(1H,s)

Working Example 69

In substantially the same manner as in Working Example 47, 1-[3-(4-hydroxyphenyl)propyl]imidazole was allowed to react with 4-chloromethyl-2-(2,2-diphenyl ethenyl)oxazole to give 2-(2,2-diphenylethenyl)-4-[4-[3-(1-imidazolyl)propyl]phenoxymethyl]oxazole as an oily product. The yield was 88%.

NMR(δ ppm in CDCl$_3$): 2.0–2.2(2H,m), 2.56(2H,t,J=7.5 Hz), 3.92(2H,t,J=7 Hz), 4.95(2H,s), 6.85–7.0(4H,m), 7.0–7.1(3H,m), 7.2–7.5(10H,m)

Working Example 70

In substantially the same manner as in Working Example 60, ethyl 4-[4-[3-(1-imidazolyl)propyl]phenoxymethyl]-2-oxazolepropionate was subjected to reduction to give 4-[4-[3-(1-imidazolyl)propyl]phenoxymethyl]-2-oxazolepropanol. The yield was 80%. Recrystallization from ethyl acetate-hexane gave colorless prisms, mp 63–64° C.

Working Example 71

In substantially the same manner as in Working Example 62, 2-(2,2-diphenylethenyl)-4-[4-[3-(1-imidazolyl)propyl]phenoxymethyl]oxazole was subjected to catalytic hydrogenation to give 2-(2,2-diphenylethyl)-4-[4-[3-(1-imidazolyl)propyl]phenoxymethyl]oxazole. The yield was 82%. Recrystallization from ethyl acetate-hexane gave colorless prisms, mp 79–80° C.

Working Example 72

Sodium hydride (90 mg) was added to a solution of 1-[3-(4-hydroxyphenyl)propyl]imidazole (405 mg) in N,N-dimethyl formamide at room temperature and stirred for 1.5 hours. 4-Chloromethyl-2-(2-thienyl)oxazole (480 mg) was added, and the resultant was stirred at 90° C. for further 2 hours. The reaction mixture was poured into water, and extracted with ethyl acetate. The ethyl acetate layer was washed with water, dried (MgSO$_4$), and concentrated under reduced pressure. The residue was subjected to a silica gel chromatography. From the fraction eluted with ethyl acetate-methanol (50:1, v/v), 4-[4-[3-(1-imidazolyl)propyl]phenoxymethyl]-2-(2-thienyl)oxazole (650 mg, 89%) was obtained. Recrystallization from ethyl acetate-hexane gave colorless prisms, mp 84–85° C.

Working Example 73

In substantially the same manner as in Working Example 72, 1-[3-(4-hydroxyphenyl)propyl]imidazole was allowed to react with 4-chloromethyl-2-(1-propenyl)oxazole to give 4-[4-[3-(1-imidazolyl)propyl]phenozymethyl]-2-(1-propenyl)oxazole. The yield was 31%. Recrystallization from ethyl acetate-hexane gave pale yellow prisms, mp 61–62° C.

Working Example 74

In substantially the same manner as in Working Example 72, 1-[3-(4-hydroxyphenyl)propyl]imidazole was allowed to react with 4-chloromethyl-2-[(E)-2-cyclohexylethenyl] oxazole to give 2-[(E)-2-cyclohexylethenyl]-4-[4-[3-(1-imidazolyl)propyl]phenoxymethyl]oxazole. The yield was 67%. Recrystallization from isopropylether gave colorless prisms, mp 62–63° C.

Working Example 75

In substantially the same manner as in Working Example 72, 1-[3-(4-hydroxyphenyl)propyl]imidazole was allowed to react with 2-(4-benzoylphenyl)-4-chloromethyloxazole to give 2-(4-benzoylphenyl)-4-[4-[3-(1-imidazolyl)propyl] phenoxymethyl]oxazole. The yield was 78%. Recrystallization from ethyl acetate-hexane gave colorless prisms, mp 112–113° C.

Working Example 76

In substantially the same manner as in Working Example 72, 1-[3-(4-hydroxyphenyl)propyl]imidazole was allowed to react with 2-(2-benzofuranyl)-4-chloromethyl oxazole to give 2-(2-benzofuranyl)-4-[4-[3-(1-imidazolyl)propyl] phenoxymethyl]oxazole. The yield was 85%. Recrystallization from ethyl acetate-hexane gave colorless prisms, mp 122–123° C.

Working Example 77

In substantially the same manner as in Working Example 72, 1-[3-(4-hydroxyphenyl)propyl]imidazole was allowed to react with 4-chloromethyl-2-(9-fluorenone-2-yl)oxazole to give 2-(9-fluorenone-2-yl)-4-[4-[3-(1-imidazolyl)propyl] phenoxymethyl]oxazole. The yield was 86%. Recrystallization from ethanol gave yellow needles, mp 153–154° C.

Working Example 78

In substantially the same manner as in Working Example 72, 1-[3-(4-hydroxyphenyl)propyl]imidazole was allowed to react with 4-chloromethyl-2-(9-fluorenylidene) methyloxazole to give 2-(9-fluorenylidenemethyl)-4-[4-[3-(1-imidazolyl)propyl]phenoxymethyl]oxazole. The yield was 84%. Recrystallization from ethyl acetate gave yellow prisms, mp 116–117° C.

Working Example 79

In substantially the same manner as in Working Example 72, 1-[3-(4-hydroxyphenyl)propyl]imidazole was allowed to react with 2-chloromethyl-5-phenylbenzoxazole to give 2-[4-[3-(1-imidazolyl)propyl]phenoxymethyl]-5-phenylbenzoxazole. The yield was 77%. Recrystallization from ethyl acetate-hexane gave pale yellow plates, mp 123–124° C.

Working Example 80

In substantially the same manner as in Working Example 72, 1-[4-(4-hydroxyphenyl)butyl]imidazole was allowed to react with 5-chloromethyl-2-(2-thienyl)benzoxazole to give 5-[4-[4-(1-imidazolyl)butyl]phenoxymethyl]-2-(2-thienyl) benzoxazole. The yield was 81%. Recrystallization from ethyl acetate-hexane gave colorless prisms, mp 130–131° C.

Working Example 81

In substantially the same manner as in Working Example 72, 1-[3-(3-hydroxyphenyl)propyl]imidazole was allowed to react with 4-chloromethyl-2-(2-thienyl)oxazole to give 4-[3-[3-(1-imidazolyl)propyl]phenoxymethyl]-2-(2-thienyl) oxazole, oily substance. The yield was 78%.

NMR(δ ppm in $CDCl_3$): 2.0–2.2(2H,m), 2.60(2H,t,J=7.4 Hz), 3.92(2H,t,J=7 Hz), 5.04(2H,d,J=0.8 Hz), 6.75–6.9(4H, m), 7.05–7.3(3H,m), 7.4–7.5(2H,m), 7.65–7.7(2H,m).

This oily substance was dissolved in methanol (1 ml), to which 4N-hydrochloric acid-ethyl acetate was added, and stirred for 10 minutes. The reaction mixture was concentrated, and crystallized from diethyl ether. Recrystallization from ethyl acetate gave colorless prisms, mp 112–113° C.

Working Example 82

In substantially the same manner as in Working Example 72, 1-[3-(3-hydroxyphenyl)propyl]imidazole was allowed to react with 4-chloromethyl-2-(5-methyl-2-thienyl)oxazole to give 4-[3-[3-(1-imidazolyl)propyl]phenoxymethyl]-2-(5-methyl-2-thienyl)oxazole. The yield was 71%. Oily substance.

NMR(δ ppm in $CDCl_3$): 2.0–2.2(2H,m), 2.54(3H,d,J=0.8 Hz), 2.60(2H,t,J=7.5 Hz), 3.93(2H,t,J=7 Hz), 5.03(2H,d,J= 0.7 Hz), 6.75–6.95(5H,m), 7.07(1H,br s), 7.15–7.25(1H,m), 7.45–7.65(2H,m), 7.63(1H,t,J=0.7 Hz).

Working Example 83

In substantially the same manner as in Working Example 72, 1-[3-(3-hydroxyphenyl)propyl]imidazole was allowed to react with 2-(4-benzoylphenyl)-4-chloromethyloxazole to gave 2-(4-benzoylphenyl)-4-[3-[3-(1-imidazolyl)propyl] phenoxymethyl]oxazole. The yield was 85%. Recrystallization from ethyl acetate-hexane gave colorless prisms, mp 97–98° C.

Working Example 84

In substantially the same manner as in Working Example 72, 1-[3-(3-hydroxyphenyl)propyl]imidazole was allowed to react with 2-(4-benzyloxyphenyl)-4-chloromethyloxazole to give 2-(4-benzyloxyphenyl)-4-[3-[3-(1-imidazolyl)propyl]phenoxymethyl]oxazole. The yield was 81%. Recrystallization from ethyl acetate-hexane gave colorless prisms, mp 144–145° C.

Working Example 85

In substantially the same manner as in Working Example 72, 1-[4-(3-hydroxyphenyl)butyl]imidazole was allowed to react with 4-chloromethyl-2-[(E)-2-phenylethenyl]oxazole to give 4-[3-[4-(1-imidazolyl)butyl]phenoxymethyl]-2-[(E)-2-phenylethenyl]oxazole. The yield was 70%. Recrystallization from ethyl acetate-hexane gave colorless prisms, mp 75–76° C.

Working Example 86

In substantially the same manner as in Working Example 72, 1-[4-(3-hydroxyphenyl)butyl]imidazole was allowed to react with 2-(4-benzyloxyphenyl)-4-chloromethyloxazole to give 2-(4-benzyloxyphenyl)-4-[3-[4-(1-imidazolyl)butyl] phenoxymethyl]oxazole. The yield was 78%. Recrystallization from ethyl acetate-hexane gave colorless prisms, mp 87–88° C.

Working Example 87

In substantially the same manner as in Working Example 72, 1-[4-(4-hydroxyphenyl)butyl]imidazole was allowed to react with 4-chloromethyl-2-phenyloxazole to give 4-[4-[4-(1-imidazolyl)butyl]phenoxymethyl]-2-phenyloxazole. The yield was 89%. Recrystallization from ethyl acetate-hexane gave colorless prisms, mp 113–114° C.

Working Example 88

In substantially the same manner as in Working Example 72, 1-[3-(3-hydroxyphenyl)propyl]imidazole was allowed to react with 4-chloromethyl-2-phenyloxazole to give 4-[3-[3-(1-imidazolyl)propyl]phenoxymethyl]-2-phenyloxazole. The yield was 78%. Recrystallization from ethyl acetate-hexane gave colorless prisms, mp 62–63° C.

Working Example 89

In substantially the same manner as in Working Example 72, 1-[3-(3-hydroxyphenyl)propyl]imidazole was allowed to react with 5-chloromethyl-2-(2-thienyl)benzoxazole to give 5-[3-[3-(1-imidazolyl)propyl]phenoxymethyl]-2-(2-thienyl) benzoxazole. The yield was 76%. Recrystallization from ethyl acetate-hexane gave colorless prisms, mp 86–87° C.

Working Example 90

In substantially the same manner as in Working Example 72, 1-[4-(3-hydroxyphenyl)butyl]imidazole was allowed to react with 5-chloromethyl-2-(2-thienyl)benzoxazole to give 5-[3-[4-(1-imidazolyl)butyl]phenoxymethyl]-2-(2-thienyl) benzoxazole. The yield was 70%. Recrystallization from ethyl acetate-hexane gave colorless prisms, mp 97–98° C.

Working Example 91

In substantially the same manner as in Working Example 72, 1-[3-(4-hydroxyphenyl)propyl]imidazole was allowed to react with 4-chloromethyl-2-phenylthiazole to give 4-[4-[3-(1-imidazolyl)propyl]phenoxymethyl]-2-phenylthiazole. The yield was 78%. Recrystallization from ethyl acetate-hexane gave colorless prisms, mp 110–111° C.

Working Example 92

In substantially the same manner as in Working Example 72, 1-[4-(4-hydroxyphenyl)butyl]imidazole was allowed to react with 4-chloromethyl-2-phenylthiazole to give 4-[4-[4-(1-imidazolyl)butyl]phenoxymethyl]-2-phenylthiazole. The yield was 91%. Recrystallization from ethyl acetate-hexane gave colorless prisms, mp 93–94° C.

Working Example 93

In substantially the same manner as in Working Example 72, 1-[3-(3-hydroxyphenyl)propyl]imidazole was allowed to react with 4-chloromethyl-2-phenylthiazole to give 4-[3-[3-(1-imidazolyl)propyl]phenoxymethyl]-2-phenylthiazole. The yield was 81%. Recrystallization from ethyl acetate-hexane gave colorless prisms, mp 63–64° C.

Working Example 94

In substantially the same manner as in Working Example 72, 1-[3-(4-hydroxyphenyl)propyl]imidazole was allowed to react with 4-chloromethyl-2-(2-thienyl)thiazole to give 4-[4-[3-(1-imidazolyl)propyl]phenoxymethyl]-2-(2-thienyl)thiazole. The yield was 79%. Recrystallization from ethyl acetate-hexane gave colorless prisms, mp 76–77° C.

Working Example 95

In substantially the same manner as in Working Example 72, 1-[3-(4-hydroxyphenyl)propyl]imidazole was allowed to react with 4-chloromethyl-2-(3-methyl-2-thienyl)oxazole to give 4-[4-[3-(1-imidazolyl)propyl]phenoxymethyl]-2-(3-methyl-2-thienyl)oxazole. The yield was 78%. Recrystallization from ethyl acetate-hexane gave colorless prisms, mp 72–73° C.

Working Example 96

In substantially the same manner as in Working Example 72, 1-[4-(4-hydroxyphenyl)butyl]imidazole was allowed to react with 4-chloromethyl-2-(3-methyl-2-thienyl)oxazole to give 4-[4-[4-(1-imidazolyl)butyl]phenoxymethyl]-2-(3-methyl-2-thienyl)oxazole. The yield was 87%. Recrystallization from ethyl acetate-hexane gave colorless prisms, mp 88–89° C.

Working Example 97

In substantially the same manner as in Working Example 72, 1-[3-(4-hydroxyphenyl)propyl]imidazole was allowed to react with 4-chloromethyl-2-(5-ethyl-2-thienyl)oxazole to give 2-(5-ethyl-2-thienyl)-4-[4-[3-(1-imidazolyl)propyl]phenoxymethyl]oxazole. The yield was 55%. Recrystallization from ethyl acetate-hexane gave colorless prisms, mp 57–58° C.

Working Example 98

In substantially the same manner as in Working Example 72, 1-[3-(4-hydroxyphenyl)propyl]imidazole was allowed to react with 4-chloromethyl-2-(4,5,6,7-tetrahydro-2-benzothienyl)oxazole to give 4-[4-[3-(1-imidazolyl)propyl]phenoxymethyl]-2-(4,5,6,7-tetrahydro-2-benzothienyl)oxazole. The yield was 70%. Recrystallization from ethyl acetate-hexane gave colorless prisms, mp 83–84° C.

Working Example 99

In substantially the same manner as in Working Example 72, 1-[3-(4-hydroxyphenyl)propyl]imidazole was allowed to react with 2-(5-bromo-4-methyl-2-thienyl)-4-chloromethyloxazole to give 2-(5-bromo-4-methyl-2-thienyl)-4-[4-[3-(1-imidazolyl)propyl]phenoxymethyl]oxazole. The yield was 77%. Recrystallization from ethyl acetate-hexane gave colorless prisms, mp 92–93° C.

Working Example 100

In substantially the same manner as in Working Example 72, 1-[4-(4-hydroxyphenyl)butyl]imidazole was allowed to react with 2-(5-bromo-4-methyl-2-thienyl)-4-chloromethyloxazole to give 2-(5-bromo-4-methyl-2-thienyl)-4-[4-[4-(1-imidazolyl)butyl]phenoxymethyl]oxazole. The yield was 93%. Recrystallization from ethyl acetate-hexane gave colorless prisms, mp 85–86° C.

Working Example 101

In substantially the same manner as in Working Example 72, 1-[3-(4-hydroxyphenyl)propyl]imidazole was allowed to react with 4-chloromethyl-5-methyl-2-(2-thienyl)oxazole to give 4-[4-[3-(1-imidazolyl)propyl]phenoxymethyl]-5-methyl-2-(2-thienyl)oxazole. The yield was 84%. Recrystallization from acetone-isopropyl ether gave colorless prisms, mp 102–103° C.

Working Example 102

In substantially the same manner as in Working Example 72, 1-[3-(4-hydroxyphenyl)butyl]imidazole was allowed to react with 4-chloromethyl-5-methyl-2-(2-thienyl)oxazole to give 4-[4-[4-(1-imidazolyl)butyl]phenoxymethyl]-5-methyl-2-(2-thienyl)oxazole. The yield was 81%. Recrystallization from acetone-isopropyl ether gave colorless prisms, mp 85–86° C.

Working Example 103

In substantially the same manner as in Working Example 72, 1-[3-(4-hydroxyphenyl)propyl]imidazole was allowed to react with 4-chloromethyl-2-(2-furyl)-5-methyloxazole to give 2-(2-furyl)-4-[4-[3-(1-imidazolyl)propyl]phenoxymethyl]-5-methyloxazole. The yield was 79%. Recrystallization from acetone-isopropyl ether gave colorless prisms, mp 89–90° C.

Working Example 104

In substantially the same manner as in Working Example 72, 1-[3-(4-hydroxyphenyl)propyl]imidazole was allowed to react with 4-chloromethyl-2-[(E)-2-(2-thienyl)ethenyl]oxazole to give 4-[4-[3-(1-imidazolyl)propyl]phenoxymethyl]-2-[(E)-2-(2-thienyl)ethenyl]oxazole. The yield was 92%. Recrystallization from ethyl acetate-isopropyl ether gave colorless prisms, mp 131–132° C.

Working Example 105

In substantially the same manner as in Working Example 72, 1-[3-(4-hydroxyphenyl)propyl]imidazole was allowed to react with 4-chloromethyl-2-[(E)-2-(2-furyl)ethenyl]oxazole to give 2-[(E)-2-(2-furyl)ethenyl]-4-[4-[3-(1-imidazolyl)propyl]phenoxymethyl]oxazole. The yield was 70%. Recrystallization from ethyl acetate-hexane gave colorless prisms, mp 122–123° C.

Working Example 106

In substantially the same manner as in Working Example 72, 1-[3-(4-hydroxyphenyl)propyl]imidazole was allowed to react with 2-(5-chloro-2-furyl)-4-chloromethyloxazole to give 2-(5-chloro-2-furyl)-4-[4-[3-(1-imidazolyl)propyl]phenoxymethyl]oxazole. The yield was 86%. Recrystallization from ethyl acetate-isopropyl ether gave colorless prisms, mp 88–89° C.

Working Example 107

In substantially the same manner as in Working Example 72, 1-[3-(4-hydroxyphenyl)propyl]imidazole was allowed to react with 2-(5-bromo-2-furyl)-4-chloromethyloxazole to give 2-(5-bromo-2-furyl)-4-[4-[3-(1-imidazolyl)propyl] phenoxymethyl]oxazole. The yield was 87%. Recrystallization from ethyl acetate-isopropyl ether gave colorless needles, mp 115–116° C.

Working Example 108

In substantially the same manner as in Working Example 72, 1-[3-(4-hydroxyphenyl)propyl]imidazole was allowed to react with 4-chloromethyl-2-(5-methyl-2-furyl)oxazole to give 4-[4-[3-(1-imidazolyl)propyl]phenoxymethyl]-2-(5-methyl-2-furyl)oxazole. The yield was 94%. Recrystallization from ethyl acetate-isopropyl ether gave colorless prisms, mp 109–110° C.

Working Example 109

A mixture of 1-[3-(4-hydroxyphenyl)propyl]imidazole (465 mg), 4-chloromethyl-2-(5-methyl-2-thienyl)oxazole (600 mg), potassium carbonate (315 mg) and N,N-dimethylformamide (15 ml) was stirred at 80° C. for 14 hours. The reaction mixture was poured into water, and extracted with ethyl acetate. The ethyl acetate layer was washed with water, dried (MgSO$_4$), and concentrated under reduced pressure. The residue was subjected to a silica gel column chromatography. From the fraction eluted with ethyl acetate-methanol (20:1, v/v), crystals of 4-[4-[3-(1-imidazolyl)propyl]phenoxymethyl]-2-(5-methyl-2-thienyl) oxazole (490 mg, 56%) was obtained. Recrystallization from ethyl acetate-hexane gave colorless prisms, mp 83–84° C.

Working Example 110

In substantially the same manner as in Working Example 109, 1-[3-(4-hydroxyphenyl)propyl]imidazole was allowed to react with 4-chloromethyl-2-(5-chloro-2-thienyl)oxazole to give 2-(5-chloro-2-thienyl)-4-[4-[3-(1-imidazolyl)propyl] phenoxymethyl]oxazole. The yield was 68%. Recrystallization from ethyl acetate-hexane gave colorless prisms, mp 77–78° C.

Working Example 111

In substantially the same manner as in Working Example 109, 1-[3-(4-hydroxyphenyl)propyl]imidazole was allowed to react with 4-chloromethyl-2-(3-thienyl)oxazole to give 4-[4-[3-(1-imidazolyl)propyl]phenoxymethyl]-2-(3-thienyl) oxazole. The yield was 65%. Recrystallization from ethyl acetate-hexane gave colorless prisms, mp 102–103° C.

Working Example 112

In substantially the same manner as in Working Example 109, 1-[3-(4-hydroxyphenyl)propyl]imidazole was allowed to react with 4-chloromethyl-2-(2-furyl)oxazole to give 2-(2-furyl)-4-[4-[3-(1-imidazolyl)propyl]phenoxymethyl] oxazole. The yield was 31%. Recrystallization from ethyl acetate-hexane gave colorless prisms, mp 92–93° C.

Working Example 113

In substantially the same manner as in Working Example 109, 1-[3-(4-hydroxyphenyl)propyl]imidazole was allowed to react with 2-chloromethylbenzoxazole to give 2-[4-[3-(1-imidazolyl)propyl]phenoxymethyl]benzoxazole. The yield was 28%. Recrystallization from ethyl acetate-hexane gave pale brown prisms, mp 81–82° C.

Working Example 114

In substantially the same manner as in Working Example 109, 1-[3-(4-hydroxyphenyl)propyl]imidazole was allowed to react with 5-chloromethyl-2-(2-thienyl)benzoxazole to give 5-[4-[3-(1-imidazolyl)propyl]phenoxymethyl]-2-(2-thienyl)benzoxazole. The yield was 53%. Recrystallization from ethyl acetate-hexane gave colorless prisms, mp 130–131° C.

Working Example 115

In substantially the same manner as in Working Example 109, 1-[3-(4-hydroxyphenyl)propyl]imidazole was allowed to react with 5-(4-chloromethyl-2-oxazolyl)-2-phenylbenzoxazole to give 5-[4-[4-[3-(1-imidazolyl)propyl] phenoxymethyl]-2-oxazolyl]-2-phenylbenzoxazole. The yield was 53%. Recrystallization from ethyl acetate-hexane gave pale yellow prisms, mp 166–167° C.

Working Example 116

In substantially the same manner as in Working Example 109, 1-[3-(4-hydroxyphenyl)propyl]imidazole was allowed to react with 4-chloromethyl-2-(5-phenyl-2-benzothienyl) oxazole to give 4-[4-[3-(1-imidazolyl)propyl] phenoxymethyl]-2-(5-phenyl-2-benzothienyl)oxazole. The yield was 67%. Recrystallization from ethyl acetate-hexane gave colorless prisms, mp 168–169° C.

Working Example 117

In substantially the same manner as in Working Example 109, 1-[3-(4-hydroxyphenyl)propyl]imidazole was allowed to react with 5-chloromethyl-2-phenylbezoxazole to give 5-[4-[3-(1-imidazolyl)propyl]phenoxymethyl]-2-phenylbenzoxazole. The yield was 67%. Recrystallization from ethyl acetate-hexane gave colorless prisms, mp 137–138° C.

Working Example 118

In substantially the same manner as in Working Example 109, 1-[3-(4-hydroxyphenyl)propyl]imidazole was allowed to react with 2-benzyloxy-5-chloromethylpyridine to give 2-benzyloxy-5-[4-[3-(1-imidazolyl)propyl]phenoxymethyl] pyridine. The yield was 65%. Recrystallization from ethyl acetate-hexane gave colorless prisms, mp 84–85° C.

Working Example 119

In substantially the same manner as in Working Example 109, 1-[3-(4-hydroxyphenyl)propyl]imidazole was allowed to react with 3-chloromethyl-7-phenylquinoline to give 3-[4-[3-(1-imidazolyl)propyl]phenoxymethyl]-7-phenylquinoline. The yield was 59%. Recrystallization from ethanol gave colorless prisms, mp 135–136° C.

Working Example 120

In substantially the same manner as in Working Example 109, 1-[3-(4-hydroxyphenyl)propyl]imidazole was allowed to react with 6-bromo-2-chloromethylimidazo[1,2-a] pyridine to give 6-bromo-2-[4-[3-(1-imidazolyl)propyl] phenoxymethyl]imidazo[1,2-a]pyridine. The yield was 57%. Recrystallization from ethyl acetate-hexane gave colorless prisms, mp 103–104° C.

Working Example 121

In substantially the same manner as in Working Example 109, 1-[4-(4-hydroxyphenyl)butyl]imidazole was allowed to react with 4-chloromethyl-2-(2-thienyl)oxazole to give 4-[4-[4-(1-imidazolyl)butyl]phenoxymethyl]-2-(2-thienyl) oxazole. The yield was 61%. Recrystallization from ethyl acetate-hexane gave colorless prisms, mp 106–107° C.

Working Example 122

In substantially the same manner as in Working Example 109, 1-[4-(4-hydroxyphenyl)butyl]imidazole was allowed to react with 4-chloromethyl-2-(5-methyl-2-thienyl)oxazole to give 4-[4-[4-(1-imidazolyl)butyl]phenoxymethyl]-2-(5-methyl-2-thienyl)oxazole. The yield was 65%. Recrystallization from ethyl acetate-hexane gave colorless prisms, mp 82–83° C.

Working Example 123

In substantially the same manner as in Working Example 109, 1-[4-(4-hydroxyphenyl)butyl]imidazole was allowed to react with 2-(4-benzoylphenyl)-4-chloromethyloxazole to give 2-(4-benzoylphenyl)-4-[4-[4-(1-imidazolyl)butyl]phenoxymethyl]oxazole. The yield was 64%. Recrystallization from ethyl acetate-hexane gave colorless prisms, mp 91–92° C.

Working Example 124

In substantially the same manner as in Working Example 109, 1-[4-(4-hydroxyphenyl)butyl]imidazole was allowed to react with 2-(4-benzyloxyphenyl)-4-chloromethyloxazole to give 2-(4-benzyloxyphenyl)-4-[4-[4-(1-imidazolyl)butyl]phenoxymethyl]oxazole. The yield was 54%. Recrystallization from ethyl acetate-hexane gave colorless prisms, mp 118–120° C.

Working Example 125

Sodium hydride (oily, 60%, 660 mg) was added to a solution of 2-[(E)-2-phenylethenyl]-4-oxazolylmethanol (3.02 g) in N,N-dimethylformamide (30 ml) and stirred at 90° C. for 30 minutes, to which was added a solution of 2-chloro-5-[3-(1-imidazolyl)propyl]pyridine (1.10 g) in N,N-dimethylformamide (10 ml). The resultant was stirred at 90° C. for 14 hours. The reaction mixture was poured into water, and extracted with ethyl acetate. The ethyl acetate layer was washed with saturated aqueous sodium bicarbonate and brine, dried (MgSO$_4$), and concentrated under reduced pressure. The residue was subjected to a silica gel column chromatography. From the fraction eluted with ethyl acetate-hexane-methanol (10:1:0.5, v/v), crystals of 5-[3-(1-imidazolyl)propyl]-2-[2-[(E)-2-phenylethenyl]-4-oxazolylmethoxy]pyridine (900 mg, 47%) was obtained. Recrystallization ethyl acetate-hexane gave pale brown prisms, mp 120–121° C.

Working Example 126

In substantially the same manner as in Working Example 125, 2-(2-thienyl)-4-oxazolylmethanol was allowed to react with 2-chloro-5-[3-(1-imidazolyl)propyl]pyridine to give 5-[3-(1-imidazolyl)propyl]-2-[2-(2-thienyl)-4-oxazolylmethoxy]pyridine. The yield was 67%. Recrystallization from ethyl acetate-hexane gave brown prisms, mp 86–87° C.

Working Example 127

In substantially the same manner as in Working Example 8, 3-[4-[2-[(E)-2-phenylethenyl]-4-oxazolylmethylthio]phenyl]propyl mathanesulfonate was allowed to react with imidazole to give 4-[4-[3-(1-imidazolyl)propyl]phenylthiomethyl]-2-[(E)-2-phenylethenyl]oxazole. The yield was 70%. Recrystallization from ethyl acetate-hexane gave colorless prisms, mp 74–75° C.

Working Example 128

In substantially the same manner as in Working Example 62, 2-(9-fluorenylidenemethyl)-4-[4-[3-(1-imidazolyl)propyl]phenoxymethyl]oxazole was subjected to catalytic hydrogenation to give 2-(9-fluorenylmethyl)-4-[4-[3-(1-imidazolyl)propyl]phenoxymethyl]oxazole. The yield was 72%. Recrystallization from ethyl acetate-hexane gave colorless prisms, mp 145–146° C.

Working Example 129

To a solution 4-[4-[3-(1-imidazolyl)propyl]phenylthiomethyl]-2-[(E)-2-phenylethenyl]oxazole (500 mg) in dichloromethane (10 ml) was added to m-chloroperbenzoic acid (260 mg) at 0° C. and stirred for one hour. The reaction mixture was washed with aqueous sodium sulfite, saturated aqueous sodium bicarbonate and water in this order, dried (MgSO$_4$), and concentrated under reduced pressure. The residue was subjected to a silica gel column chromatography. From the fraction eluted with ethyl acetate-methanol (20:1, v/v), crystals of 4-[4-[3-(1-imidazolyl)propyl]phenylsulfonylmethyl]-2-[(E)-2-phenylethenyl]oxazole (380 mg, 73%) was obtained. Recrystallization from ethyl acetate-hexane gave colorless prisms, mp 116–117° C.

Working Example 130

In substantially the same manner as in Working Example 129, 4-[4-[3-(1-imidazolyl)propyl]phenylthiomethyl]-2-[(E)-2-phenylethenyl]oxazole (500 mg) was oxidized by use of m-chloroperbenzoic acid (540 mg) to give 4-[4-[3-(1-imidazolyl)propyl]phenylsulfonylmethyl]-2-[(E)-2-phenylethenyl]oxazole. The yield was 72%. Recrystallization from ethyl acetate-hexane gave colorless prisms, mp 140–141° C.

Working Example 131

A mixture of 2-(4-hydroxyphenyl)-4-[4-[3-(1-imidazolyl)propyl]phenoxymethyl]oxazole (300 mg), 2-chloromethylpyridine.hydrochloric acid (260 mg), potassium carbonate (330 mg) and N,N-dimethylformamide (10 ml) was stirred at 110° C. for 8 hours. The reaction mixture was poured into water, and extracted with ethyl acetate. The ethyl acetate-hexane was washed with water, dried (MgSO$_4$), and concentrated under reduced pressure. The residue was subjected to a silica gel column chromatography. From the fraction eluted with chloroform-methanol (50:1, v/v), crystals of 4-[4-[3-(1-imidazolyl)propyl]phenoxymethyl]-2-[4-(2-pyridylmethoxy)phenyl]oxazole (95 mg, 26%). Recrystallization from ethyl acetate-hexane gave colorless, mp 119–120° C.

Working Example 132

To a solution of 2-(4-hydroxyphenyl)-4-[4-[3-(1-imidazolyl)propyl]phenoxymethyl]oxazole (250 mg) in N,N-dimethylformamide (10 ml) was added sodium hydride (oily, 60%, 30 mg) and stirred at room temperature for one hour, to which chlorodiphenylmethane (270 mg) was added and stirred at 80° C. for 6 hours. The reaction mixture was poured into water, and extracted with ethyl acetate. The ethyl acetate layer was washed with 1N-sodium hydroxide and water, dried (MgSO$_4$), and concentrated under reduced pressure. The residue was subjected to a silica gel column chromatography. From the fraction eluted with ethyl acetate-methanol (50:1, v/v), crystals of 2-(4-diphenylmethoxyphenyl)-4-[4-[3-(1-imidazolyl)propyl]phenoxymethyl]oxazole (155 mg, 43%) was obtained. Recrystallization from ethyl acetate-hexane gave colorless prisms, mp 106–107° C.

Working Example 133

In substantially the same manner as in Working Example 131, 2-(4-hydroxyphenyl)-4-[4-[3-(1-imidazolyl)propyl]phenoxymethyl]oxazole was allowed to react with 4-chlorobenzylchloride to give 2-[4-(4-chlorobenzyloxy)phenyl]-4-[4-[3-(1-imidazolyl)propyl]phenoxymethyl]oxazole. The yield was 30%. Recrystallization from ethyl acetate-hexane gave colorless prisms, mp 151–152° C.

Working Example 134

In substantially the same manner as in Working Example 131, 2-(4-hydroxyphenyl)-4-[4-[3-(1-imidazolyl)propyl]phenoxymethyl]oxazole was allowed to react with piperonylchloride to give 4-[4-[3-(1-imidazolyl)propyl]phenoxymethyl]-2-[4-(3,4-methylenedioxyphenylmethoxy)phenyl]oxazole. The yield was 43%. Recrystallization from ethyl acetate-hexane gave colorless prisms, mp 124–125° C.

Working Example 135

To a mixture of 2-(5-chloro-2-thienyl)-4-[4-[3-(1-imidazolyl)propyl]phenoxymethyl]oxazole1 (600 mg), 2N-sodium carbonate (2.4 ml), tetrakis(triphenylphosphine)palladium (105 mg) and toluene (12 ml) was added dropwise aqueous phenylboronic acid (245 mg) in ethanol (3 ml) under argon-stream at room temperature and stirred at 90° C. for 15 hours. To the reaction mixture was added ethyl acetate, washed with 2N-sodium hydroxide and water, dried (MgSO$_4$), and concentrated under reduced pressure. The residue was subjected to a silica gel column chromatography. From the fraction eluted with chloroform-methanol (50:1, v/v), crystals of 4-[4-[3-(1-imidazolyl)propyl]phenoxymethyl]-2-(5-phenyl-2-thienyl)oxazole (430 mg, 54%) was obtained. Recrystallization from ethyl acetate-hexane gave pale yellow prisms, mp 128–129° C.

Working Example 136

In substantially the same manner as in Working Example 135, 6-bromo-2-[4-[3-(1-imidazolyl)propyl]phenoxymethyl]imidazo[1,2-a]pyridine was allowed to react with phenylboronic acid to give 2-[4-[3-(1-imidazolyl)propyl]phenoxymethyl]-6-phenylimidazo[1,2-a]pyridine. The yield was 78%. Recrystallization from ethyl acetate-hexane gave colorless prisms, mp 106–107° C.

Working Example 137

In substantially the same manner as in Working Example 135, 2-(5-bromo-2-furyl)-4-[4-[3-(1-imidazolyl)propyl]phenoxymethyl]oxazole was allowed to react with phenylboronic acid to give 4-[4-[3-(1-imidazolyl)propyl]phenoxymethyl]-2-(5-phenyl-2-furyl)oxazole. The yield was 92%. Recrystallization from ethyl acetate-isopropyl ether gave colorless needles, mp 130–131° C.

Working Example 138

A mixture of 2-(5-bromo-4-methyl-2-thienyl)-4-[4-[3-(1-imidazolyl)propyl]phenoxymethyl]oxazole (700 mg), zinc powder (200 mg), acetic acid (5 ml) and water (5 ml) was heated for 4 hours under reflux. The residue was filtered off, the filtrate was concentrated. To the residue was added ethyl acetate, washed with saturated aqueous sodium bicarbonate and water, dried (MgSO$_4$), and concentrated under reduced pressure to give crystals of 4-[4-[3-(1-imidazolyl)propyl]phenoxymethyl]-2-(4-methyl-2-thienyl)oxazole (470 mg, 81%). Recrystallization from ethyl acetate-hexane gave colorless prisms, mp 077–178° C.

Working Example 139

In substantially the same manner as in Working Example 138, 2-(5-bromo-4-methyl-2-thienyl)-4-[4-[4-(1-imidazolyl)butyl]phenoxymethyl]oxazole was reduced by zinc powder to give 4-[4-[4-(1-imidazolyl)butyl]phenoxymethyl]-2-(4-methyl-2-thienyl)oxazole. The yield was 89%. Recrystallization from ethyl acetate-hexane gave colorless prisms, mp 77–78° C.

Working Example 140

In substantially the same manner as in Working Example 72, 1-[3-(4-hydroxyphenyl)propyl]imidazole was allowed to react with 4-chloromethyl-2-(3-chloro-2-thienyl)oxazole to give 2-(3-chloro-2-thienyl)-4-[4-[3-(1-imidazolyl)propyl]phenoxymethyl]oxazole. The yield was 77%. Recrystallization from ethyl acetate-hexane gave colorless prisms, mp 69–70° C.

Working Example 141

In substantially the same manner as in Working Example 72, 1-[3-(4-hydroxyphenyl)propyl]imidazole was allowed to react with 4-chloromethyl-2-(4-chloro-2-thienyl)oxazole to give 2-(4-chloro-2-thienyl)-4-[4-[3-(1-imidazolyl)propyl]phenoxymethyl]oxazole. The yield was 80%. Recrystallization from ethyl acetate-hexane gave colorless prisms, mp 69–70° C.

Working Example 142

In substantially the same manner as in Working Example 72, 1-[3-(4-hydroxyphenyl)propyl]imidazole was allowed to react with 4-chloromethyl-2-(5-methoxy-2-thienyl)oxazole to give 4-[4-[3-(1-imidazolyl)propyl]phenoxymethyl]-2-(5-methoxy-2-thienyl)oxazole. The yield was 74%. Recrystallization from ethyl acetate-hexane gave colorless prisms, mp 96–97° C.

Working Example 143

In substantially the same manner as in Working Example 72, 1-[3-(4-hydroxyphenyl)propyl]imidazole was allowed to react with 4-chloromethyl-2-(3-furyl)oxazole to give 4-[4-[3-(1-imidazolyl)propyl]phenoxymethyl]-2-(3-furyl)oxazole. The yield was 93%. Recrystallization from ethyl acetate-hexane gave colorless prisms, mp 85–87° C.

Working Example 144

In substantially the same manner as in Working Example 72, 1-[4-(4-hydroxyphenyl)butyl]imidazole was allowed to react with 4-chloromethyl-2-(5-methyl-2-furyl)oxazole to give 4-[4-[4-(1-imidazolyl)butyl]phenoxymethyl]-2-(5-methyl-2-furyl)oxazole. The yield was 99%. Recrystallization from ethyl acetate-hexane gave colorless prisms, mp 91–92° C.

Working Example 145

Sodium hydride (oily, 60%, 120 mg) was added to ethanol (15 ml) at 0° C. and stirred at room temperature for one hour, to which 1-[3-(4-hydroxyphenyl)propyl]imidazole (506 mg) was added, and stirred at room temperature for further one hour. 4-chloromethyl-2-(2-thienylmethyl)oxazole (580 mg) was added and heated for 4 hours under reflux. The reaction mixture was concentrated, to which water was added, and extracted with ethyl acetate. The ethyl acetate layer was washed with 2N-sodium hydroxide and brine, dried (MgSO$_4$), and concentrated under reduced pressure. The residue was subjected to a silica gel column chromatography. From the fraction eluted with ethyl acetate-methanol (95:5, v/v), 4-[4-[3-(1-imidazolyl)propyl]phenoxymethyl]-2-(2-thienylmethyl)oxazole. The yield was 93%. Oily substance.

NMR(δ ppm in CDCl$_3$): 2.0–2.2(2H,m), 2.56(2H,t,J=7.4 Hz), 3.92(2H,t,J=7.2 Hz), 4.33(2H,s), 4.96(2H,s), 6.85–7.0 (5H,m), 7.0–7.1(3H,m), 7.15–7.25(1H,m), 7.45(1H,s), 7.61 (1H,s).

Working Example 146

To a mixture of 2-(1-pyrrolyl)-4-thiazolylmethanol (0.45 g), triethylamine (0.42 ml) and ethyl acetate (20 ml) was added dripwise methanesulfonyl chloride (0.23 ml) at 0° C., and then stirred for one hour. To the reaction mixture was added water, and the ethyl acetate layer was separated, washed with water, dried (MgSO$_4$), and concentrated under reduced pressure. The residue was dissolved in tetrahydrofuran (5 ml), which was added to a solution prepared by adding sodium hydride (oily, 60%, 92 mg) to a solution of 1-[3-(4-hydroxyphenyl)propyl]imidazole (420 mg) in N,N-dimethylformamide (10 ml). After stirring for 2 hours, the reaction mixture was poured into water and extracted with ethyl acetate. The ethyl acetate layer was washed with 2N-aqueous sodium hydroxide and then water, dried (MgSO$_4$), and concentrated under reduced pressure. The residue was subjected to a silica gel column chromatography. From the fraction eluted with ethyl acetate-methanol (95:5, v/v), crystals were obtained. Recrystallization from ethyl acetate-hexane gave 4-[4-[3-(1-imidazolyl)propyl] phenoxymethyl]-2-(1-pyrrolyl)thiazole (530 mg, 70%), colorless prisms, mp 93–94° C.

Working Example 147

In substantially the same manner as in Working Example 146, 2-(3-pyridyl)-4-thiazolylmethanol was mesylated, which was allowed to react with 1-[3-(4-hydroxyphenyl) propyl]imidazole to give 4-[4-[3-(1-imidazolyl)propyl] phenoxymethyl]-2-(3-pyridyl)thiazole. The yield was 35%. Recrystallization from ethyl acetate-hexane gave colorless prisms, mp 67–68° C.

Working Example 148

In substantially the same manner as in Working Example 72, 1-[3-(4-hydroxyphenyl)propyl]imidazole was reacted with 4-chlorometyl-2-(5-cyano-2-thienyl)oxazole to obtain 2-(5-cyano-2-thienyl)-4-[4-[3-(1-imidazolyl)propyl] phenoxymethyl]oxazole. The yield was 70%. Recrystallization from ethyl acetate-hexane gave colorless prisms, mp 73–74° C.

Working Example 149

In substantially the same manner as in Working Example 72, 1-[3-(4-hydroxy-3-methoxyphenyl)propyl]imidazole was reacted with 4-chloromethyl-2-(2-thienyl)oxazole to obtain 4-[4-[3-(1-imidazolyl)propyl]-2-methoxyphenoxymethyl]-2-(2-thienyl)oxazole. The yield was 80%. Recrystallization from ethyl acetate-hexane gave colorless prisms, mp 94–95° C.

Working Example 150

In substantially the same manner as in Working Example 72, 1-[3-(4-hydroxy-3-methoxyphenyl)propyl]imidazole was reacted with 4-chloromethyl-2-(5-methyl-2-thienyl) oxazole to obtain 4-[4-[3-(1-imidazolyl)propyl]-2-methoxyphenoxymethyl]-2-(5-methyl-2-thienyl)oxazole. The yield was 72%. Recrystallization from ethyl acetate-hexane gave colorless prisms, mp 92–93° C.

Working Example 151

In substantially the same manner as in Working Example 72, 1-[3-(3-chloro-4-hydroxyphenyl)propyl]imidazole was reacted with 4-chloromethyl-2-(2-thienyl)oxazole to obtain 4-[2-chloro-4-[3-(1-imidazolyl)propyl]phenoxymethyl]-2-(2-thienyl)oxazole. The yield was 77%. Recrystallization from ethyl acetate-hexane gave colorless prisms, mp 93–94° C.

Working Example 152

In substantially the same manner as in Working Example 72, 1-[3-(3-chloro-4-hydroxyphenyl)propyl]imidazole was reacted with 4-chloromethyl-2-(5-methyl-2-thienyl)oxazole to obtain 4-[2-chloro-4-[3-(1-imidazolyl)propyl] phenoxymethyl]-2-(5-methyl-2-thienyl)oxazole. The yield was 83%. Recrystallization from ethyl acetate-hexane gave colorless prisms, mp 95–96° C.

Working Example 153

In substantially the same manner as in Working Example 72, 1-[4-(4-hydroxyphenyl)butyl]imidazole was reacted with 4-chloromethyl-2-(2-thienyl)thiazole to obtain 4-[4-[4-(1-imidazolyl)butyl]phenoxymethyl]-2-(2-thienyl)thiazole. The yield was 82%. Recrystallization from ethyl acetate-hexane gave colorless prisms, mp 108–109° C.

Working Example 154

In substantially the same manner as in Working Example 72, 1-[3-(4-hydroxyphenyl)propyl]imidazole was reacted with 3-chloromethyl-7-(2-thienyl)quinoline to obtain 3-[4-[3-(1-imidazolyl)propyl]phonexymethyl]-7-(2-thienyl) quinoline. The yield was 82%. Recrystallization from ethanol gave colorless prisms, mp 157–158° C.

Working Example 155

Diethyl azodicarboxylate (1.20 g) was added dropwise to a stirred mixture of 2-(2-thienyl-4-oxazolyl)ethanol (700 mg). 1-[3-(4-hydroxyphenyl)propyl]imidazole (670 mg), triphenylphosphine (1.73 g), and tetrahydrofuran (50 ml) at room temperature. After refluxing for 3 h, the reaction mixture was concentrated. The residue was purified by silica gel column chromatography. From the fraction eluted with ethyl acetate-methanol (100:1, v/v) 4-[2-[4-[3-(1-imidazolyl)propyl]phenoxy]ethyl]-2-(2-thienyl)oxazole (690 mg, 55%) was obtained. Recrystallization from ethyl acetate-hexane gave colorless prisms, mp 77–78° C.

Working Example 156

In substantially the same manner as in Working Example 146, 3-[2-(2-thienyl)-4-oxazolyl]propanol was mesylated and then reacted with 1-[3-(4-hydroxyphenyl)propyl] imidazole to obtain 4-[3-[4-[3-(1-imidazolyl)propyl] phenoxy]propyl]-2-(2-thienyl)oxazole. The yield was 72%. Recrystallization from ethyl acetate-hexane gave colorless prisms, mp 99–100° C.

Working Example 157

In substantially the same manner as in Working Example 146, 4-(2-thienyl)-2-thiazolylmethanol was mesylated and then reacted with 1-[3-(4-hydroxyphenyl)propyl]imidazole to obtain 2-[4-[3-(1-imidazolyl)propyl]phenoxymethyl]-4-(2-thienyl)oxazole. The yield was 84%. Recrystallization from ethyl acetate-hexane gave colorless prisms, mp 123–124° C.

Working Example 158

In substantially the same manner as in Working Example 146, 5-(2-thienyl)-2-thiazolylmethanol was mesylated and then reacted with 1-[3-(4-hydroxyphenyl)propyl]imidazole to obtain 2-[4-[3-(1-imidazolyl)propyl]phenoxymethyl]-5-(2-thienyl)thiazole. The yield was 66%. Recrystallization from ethyl acetate-hexane gave orange prisms, mp 82–84° C.

Working Example 159

2-(2-thienyl)-5-thiazolylmethanol (395 mg) was dissolved in thionyl chloride (3 ml) at 0° C. After stirring for 15 min. the reaction mixture was concentrated. The residue was dissolved in ethyl acetate and washed with saturated aqueous sodium bicarbonate and water. The ethyl acetate layer was separated, dried (MgSO$_4$), and concentrated. The residue was dissolved in tetrahydrofuran (5 ml) and then added to a stirred solution prepared from 60% sodium hydride in oil (76 mg), 1-[3-(4-hydroxyphenyl)propyl] imidazole (344 mg) and N,N-dimethylformamide (10 ml). After stirring for 2 h, the reaction mixture was poured into water and extracted with ethyl acetate. The ethyl acetate layer was washed with 2N sodium hydroxide solution and water, dried (MgSO$_4$), and concentrated to obtain 5-[4-[3-(1-imidazolyl)propyl]phenoxymethyl]-2-(2-thienyl)thiazole (567 mg, 87%). Recrystallization from ethyl acetate-hexane gave pale yellow prisms, mp 112–113° C.

Working Example 160

In substantially the same manner as in Working Example 159, 2-(2-thienyl)-5-thiazolylmethanol was chlorinated and then reacted with 1-[4-(4-hydroxyphenyl)butyl]imidazole to obtain 5-[4-[4-(1-imidazolyl)butyl]phenoxymethyl]-2-(2-thienyl)thiazole. The yield was 86%. Recrystallization from ethyl acetate-hexane gave pale yellow prisms, mp 128–129° C.

Working Example 161

In substantially the same manner as in Working Example 72, 1-[3-(4-hydroxyphenyl)propyl]imidazole was reacted with 4-chloromethyl-2-(5-methyl-2-thienyl)thiazole to obtain 4-[4-[3-(1-imidazolyl)propyl]phenoxymethyl]-2-(5-methyl-2-thienyl)thiazole. The yield was 88%. Recrystallization from ethyl acetate-hexane gave colorless needles, mp 78–79° C.

Working Example 162

In substantially the same manner as in Working Example 72, 1-[4-(4-hydroxyphenyl)butyl]imidazole was reacted with 4-chloromethyl-2-(5-methyl-2-thienyl)thiazole to obtain 4-[4-[4-(1 -imidazolyl)butyl]phenoxymethyl]-2-(5-methyl-2-thienyl)thiazole. The yield was 74%. Recrystallization from ethyl acetate-hexane gave pale yellow needles, mp 81–82° C.

Working Example 163

In substantially the same manner as in Working Example 72, 1-[3-(4-hydroxyphenyl)propyl]imidazole was reacted with 2-chloromethyl-5-(2-thienyl)oxazole to obtain 2-[4-[3-(1-imidazolyl)propyl]phenoxymethyl]-5-(2-thienyl)oxazole. The yield was 90%. Recrystallization from ethyl acetate-hexane gave colorless prisms, mp 75–76° C.

Working Example 164

In substantially the same manner as in Working Example 72, 1-[4-(4-hydroxyphenyl)butyl]imidazole was reacted with 2-chloormethyl-5-(2-thienyl)oxazole to obtain 2-[4-[4-(1-imidazolyl)butyl]phenoxymethyl]-5-(2-thienyl)oxazole. The yield was 98%. Recrystallization from ethyl acetate-hexane gave pale yellow prisms, mp 136–138° C.

Working Example 165

A solution of 4-[4-[3-(1-imidazolyl)propyl] phenoxymethyl]-2-[(E)-2-(2-thienyl)ethenyl]oxazole (200 mg) in methanol (10 ml)-tetrahydrofuran (4 ml) was hydrogenated on palladium carbon (10%, wet, 70 mg) at 4 atm. After removal of the catalyst by filtration, the filtrate was concentrated. The hydrogenation was repeated three times to obtain 4-[4-[3-(1-imidazolyl)propyl]phenoxymethyl]-2-[2-(2-thienyl)ethyl]oxazole. Recrystallization from ethyl acetate-methanol gave colorless prisms (155 mg, 79%), mp 68–70° C.

Working Example 166

In substantially the same manner as in Working Example 72, 1-[3-(4-hydroxyphenyl)propyl]imidazole was reacted with 5-chloromethyl-3-phenyl-1,2,4-oxadiazole to obtain 5-[4-[3-(1-imidazolyl)propyl]phenoxymethyl]-3-phenyl-1,2,4-oxadiazole. The yield was 51%. Recrystallization from ethyl acetate-hexane gave colorless needles, mp 124–125° C.

Working Example 167

In substantially the same manner as in Working Example 72, 1-[3-(4-hydroxyphenyl)propyl]imidazole was reacted with 5-chloromethyl-3-(2-thienyl)-1,2,4-oxadiazole to obtain 5-[4-[3-(1-imidazolyl)propyl]phenoxymethyl]-3-(2-thienyl)-1,2,4-oxadiazole. The yield was 41%. Recrystallization from ethyl acetate-hexane gave pale yellow prisms, mp 118–119° C.

Working Example 168

In substantially the same manner as in Working Example 72, 1-[4-(4-hydroxyphenyl)butyl]imidazole was reacted with 5-chloromethyl-3-(2-thienyl)-1,2,4-oxadiazole to obtain 5-[4-[4-(1-imidazolyl)butyl]phenoxymethyl]-3-(2-thienyl)-1,2,4-oxadiazole. The yield was 29%. Recrystallization from a ethyl acetate-MeOH gave colorless prisms, mp 94–95° C.

INDUSTRIAL APPLICABILITY

The present invention provides the compounds having excellent actions of inhibiting tyrosine kinase and provides the antitumor agents, with less adverse side effects, based on novel action mechanism.

The compound (I) of this invention or salts thereof have tyrosine kinase inhibiting activity, which can be used for prophylaxis or therapy of tyrosine kinase dependent diseases in mammals. These tyrosine kinase dependent diseases include diseases stimulating cell proliferation due to abnormal tyrosine kinase activity. In other words, the compound (I) or salts thereof can be safely used as prophylaxis or therapy of diseases caused by abnormal cell proliferation including, among others, breast cancer, prostate cancer, pancreactic cancer, gastric cancer, or atherosclerosis, angiogenesis (solid tumor or sarcoma accompanied with angiogenesis, metastatis of tumors accompanied with angiogenesis, and diabetic retinopathy accompanied with angiogenesis), viral diseases (e.g. HIV infection).

Tyrosine kinase dependent diseases further include cardiovascular disease associated with abnormal tyrosine kinase activities. Therefore, the compound (I) of this invention or salts thereof can be used also for prophylaxis or therapy of cardiovascular diseases such as restenosis.

The compound (I) of this invention or salts thereof are useful as antitumor agents such as therapeutic agents, especially, breast cancer, prostate cancer, pancreatic cancer and gastric cancer.

What is claimed is:

1. A heterocyclic compound represented by the formula:

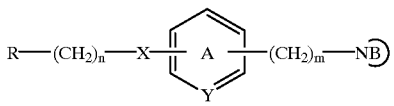

wherein R stands for an aromatic heterocyclic group which may be optionally substituted, X stands for an oxygen atom, an optionally oxidized sulfur atom, —C(=O)— or —CH(OH)—, Y stands for CH or N m stands for an integer of 1 to 10, n stands for an integer of 1 to 5, the cyclic group

stands for an aromatic azole group which may be substituted, and the ring A may be further substituted, or a salt thereof.

2. The compound according to claim 1, wherein the cyclic group;

is pyrrolyl, imidazolyl, pyrazolyl, triazolyl, tetrazolyl or benzimidazolyl, or they may be substituted with one or two groups selected from (i) alkyl, (ii) aryl, (iii) hydroxyalkyl, (iv) carboxyl, (v) alkoxycarbonyl and (vi) carbamoyl.

3. The compound according to claim 1, wherein m is an integer of 3 to 5.

4. The compound according to claim 1, wherein n is 1.

5. The compound according to claim 2, wherein X is oxygen atom.

6. The compound according to claim 1, wherein R is an optionally substituted oxazolyl or an optionally substituted thiazolyl.

7. The compound according to claim 1, wherein R is oxazolyl, benzoxazolyl or thiazolyl, or they may be substituted with one or two groups selected from, (i) aryl which may be substituted with one or two groups selected from hydroxyl, alkoxy, arylalkoxy, alkyl, cyano, halogen atom and tetrazolyl, (ii) alkyl, (iii) hydroxyalkyl, (iv) alkoxycarbonylalkyl, (v) alkyl substituted with one or two aryl groups, (vi) alkenyl substituted with one or two aryl groups, (vii) cycloalkyl, (viii) a partially saturated naphthyl, (ix) thienyl or furyl, or they may be substituted with one or two groups selected from hydroxy, alkoxy, arylalkoxy group, alkyl, cyano, aryl and hydrogen atom, (x) benzofuranyl and (xi) benzothienyl.

8. The compound according to claim 1, wherein R is oxazolyl, benzoxazolyl or thiazolyl, or they may be substituted with one or two groups selected from (i) aryl which may be substituted with one or two groups selected from hydroxyl, alkoxy, arylalkoxy, alkyl, cyano, halogen atom and tetrazolyl, (ii) alkyl, (iii) hydroxyalkyl, (iv) alkoxycarbonylalkyl, (v) alkyl substituted with one or two aryl groups, (vi) alkenylsubstituted with one or two aryl groups, (vii) cycloalkyl, (viii) a partially saturated naphthyl, (ix) thienyl or furyl, or they may be substituted with one or two groups selected from hydoxy, alkoxy, arylalkoxy, alkyl, cyano, aryl and hydrogen atom, (x) benzofuranyl and (xi) benzothienyl, X is oxygen atom, m is an integer of 0 to 6, n is 1, the cyclic group;

is pyrrolyl, imidazolyl, pyrazolyl, triazolyl, tetrazoryl or benzimidazolyl, or they may be substituted with one or two groups selected from (i) alkyl, (ii) aryl, (iii) hydroxyalkyl, (iv) carboxyl, (v) alkoxycarbonyl and (vi) carbamoyl.

9. The compound according to claim 1, wherein R is oxazolyl substituted with arylalkenyl or arylalkoxyaryl, X is oxygen atom, m is 3 or 4, n is 1, the cyclic group;

is imidazolyl or triazolyl, the ring A is 1,3-phenylene or 1,4-phenylene.

10. The compound according to claim 1, wherein R is oxazolyl or thiazolyl substituted with thienyl, X is oxygen atom, m is 3 or 4, n is 1 and the cyclic group;

is imidazolyl or triazolyl.

11. The compound according to claim 1, wherein R is benzoxazolyl substituted with thienyl, X is oxygen atom, m is 3 or 4, n is 1, the cyclic group;

is imidazolyl or triazolyl, the ring A is 1,3-phenylene or 1,4-phenylene.

12. The compound according to claim 1, which is
1-[4-[4-[2-[(E)-2-phenylethenyl]-4-oxazolylmethoxy] phenyl]butyl-1,2,4-triazole or a salt thereof,
4-[4-[4-(1-imidazolyl)butyl]phenoxymethyl]-2-[(E)-2-phenylethenyl]oxazole or a salt thereof,
4-[4-[3-(1-imidazolyl)propyl]phenoxymethyl]-2-[(E)-2-phenylethenyl]oxazole or a salt thereof,
4-[3-[3-(1-imidazolyl)propyl]phenoxymethyl]-2-[(E)-2-phenylethenyl]oxazole or a salt thereof,
2-(4-benzyloxyphenyl)-4-[4-[3-(1-imidazolyl)propyl] phenoxymethyl]oxazole a salt thereof,
4-[4-[3-(1-imidazolyl)propyl]phenoxymethyl]-2-(2-thienyl) oxazole or a salt thereof,
4-[4-[3-(1-imidazolyl)propyl]phenoxymethyl]-2-(5-methyl-2-thienyl)oxazole or a salt thereof,
2-(5-chloro-2-thienyl)-4-[4-[3-(1-imidazolyl)propyl] phenoxymethyl]oxazole or a salt thereof,
4-[4-[3-(1-imidazolyl)propyl]phenoxymethyl]-2-(2-thienyl) thiazole or a salt thereof, or
5-[4-[3-(1-imidazolyl)propyl]phenoxymethyl]-2-(2-thienyl) benzoxazole or a salt thereof.

13. A pharmaceutical composition which comprises a compound as claimed in claim 1 and a pharmaceutically acceptable carrier.

14. The pharmaceutical composition according to claim 13, which is a composition for antitumor.

15. The pharmaceutical composition according to claim 14, which is a composition for prophylaxis or treatment of breast cancer or prostate cancer.

16. A tyrosine kinase inhibitor comprising a compound or a salt thereof as claimed in claim 1 and a pharmaceutically acceptable carrier.

17. A method for preparation of a medicinal agent for prophylaxis or treatment of cancer comprising admixing a compound as claimed in claim 1 with a pharmaceutically acceptable carrier.

18. A method which comprises administering an effective amount of a compound as claimed in claim 1 in a pharmaceutically acceptable carrier to provide a prophylactic or therapeutic action for cancer in warm blooded animals.

19. A method for producing a compound represented by the formula:

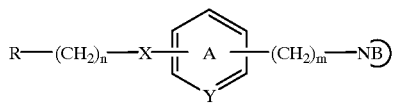

wherein R stands for an aromatic heterocyclic group which may be optionally substituted, X stands for oxygen atom, an optionally oxidized sulfur atom, —C(=O)— or —CH(OH),
Y stands for CH or N,
m stands for an integer of 1 to 10,
n stands for an integer of 1 to 5,
the cyclic group;

stands for an aromatic azole group which may be substituted,
and the ring A may be further substituted,
or a salt thereof,
which comprises reacting a compound represented by the formula:

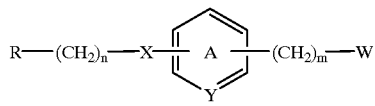

wherein W stands for a leaving group and other symbols are the same as above, or a salt thereof,
with a compound represented by the formula:

H—NB wherein the cyclic group;

stands for an aromatic azole group which may be substituted, or a salt thereof.

20. The compound according to claim 1, wherein X is oxygen atom, an optionally oxidized sulfur atom or —CH (OH).

21. The compound according to claim 1, wherein the cyclic group

is a 5-membered aromatic monocyclic heterocyclic group containing, as the ring forming atoms besides the carbon atoms, 1 to 4 nitrogen atoms and optionally containing one oxygen atom or one sulfur atom, which may be substituted.

* * * * *